United States Patent
Liu et al.

(10) Patent No.: US 12,146,166 B2
(45) Date of Patent: Nov. 19, 2024

(54) GENERATION OF INDUCED PLURIPOTENT CELLS BY CRISPR ACTIVATION

(71) Applicant: The J. David Gladstone Institutes, a Testamentary Trust Established Under the Will of J. David Gladstone, San Francisco, CA (US)

(72) Inventors: Peng Liu, San Francisco, CA (US); Sheng Ding, San Francisco, CA (US)

(73) Assignee: THE J. DAVID GLADSTONE INSTITUTES, San Francisco, CA (US), A TESTAMENTARY TRUST ESTABLISHED UNDER THE WILL OF J. DAVID GLADSTONE ( * ) Notice: Subject to any disclaimer, the term of this patent is extended or adjusted under 35 U.S.C. 154(b) by 541 days.

(21) Appl. No.: 16/957,086

(22) PCT Filed: Dec. 27, 2018

(86) PCT No.: PCT/US2018/067679
§ 371 (c)(1),
(2) Date: Jun. 22, 2020

(87) PCT Pub. No.: WO2019/133714
PCT Pub. Date: Jul. 4, 2019

(65) Prior Publication Data
US 2020/0339958 A1    Oct. 29, 2020

Related U.S. Application Data

(60) Provisional application No. 62/611,202, filed on Dec. 28, 2017.

(51) Int. Cl.
| | |
|---|---|
| *C12N 5/074* | (2010.01) |
| *C07K 14/47* | (2006.01) |
| *C12N 9/22* | (2006.01) |
| *C12N 15/113* | (2010.01) |
| *C12N 15/90* | (2006.01) |

(52) U.S. Cl.
CPC ............ *C12N 5/0696* (2013.01); *C12N 9/22* (2013.01); *C12N 15/113* (2013.01); *C12N 15/907* (2013.01); *C07K 14/4702* (2013.01); *C12N 2310/20* (2017.05); *C12N 2501/602* (2013.01); *C12N 2501/603* (2013.01); *C12N 2501/604* (2013.01); *C12N 2501/605* (2013.01); *C12N 2501/606* (2013.01); *C12N 2501/608* (2013.01); *C12N 2501/65* (2013.01); *C12N 2501/70* (2013.01)

(58) Field of Classification Search
CPC ............ C12N 2501/602; C12N 15/113; C12N 5/0696
See application file for complete search history.

(56) References Cited

U.S. PATENT DOCUMENTS

| | | |
|---|---|---|
| 2015/0191744 A1 | 7/2015 | Wolfe et al. |
| 2016/0237455 A1* | 8/2016 | Glucksmann .......... C12N 15/85 |
| 2016/0281063 A1 | 9/2016 | Burke et al. |
| 2017/0219596 A1 | 8/2017 | Tanenbaum et al. |

FOREIGN PATENT DOCUMENTS

| | | | |
|---|---|---|---|
| CN | 104120107 A | 10/2014 | |
| JP | 2017-506904 A | 3/2017 | |
| WO | WO-2015134652 A1 * | 9/2015 | ............ C12N 15/86 |
| WO | WO 2016/201399 A1 | 12/2016 | |

OTHER PUBLICATIONS

Chavez et al. Highly efficient Cas9-mediated transcriptional programming. Nature Methods 2015, 12(4): 326-328. (Year: 2015).*
Tanenbaum et al. A protein-tagging system for signal amplification in gene expression and fluorescence imaging. Cell 2014, 159:635-646. (Year: 2014).*
Hu et al. Direct activation of human and mouse Oct4 genes using engineered TALE and Cas9 transcription factors. Nucleic Acids Research 2014, 42;7:4375-4390. (Year: 2014).*
Hu et al. Direct activation of human and mouse Oct4 genes using engineered TALE and Cas9 transcription factors. Nucleic Acids Research 2014, supplemental 1-19. (Year: 2014).*
Balboa et al. Conditionally staibilized dCas9 activator for controlling gene expression in human cell reprogramming and differentiation. Stem Cell Reports 2015, 5:448-459. (Year: 2015).*
Hilton et al. Epigenome editing by a CRISPR-Cas9-based acetyltransferase activates genes from promoters and enhancers. Nature Biotechnology 2015, 33;5:510-519. (Year: 2015).*
Arai et al., "Dose-dependent transduction of vesicular stomatitis virus G protein-pseudotyped retrovirus vector into human solid tumor cell lines and murine fibroblasts," *Virology* 260:109-115 (1999).
Black et al., "Targeted Epigenetic Remodeling of Endogenous Loci by CRISPR/Cas9-Based Transcriptional Activators Directly Converts Fibroblasts to Neuronal Cells," *Cell Stem Cell*, 19:406-414 (2016).
Buganim et al., "Single-cell expression analyses during cellular reprogramming reveal an early stochastic and a late hierarchic phase," *Cell*, 150:1209-1222 (2012).
Chakraborty et al., "A CRISPR/Cas9-based system for reprogramming cell lineage specification," *Stem Cell Reports*, 3:940-947 (2014).
Chavez et al., "Highly efficient Cas9-mediated transcriptional programming," *Nat Methods*, 12:326-328 (2015).

(Continued)

*Primary Examiner* — Allison M Fox
*Assistant Examiner* — Jennifer S Spence
(74) *Attorney, Agent, or Firm* — Greenberg Traurig, LLP

(57) ABSTRACT

The present Application is related to methods and compositions for reprogramming adult somatic cells into induced pluripotent stem cells by targeting and remodeling endogenous gene loci without relying on ectopic expression of transcription factors.

13 Claims, 22 Drawing Sheets
Specification includes a Sequence Listing.

(56) References Cited

OTHER PUBLICATIONS

Cheng et al., "Multiplexed activation of endogenous genes by CRISPR-on, an RNA-guided transcriptional activator system," *Cell Res*, 23:1163-1171 (2013).
Cong et al., "Multiplex genome engineering using CRISPR/Cas systems," *Science*, 339:819-823 (2013).
Di Stefano et al., "C/EBPalpha poises B cells for rapid reprogramming into induced pluripotent stem cells," *Nature*, 506:235-239 (2014).
Dominguez et al., "Beyond editing: repurposing CRISPR-Cas9 for precision genome regulation and interrogation," *Nat. Rev. Mol. Cell Biol.*, 17(1):5-15 (2015).
Gilbert et al., "CRISPR-mediated modular RNA-guided regulation of transcription in eukaryotes," *Cell*, 154:442-451 (2013).
Heng et al., "The nuclear receptor Nr5a2 can replace Oct4 in the reprogramming of murine somatic cells to pluripotent cells," *Cell Stem Cell*, 6:167-174 (2010).
Hirai et al., "Structure and functions of powerful transactivators: VP16, MyoD and FoxA," *Int J Dev Biol*, 54:1589-1596 (2010).
Jinek et al., "A programmable dual-RNA-guided DNA endonuclease in adaptive bacterial immunity," *Science*, 337:816-821 (2012).
Kagey et al., "Mediator and cohesin connect gene expression and chromatin architecture," *Nature*, 467:430-435 (2010).
Kearns et al., "Functional annotation of native enhancers with a Cas9-histone demethylase fusion," *Nat Methods*, 12:401-403 (2015).
Konermann et al., "Genome-scale transcriptional activation by an engineered CRISPR-Cas9 complex," *Nature* 517:583-588 (2015).
Liu et al., "Editing DNA Methylation in the Mammalian Genome," *Cell*, 167:233-247 (2016).
Maekawa et al., "Direct reprogramming of somatic cells is promoted by maternal transcription factor Glis1," *Nature* 474:225-229 (2011).
Mali et al., "CAS9 transcriptional activators for target specificity screening and paired nickases for cooperative genome engineering," *Nat Biotechnol*, 31:833-838 (2013).
Mali et al., "RNA-guided human genome engineering via Cas9," *Science*, 339:823-826 (2013).
Polo et al., "A molecular roadmap of reprogramming somatic cells into iPS cells," *Cell*, 151:1617-1632 (2012).
Polstein et al., "Genome-wide specificity of DNA binding, gene regulation, and chromatin remodeling by TALE- and CRISPR/Cas9-based transcriptional activators," *Genome Res*, 25:1158-1169 (2015).
Pulecio et al., "CRISPR/Cas9-Based Engineering of the Epigenome," *Cell Stem Cell*, 21:431-447 (2017).
Smith et al., "Molecular features of cellular reprogramming and development," *Nat Rev Mol Cell Biol*, 17:139-154 (2016).
Soufi et al., "Facilitators and impediments of the pluripotency reprogramming factors' initial engagement with the genome," *Cell*, 151:994-1004 (2012).
Stemmer et al., "CCTop: An Intuitive, Flexible and Reliable CRISPR/Cas9 Target Prediction Tool," *PLoS One*, 10:e0124633 (2015).
Szabo et al., "Allele-specific expression of imprinted genes in mouse migratory primordial germ cells," *Mech Dev*, 115:157-160 (2002).
Takahashi et al., "Induction of pluripotent stem cells from mouse embryonic and adult fibroblast cultures by defined factors," *Cell*, 126(4): 663-676 (2006).
Thakore et al., "Highly specific epigenome editing by CRISPR-Cas9 repressors for silencing of distal regulatory elements," *Nat Methods*, 12:1143-1149 (2015).
Vasileva et al., *Cell Death and Disease*, "Genome-editing tools for stem cell biology," 6(1):1-8 (2015).
Wei et al., "Klf4 organizes long-range chromosomal interactions with the oct4 locus in reprogramming and pluripotency," *Cell Stem Cell*, 13:36-47 (2013).
Weltner et al., "Human pluripotent reprogramming with CRISPR activators," *Nat. Commun.*, 9(1):2643 (2018).
Weltner et al., "Human pluripotent reprogramming with CRISPR activators," *bioRxiv.*, pp. 1-31 (2017).
Whyte et al., "Master transcription factors and mediator establish super-enhancers at key cell identity genes," *Cell*, 153:307-319 (2013).
Yeom et al., "Germline regulatory element of Oct-4 specific for the totipotent cycle of embryonal cells," *Development*, 122:881-894 (1996).
Zalatan et al., "Engineering complex synthetic transcriptional programs with CRISPR RNA scaffolds," *Cell*, 160:339-350 (2015).
Gao et al., "Comparison of TALE designer transcription factors and the CRISPR/dCas9 in regulation of geneexpression by targeting enhancers", Nucleic Acids Res. Nov. 10, 2014;42(20):e155.
Papaperou et al., "Stoichiometric and temporal requirements of Oct4, Sox2, Klf4, and c-Myc expression for efficient human iPSC induction and differentiation", PNAS, 2009, vol. 106, No. 31, 12759-12764.

* cited by examiner

GENERATION OF INDUCED PLURIPOTENT CELLS BY CRISPR ACTIVATION

RELATED APPLICATION

This application is a U.S. National Stage Application under 35 U.S.C. § 371 of International Patent Application No. PCT/US2018/067679, filed Dec. 27, 2018, which claims priority to U.S. Provisional Application Ser. No. 62/611,202, filed Dec. 28, 2017, the disclosures of each of which are hereby incorporated by reference in their entirety.

This application incorporates by reference in its entirety the Computer Readable Form ("CRF") of a Sequence Listing in ASCII text format submitted via EFS-Web. The Sequence Listing text file submitted via EFS-Web is entitled "13601-222-999_Sequence_Listing.txt," was created on Jun. 22, 2020 and is 38,592 bytes in size.

FIELD

The ability to reprogram adult somatic cells into pluripotent stem cells through the modulation of specific transcription factors is of great interest to basic biological research and also holds much hope for regenerative medicine, where induced pluripotent stem cells (iPSCs) can be differentiated into any cell type of the body to treat numerous diseases and disorders. A continued challenge in this field has been to generate iPSCs without relying on ectopic expression of transcription factors. This disclosure provides novel methods and compositions to induce pluripotent stem cells by targeting and remodeling endogenous gene loci.

BACKGROUND

Pluripotent stem cells hold great promise for regenerative medicine. A better understanding of how endogenous chromatin remodeling leads to pluripotency induction is of significant interest. Conventionally, differentiated somatic cells can be reprogrammed into induced pluripotent stem cells (iPSCs) by ectopic expression of Oct4, Sox2, Klf4, and c-Myc (OSKM) (Takahashi and Yamanaka, 2006). Overexpressed Oct4, Sox2, and Klf4 initially bind to and globally remodel endogenous loci across the genome (Soufi et al., 2012), ultimately leading to the establishment of pluripotent regulatory circuitry.

However, it is largely unknown what precise remodeling events on endogenous chromatin trigger reprogramming towards pluripotency. For one, it is not clear whether simultaneous remodeling of a large number of pluripotency-related loci is necessary or whether precise remodeling of a single locus is sufficient for iPSC induction. In addition, Oct4, Sox2, and Klf4 target the distal elements of many genes required for reprogramming (Soufi et al., 2012), but how the remodeling of these distal elements affects pluripotency induction is poorly understood. Furthermore, epigenetic remodeling is the central mechanism of cellular reprogramming (Smith et al., 2016), but it has not been determined if iPSC induction can be initiated by epigenetic manipulation of any defined endogenous loci. Finally, due to methodological limitations, there is no direct evidence of whether pluripotency can be induced by precise remodeling of an endogenous gene locus.

Recently, the type II clustered regularly interspaced short palindromic repeat (CRISPR) and CRISPR-associated 9 (Cas9) nuclease system (CRISPR/Cas9 system) from bacteria was repurposed as a powerful tool for genetic editing in mammalian cells (Cong et al., 2013; Jinek et al., 2012; Mail et al., 2013b). A nuclease-deactivated form of Cas9 (dCas9) has been engineered as programmable synthetic transcription factors when fused with transactivation domains. This system is termed the CRISPR activation (CRISPRa) system (Chavez et al., 2015; Gilbert et al., 2013; Konermann et al., 2015; Tanenbaum et al., 2014; Zalatan et al., 2015). This system reportedly can function as a pioneer factor to target a silenced chromatic locus with high precision and promote downstream gene transcription (Polstein et al., 2015). With these features, the CRISPRa system provides an advantageous tool to precisely remodel endogenous chromatin loci for cellular reprogramming from one lineage to another lineage specific cell (Black et al., 2016; Chakraborty et al., 2014). But whether this system is able, and/or how this system can be put to work, to generate induced pluripotent stem cell with a full range of differentiation potential to cells of all lineages is unknown.

SUMMARY OF THE DISCLOSURE

This disclosure is predicated on the discovery herein that induced pluripotent stem cells (iPSCs) can be generated by targeting and remodeling selective endogenous gene loci in somatic cells and is directed, in part, to methods of generating iPSCs comprising: targeting at least one endogenous gene locus using at least one single guide RNA (sgRNA) in a non-iPSC and remodeling the selective endogenous gene locus in the non-iPSC using a CRISPR activation system and the at least one sgRNA to generate iPSCs. In some embodiments, the above method of generating iPSC further comprises contacting the non-iPSC cell undergoing reprogramming with small molecules comprising a TGFβR inhibitor, a GSK3 inhibitor, a MEK inhibitor and a ROCK inhibitor; and optionally contacting the generated iPSCs with small molecules comprising a GSK3 inhibitor, a MEK inhibitor and a ROCK inhibitor, but not a TGFβR inhibitor.

In some embodiments, the CRISPR activation system comprises a nuclease-deactivated Cas9 (dCas9) fused with at least one transcriptional activator. In other embodiments, the CRISPR activation system further comprises a tandem array of peptides that links dCas9 to the at least one transcriptional activator. In one embodiment, the tandem array of peptide is a SunTag array. In one embodiment, the at least one transcriptional activator is a tetramer of herpes simplex VP16 transcriptional activator domain (VP64). In one embodiment, the CRISPR activation system is dCas9-SunTag-VP64.

In other aspects, this disclosure provides a CRISPR activation system, comprising a dCas9, a SunTag array fused to the dCas9, and at least one acetyltransferase activity domain of p300 (p300core) attached to the SunTag array.

In other aspects, this disclosure provides methods of generating an iPSC using the CRISPR activation system comprising a dCas9, a SunTag array, and p300core.

In some embodiments, the at least one endogenous gene locus is Oct4, Sox2, Klf4, c-Myc, Lin28, Nanog, Nr5a2, Glis1, Cebpa, or any combination thereof.

In some embodiments, a single endogenous gene locus is targeted and remodeled. In some embodiments, the single endogenous gene locus is Oct4 or Sox2.

In some embodiments, the at least one sgRNA is an Oct4 promoter targeting sgRNA, an Oct4 enhancer targeting sgRNA, a Sox2 promoter targeting sgRNA, or a combination thereof. In some embodiment, the Oct4 promoter targeting sgRNA is selected from SEQ ID NOs: 1-6, 57, and 58. In some embodiment, the Oct4 enhancer targeting sgRNA is selected from SEQ ID NOs: 7-11. In some embodiment, the Sox2 gene targeting sgRNA is selected from SEQ ID NOs: 12-21, and 59.

In one embodiment, the at least one sgRNA is a Klf4 gene targeting sgRNA. In some embodiment, the Klf4 gene targeting sgRNA is selected from SEQ ID NOs: 22-31, and 60. In one embodiment, the at least one sgRNA is a c-Myc gene targeting sgRNA. In some embodiment, the c-Myc gene targeting sgRNA is selected from SEQ ID NOs: 32-41, and 61. In one embodiment, the at least one sgRNA is a Nr5a2 gene targeting sgRNA. In some embodiments, the Nr5a2 gene targeting sgRNA is selected from SEQ ID NOs: 42-45. In one embodiment, the at least one sgRNA is a Glis1 gene targeting sgRNA. In some embodiments, the Glis1 gene targeting sgRNA is selected from SEQ ID NOs: 46-50. In one embodiment, the at least one sgRNA is a Cebpa gene targeting sgRNA. In some embodiments, the Cebpa gene targeting sgRNA is selected from SEQ ID NOs: 51-56. In some embodiments, the sgRNA targets Lin28 promoter. In some embodiments, the sgRNA targeting Lin28 comprises SEQ ID NO: 62. In some embodiments, the sgRNA targets Nanog promoter. In some embodiments, the sgRNA targeting Nanog comprises SEQ ID NO: 63. In some embodiments, the sgRNA targets EEA-motif. In some embodiments, the sgRNA targeting EEA-motif comprises SEQ ID NO: 64.

In some embodiments, the non-iPSC is a somatic cell, for example, fibroblast, a skin cell, a cord blood cell, a peripheral blood cell, or a renal epithelial cell. In some embodiments, the non-iPSC is a mammalian cell. In other embodiments, the non-iPSC is a human cell.

DETAILED DESCRIPTION

Figure 1:
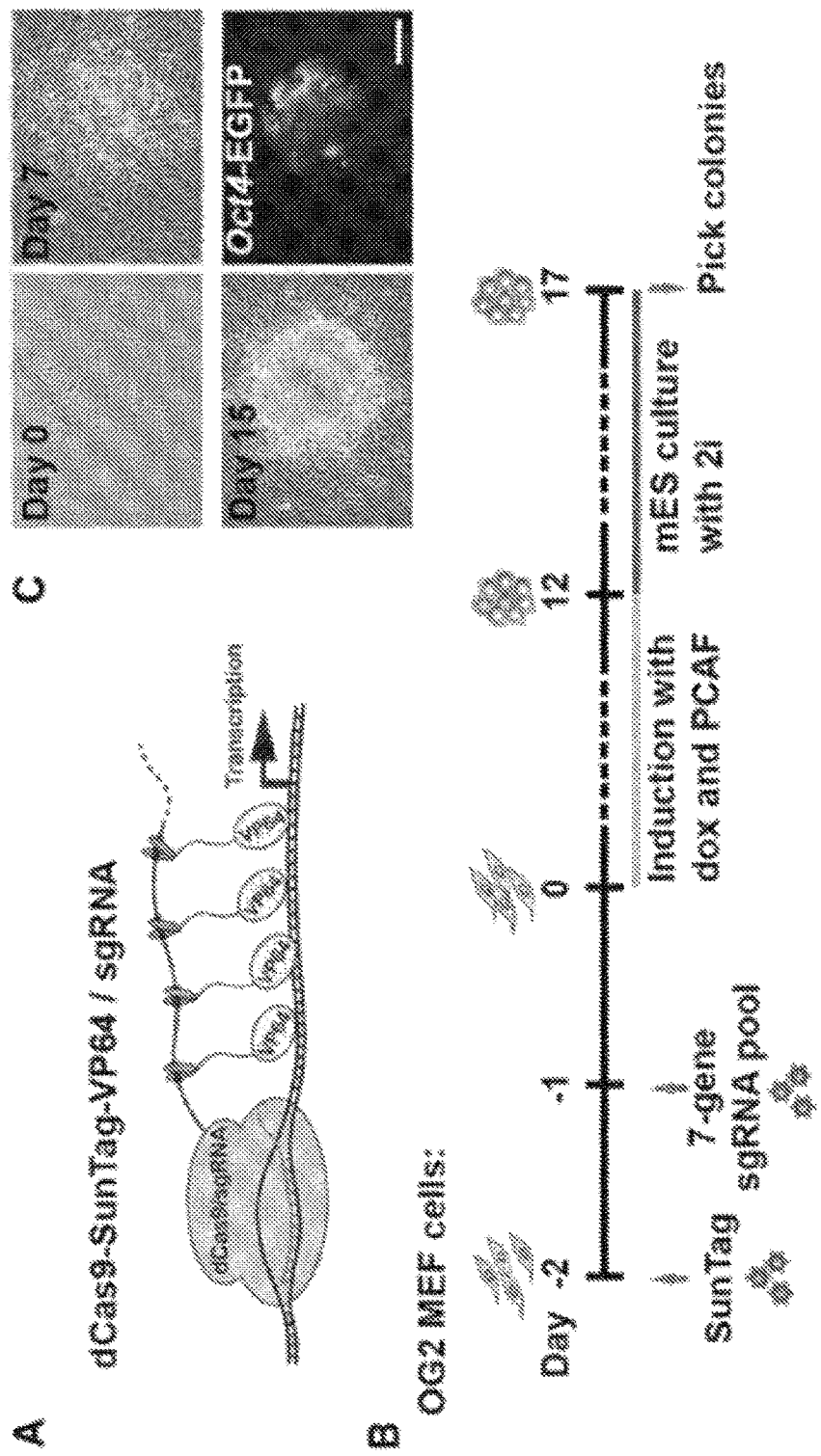
FIG. 1 demonstrates the establishment of pluripotency network in mouse embryonic fibroblasts (MEFs) by gene activation. (A) Scheme depicting the dCas9-SunTag-VP64 complex in gene activation. (B) Scheme depicting the reprogramming procedure in OG2 MEFs. (C) OG2 MEFs were reprogrammed to form EGFP-positive colonies. The morphology of MEFs on day 0 and reprogrammed colonies on days 7 and 15 were shown (scale bar, 200 µm). (D) Endogenous Oct4 and Sox2 transcription over 12 days. Data represent mean±SD (n=4). p values were determined by one-way ANOVA with Dunnett test. **p<0.01. (E) Colonies showing EGFP signal in situ and at passages 1 and 20 (scale bar, 200 µm). (F) Nanog, Sox2, and SSEA-1 staining in EGFP-positive colonies (scale bar, 200 µm). (G) Pluripotent gene expression in established CRISPR iPSCs and R1 mouse embryonic stem (R1 ES) cells.
Figure 1:
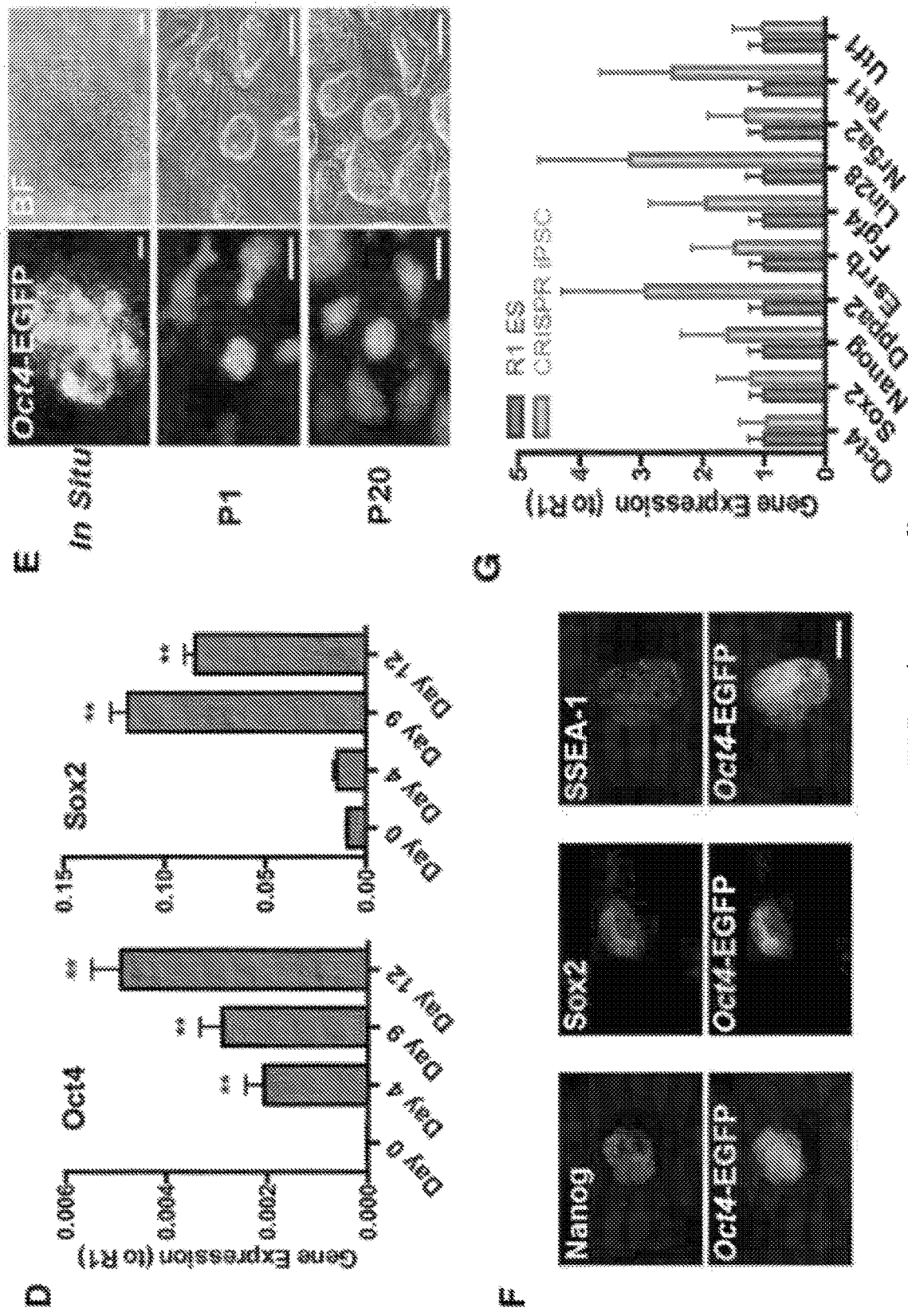

This disclosure relates to the generation of induced pluripotent stem cells (iPSCs) by targeting and remodeling endogenous gene loci with a CRISPR activation system.

It is to be understood that this disclosure is not limited to particular embodiments described, as such may vary. It is also to be understood that the terminology used herein is for the purpose of describing particular embodiments only, and is not intended to be limiting, since the scope of this disclosure will be limited only by the appended claims.

The detailed description of the disclosure is divided into various sections only for the reader's convenience and disclosure found in any section may be combined with that in another section. Although any methods and materials similar or equivalent to those described herein can also be used in the practice or testing of the present disclosure, the preferred methods and materials are now described. All publications mentioned herein are incorporated by reference to disclose and describe the methods and/or materials in connection with which the publications are cited.

I. Definitions

To facilitate the understanding of this disclosure, a number of terms are defined below. Unless defined otherwise, all technical and scientific terms used herein have the same meaning as commonly understood by one of ordinary skill in the art to which this invention belongs. Terms such as "a", "an" and "the" are not intended to refer to only a singular entity, but include the general class of which a specific example may be used for illustration.

As used herein, the term "generate" refers to the production and/or alteration of a biological composition (e.g., a cell) from its naturally occurring state through any manipulation including, but not limited to, altering the chromosomal structure, the nucleotide sequence of a polynucleotide (e.g., a DNA or an RNA), the amino acid sequence of a polypeptide (e.g., a protein), the transcription level of a gene, the epigenetic modifications of a chromosomal region, the transcription level of a protein, and the transcription level of an RNA.

As used herein, the terms "reprogramming" or "dedifferentiation" or "increasing cell potency" or "increasing developmental potency" refers to a method of increasing the potency of a cell or dedifferentiating the cell to a less differentiated state. For example, a cell that has an increased cell potency has more developmental plasticity (i.e., can differentiate into more cell types) compared to the same cell in the non-reprogrammed state. In other words, a reprogrammed cell is one that is in a less differentiated state than the same cell in a non-reprogrammed state.

The term "pluripotent" or "pluripotency" refers to the capacity of a cell to self-renew and to differentiate into multiple tissue or all lineage cell types in the body. For example, embryonic stem cells are a type of pluripotent stem cells that are able to form cells from each of the three germs layers, the ectoderm, the mesoderm, and the endoderm. Pluripotency is a continuum of developmental potencies ranging from the incompletely or partially pluripotent cell (e.g., an epiblast stem cell or EpiSC), which is unable to give rise to a complete organism to the more primitive, more pluripotent cell, which is able to give rise to a complete organism (e.g., an embryonic stem cell).

Pluripotency can be determined, in part, by assessing pluripotency characteristics of the cells. Pluripotency characteristics include, but are not limited to: (i) pluripotent stem cell morphology; (ii) the potential for unlimited self-renewal; (iii) expression of pluripotent stem cell markers including, but not limited to SSEA1 (mouse only), SSEA3/4, SSEA5, TRA1-60/81, TRA1-85, TRA2-54, GCTM-2, TG343, TG30, CD9, CD29, CD133/prominin, CD140a, CD56, CD73, CD90, CD105, OCT4, NANOG, SOX2, CD30 and/or CD50; (iv) ability to differentiate to all three somatic lineages (ectoderm, mesoderm and endoderm); (v) teratoma formation consisting of the three somatic lineages; and (vi) formation of embryoid bodies consisting of cells from the three somatic lineages.

Two types of pluripotency have previously been described: the "primed" or "metastable" state of pluripotency akin to the epiblast stem cells (EpiSC) of the late blastocyst, and the "Naïve" or "Ground" state of pluripotency akin to the inner cell mass of the early/preimplantation blastocyst. While both pluripotent states exhibit the characteristics as described above, the naïve or ground state further exhibits: (i) pre-inactivation or reactivation of the X-chromosome in female cells; (ii) improved clonality and survival during single-cell culturing; (iii) global reduction in DNA methylation; (iv) reduction of H3K27me3 repressive chromatin mark deposition on developmental regulatory gene promoters; and (v) reduced expression of differentiation markers relative to primed state pluripotent cells. Standard methodologies of cellular reprogramming in which exogenous pluripotency genes are introduced to a somatic cell, expressed, and then either silenced or removed from the resulting pluripotent cells are generally seen to have characteristics of the primed-state of pluripotency. Under standard pluripotent cell culture conditions such cells remain in the primed state unless the exogenous transgene expression is maintained, wherein characteristics of the ground-state are observed.

As used herein, the term "induced pluripotent stem cells" or, iPSCs, means that the stem cells are produced from differentiated adult, neonatal or fetal cells that have been induced or changed, i.e., artificially reprogrammed into cells having a less differentiated state; exhibiting characteristics of pluripotency, such as expression of certain stem cell genes and proteins, chromatin methylation patterns, embryoid body formation, teratoma formation, viable chimera formation; and capable of differentiating into tissues of all three germ or dermal layers: endoderm (e.g., interior stomach lining, gastrointestinal tract, the lungs), mesoderm (e.g., muscle, bone, blood, urogenital), or ectoderm (e.g., epidermal tissues and nervous system). The iPSCs produced do not refer to cells as they are found in nature.

As used herein, the term "pluripotent stem cell morphology" refers to the classical morphological features of an embryonic stem cell. Normal embryonic stem cell morphology is characterized by being round and small in shape, with a high nucleus-to-cytoplasm ratio, the notable presence of nucleoli, and typical inter-cell spacing.

As used herein, the term "non-iPSC" refers to any cell in a differentiated or partially differentiated state and is not an embryonic stem cell (ESC) or an iPSC. A non-iPSC can be from any non-germline tissue of the body including internal organs, skin, bones, blood, nervous tissue, and connective tissue.

As used herein, the "CRISPR/Cas system" refers to a system originated from bacteria for defense against foreign nucleic acid. CRISPR/Cas systems are found in a wide range of eubacterial and archaeal organisms and include type I, II, and III sub-types. CRISPR related nucleases are from families including cas, cpf, cse, csy, csn, csd, cst, csh, csa, csm, and cmr. Wild-type type II CRISPR/Cas systems utilize an RNA-mediated nuclease in complex with CRISPR RNA (crRNA), sometimes as well as transactivating crRNA (tracrRNA), to recognize and cleave foreign nucleic acid. Where both crRNA and the tracrRNA are needed, in the case of Cas9, for example, the crRNA and the tracrRNA can be engineered into a single-guide RNA (sgRNA) molecule that, when combined with Cas9, find and cleave DNA targets through complementary base pairing between the guide sequence within the sgRNA and the target DNA sequence. As used herein, the term "nuclease-deactivated Cas9" or "dCas9" refers to a modified Cas9 nuclease wherein the nuclease activity has been disabled by mutating residues in its catalytic RuvC and HNH domains. Disabling of the catalytic domains can convert Cas9 from an RNA-programmable nuclease into an RNA-programmable DNA recognition complex to deliver effectors or markers to specific target DNA sequences. Similar manipulation is applicable to other CRISPR related nucleases. As used herein, the term "CRISPR activation system" or "CRISPRa" refers to a CRISPR/Cas system that has been modified to upregulate gene transcription, in which the deactivated Cas nuclease is fused with a transcription activator, such as a herpes simplex VP16 transcriptional activator domain, a VP64 activator (an engineered tetramer of VP16), the activation domain of p65, a synergistic combination of multiple transcription activators, a scaffolding peptide to recruit multiple copies of transcription activators, or a histone acetyltransferase.

As used herein, the term "single guide polynucleotides" or "sgPNA" refers to a DNA, RNA, or DNA/RNA mixed sequence used in conjunction with a CRISPR/Cas system. The term "single guide RNA" or "sgRNA" refers to a RNA sequence used in conjunction with a CRISPR/Cas system. A sgPNA contains a binding site for a CRISPR related nuclease, including Cas9, and a guide sequence complementary to the desired target DNA sequence. Base pairing of the sgPNA with the target DNA sequence recruits CRISPR related nuclease to the DNA sequence.

As used herein, the term "targeting" refers to the process of identifying a nucleic acid sequence (i.e., a target) of any composition and/or length at a chromosomal locus including, but not limited to a gene, a promoter, an enhancer, an open reading frame, or any other chromosomal region. A sgRNA containing a guide sequence complementary to the pre-identified nucleic acid sequence is then designed and synthesized. In some embodiments, the sgRNA directs a CRISPR activation system to the vicinity of an endogenous gene locus having the pre-identified nucleic acid sequence based on complementary base pairing of the sgRNA to the pre-identified nucleic acid sequence.

As used herein, the term "remodel" or "remodeling" refers to any modification of the expression of a gene at the transcriptional level. Exemplary gene remodeling includes, but is not limited to, altering the chromatin structure of the gene, recruiting a transcription activator to the promoter of the gene, recruiting a transcription activator to the enhancer of the gene, and altering histone modification of the gene by specific enzymes (e.g., histone acetyltransferases).

II. Cells

This invention is predicated on the discovery that a non-iPSC, e.g., a somatic cell, can be reprogrammed to pluripotency by activating pluripotency-related genes, alone or in combination, at the endogenous loci through CRISPR activation.

The non-iPSCs of the present disclosure include any cell of the body that is not a stem cell, a germ cell, or an iPSC. Non-limiting examples of a non-iPSC is a somatic cell derived from any non-germline tissue of the body, including internal organs, skin, bones, blood, nervous tissue, and connective tissue. In some embodiments, the somatic cell is a fetal somatic cell. In some embodiments, the somatic cell is an adult somatic cell. In some embodiments, the non-iPSC is derived from a cell type that is easily accessible and requires minimal invasion, such as a fibroblast, a skin cell, a cord blood cell, a peripheral blood cell, and a renal epithelial cell.

The non-iPSCs of the present disclosure may be derived from a mammal, preferably a human, but include and are not limited to non-human primates, murines (i.e., mice and rats), canines, felines, equines, bovines, ovines, porcines, caprines, etc. In some embodiments, the non-iPSC is a human non-iPSC.

III. Targeting and Remodeling Endogenous Gene Loci

The present disclosure relates to targeting and remodeling an endogenous gene locus using the CRISPR activation system with at least one sgRNA targeting the desired gene locus. In some embodiments, the endogenous gene locus is a pluripotency-associated gene. In other embodiments, the endogenous gene locus is a non-pluripotency-associated gene. Non-limiting examples of a pluripotency-associated gene are Oct4, Sox2, Nanog, Klf4, c-Myc, Lin28, Nr5a2, Glis1, Cebpa, Esrrb, and Rex1. In some embodiments, the endogenous gene locus is Oct4 or Sox2. In some embodiments, the endogenous gene locus is a combination of Oct4, Sox2, Nanog, Klf4, c-Myc and Lin28.

In some embodiments, the method of generating an iPSC comprises using at least one sgRNA in conjunction with the CRISPR activation system that targets a pluripotency-associated gene. In some embodiments, the sgRNA targets a pluripotency-associated gene selected from the group consisting of Oct4, Sox2, Nanog, Klf4, c-Myc, Lin28, Nr5a2, Glis1, Cebpa, Esrrb, and Rex1. In some embodiments, the sgRNA targets a pluripotency-associated gene selected from the group consisting of Oct4, Sox2, Nanog, Klf4, c-Myc, Lin28, Nr5a2, Glis1, and Cebpa.

In some embodiments, the sgRNA targets the promoter region of a pluripotency-associated gene. In some embodiments, the sgRNA targets the enhancer region of a pluripotency-associated gene. In some embodiments, the sgRNA targets the promoter region of the Oct4 gene, the enhancer region of the Oct4 gene, the promoter region of the Sox2 gene, or a combination thereof.

In some embodiments, the sgRNA targets a region of the Oct4 promoter and/or enhancer region between about 1- and about 5000-bp upstream of the Oct4 transcription start site (TSS), between about 100-bp and about 4000-bp upstream of the Oct4 TSS, between about 200-bp and about 3000-bp upstream of the Oct4 TSS, between about 400-bp and about 4000-bp upstream of the Oct4 TSS, between about 500-bp and about 3000-bp upstream of the Oct4 TSS, between about 500-bp and about 3000-bp upstream of the Oct4 TSS, between about 600-bp and about 2000-bp upstream of the Oct4 TSS, or between about 700-bp and about 1000-bp upstream of the Oct4 TSS. In some embodiments, the sgRNA targets a region of the Oct4 promoter and/or enhancer region about 10-bp, about 20-bp, about 30-bp, about 40-bp, about 50-bp, about 60-bp, about 70-bp, about 80-bp, about 90-bp, about 100-bp, about 110-bp, about 120-bp, about 130-bp, about 140-bp, about 150-bp, about 160-bp, about 170-bp, about 180-bp, about 190-bp, about 200-bp, about 300-bp, about 400-bp, about 500-bp, about 600-bp, about 700-bp, about 800-bp, about 900-bp, about 1000-bp, about 1500-bp, about 2000-bp, 2500-bp, about 3000-bp, 3500-bp, about 4000-bp, 4500-bp, about 5000-bp upstream of the Oct4 transcription start site (TSS) or any region therebetween. In some embodiments, the any of the above sgRNA targets a region of the human Oct4 promoter and/or enhancer region.

In some embodiments, the sgRNA targets a region of the Sox2 promoter region between about 1- and about 5000-bp upstream of the Sox2 transcription start site (TSS), between about 100-bp and about 4000-bp upstream of the Sox2 TSS, between about 200-bp and about 3000-bp upstream of the Sox2 TSS, between about 400-bp and about 4000-bp upstream of the Sox2 TSS, between about 500-bp and about 3000-bp upstream of the Sox2 TSS, between about 500-bp and about 3000-bp upstream of the Sox2 TSS, between about 600-bp and about 2000-bp upstream of the Sox2 TSS, or between about 700-bp and about 1000-bp upstream of the Sox2 TSS. In some embodiments, the sgRNA targets a region of the Sox2 promoter region about 10-bp, about 20-bp, about 30-bp, about 40-bp, about 50-bp, about 60-bp, about 70-bp, about 80-bp, about 90-bp, about 100-bp, about 110-bp, about 120-bp, about 130-bp, about 140-bp, about 150-bp, about 160-bp, about 170-bp, about 180-bp, about 190-bp, about 200-bp, about 300-bp, about 400-bp, about 500-bp, about 600-bp, about 700-bp, about 800-bp, about 900-bp, about 1000-bp, about 1500-bp, about 2000-bp, 2500-bp, about 3000-bp, 3500-bp, about 4000-bp, 4500-bp, about 5000-bp upstream of the Sox2 transcription start site (TSS) or any region therebetween. In some embodiments, the any of the above sgRNA targets a region of the human Sox2 promoter and/or enhancer region.

In some embodiments, the sgRNA targets a region of the Nanog promoter and/or enhancer region between about 1- and about 5000-bp upstream of the Nanog transcription start site (TSS), between about 100-bp and about 4000-bp upstream of the Nanog TSS, between about 200-bp and about 3000-bp upstream of the Nanog TSS, between about 400-bp and about 4000-bp upstream of the Nanog TSS, between about 500-bp and about 3000-bp upstream of the Nanog TSS, between about 500-bp and about 3000-bp upstream of the Nanog TSS, between about 600-bp and about 2000-bp upstream of the Nanog TSS, or between about 700-bp and about 1000-bp upstream of the Nanog TSS. In some embodiments, the sgRNA targets a region of the Nanog promoter and/or enhancer region about 10-bp, about 20-bp, about 30-bp, about 40-bp, about 50-bp, about 60-bp, about 70-bp, about 80-bp, about 90-bp, about 100-bp, about 110-bp, about 120-bp, about 130-bp, about 140-bp, about 150-bp, about 160-bp, about 170-bp, about 180-bp, about 190-bp, about 200-bp, about 300-bp, about 400-bp, about 500-bp, about 600-bp, about 700-bp, about 800-bp, about 900-bp, about 1000-bp, about 1500-bp, about 2000-bp, 2500-bp, about 3000-bp, 3500-bp, about 4000-bp, 4500-bp, about 5000-bp upstream of the Nanog transcription start site (TSS) or any region therebetween. In some embodiments, the any of the above sgRNA targets a region of the human Nanog promoter and/or enhancer region.

In some embodiments, the sgRNA targets a region of the Klf4 promoter and/or enhancer region between about 1- and about 5000-bp upstream of the Klf4 transcription start site (TSS), between about 100-bp and about 4000-bp upstream of the Klf4 TSS, between about 200-bp and about 3000-bp upstream of the Klf4 TSS, between about 400-bp and about 4000-bp upstream of the Klf4 TSS, between about 500-bp and about 3000-bp upstream of the Klf4 TSS, between about 500-bp and about 3000-bp upstream of the Klf4 TSS, between about 600-bp and about 2000-bp upstream of the Klf4 TSS, or between about 700-bp and about 1000-bp upstream of the Klf4 TSS. In some embodiments, the sgRNA targets a region of the Klf4 promoter and/or enhancer region about 10-bp, about 20-bp, about 30-bp, about 40-bp, about 50-bp, about 60-bp, about 70-bp, about 80-bp, about 90-bp, about 100-bp, about 110-bp, about 120-bp, about 130-bp, about 140-bp, about 150-bp, about 160-bp, about 170-bp, about 180-bp, about 190-bp, about 200-bp, about 300-bp, about 400-bp, about 500-bp, about 600-bp, about 700-bp, about 800-bp, about 900-bp, about 1000-bp, about 1500-bp, about 2000-bp, 2500-bp, about 3000-bp, 3500-bp, about 4000-bp, 4500-bp, about 5000-bp upstream of the Klf4 transcription start site (TSS) or any region therebetween. In some embodiments, the any of the above sgRNA targets a region of the human Klf4 promoter and/or enhancer region.

In some embodiments, the sgRNA targets a region of the c-Myc promoter and/or enhancer region between about 1- and about 5000-bp upstream of the c-Myc transcription start site (TSS), between about 100-bp and about 4000-bp upstream of the c-Myc TSS, between about 200-bp and about 3000-bp upstream of the c-Myc TSS, between about 400-bp and about 4000-bp upstream of the c-Myc TSS, between about 500-bp and about 3000-bp upstream of the c-Myc TSS, between about 500-bp and about 3000-bp upstream of the c-Myc TSS, between about 600-bp and about 2000-bp upstream of the c-Myc TSS, or between about 700-bp and about 1000-bp upstream of the c-Myc TSS. In some embodiments, the sgRNA targets a region of the c-Myc promoter and/or enhancer region about 10-bp, about 20-bp, about 30-bp, about 40-bp, about 50-bp, about 60-bp, about 70-bp, about 80-bp, about 90-bp, about 100-bp, about 110-bp, about 120-bp, about 130-bp, about 140-bp, about 150-bp, about 160-bp, about 170-bp, about 180-bp, about 190-bp, about 200-bp, about 300-bp, about 400-bp, about 500-bp, about 600-bp, about 700-bp, about 800-bp, about 900-bp, about 1000-bp, about 1500-bp, about 2000-bp, 2500-bp, about 3000-bp, 3500-bp, about 4000-bp, 4500-bp, about 5000-bp upstream of the c-Myc transcription start site (TSS) or any region therebetween. In some embodiments, the any of the above sgRNA targets a region of the human c-Myc promoter and/or enhancer region.

In some embodiments, the sgRNA targets a region of the Nr5a2 promoter and/or enhancer region between about 1- and about 5000-bp upstream of the Nr5a2 transcription start site (TSS), between about 100-bp and about 4000-bp upstream of the Nr5a2 TSS, between about 200-bp and about 3000-bp upstream of the Nr5a2 TSS, between about 400-bp and about 4000-bp upstream of the Nr5a2 TSS, between about 500-bp and about 3000-bp upstream of the Nr5a2 TSS, between about 500-bp and about 3000-bp upstream of the Nr5a2 TSS, between about 600-bp and about 2000-bp upstream of the Nr5a2 TSS, or between about 700-bp and about 1000-bp upstream of the Nr5a2 TSS. In some embodiments, the sgRNA targets a region of the Nr5a2 promoter and/or enhancer region about 10-bp, about 20-bp, about 30-bp, about 40-bp, about 50-bp, about 60-bp, about 70-bp, about 80-bp, about 90-bp, about 100-bp, about 110-bp, about 120-bp, about 130-bp, about 140-bp, about 150-bp, about 160-bp, about 170-bp, about 180-bp, about 190-bp, about 200-bp, about 300-bp, about 400-bp, about 500-bp, about 600-bp, about 700-bp, about 800-bp, about 900-bp, about 1000-bp, about 1500-bp, about 2000-bp, 2500-bp, about 3000-bp, 3500-bp, about 4000-bp, 4500-bp, about 5000-bp upstream of the Nr5a2 transcription start site (TSS)

or any region therebetween. In some embodiments, the any of the above sgRNA targets a region of the human Nr5a2 promoter and/or enhancer region.

In some embodiments, the sgRNA targets a region of the Cebpa promoter and/or enhancer region between about 1- and about 5000-bp upstream of the Cebpa transcription start site (TSS), between about 100-bp and about 4000-bp upstream of the Cebpa TSS, between about 200-bp and about 3000-bp upstream of the Cebpa TSS, between about 400-bp and about 4000-bp upstream of the Cebpa TSS, between about 500-bp and about 3000-bp upstream of the Cebpa TSS, between about 500-bp and about 3000-bp upstream of the Cebpa TSS, between about 600-bp and about 2000-bp upstream of the Cebpa TSS, or between about 700-bp and about 1000-bp upstream of the Cebpa TSS. In some embodiments, the sgRNA targets a region of the Cebpa promoter and/or enhancer region about 10-bp, about 20-bp, about 30-bp, about 40-bp, about 50-bp, about 60-bp, about 70-bp, about 80-bp, about 90-bp, about 100-bp, about 110-bp, about 120-bp, about 130-bp, about 140-bp, about 150-bp, about 160-bp, about 170-bp, about 180-bp, about 190-bp, about 200-bp, about 300-bp, about 400-bp, about 500-bp, about 600-bp, about 700-bp, about 800-bp, about 900-bp, about 1000-bp, about 1500-bp, about 2000-bp, 2500-bp, about 3000-bp, 3500-bp, about 4000-bp, 4500-bp, about 5000-bp upstream of the Cebpa transcription start site (TSS) or any region therebetween. In some embodiments, the any of the above sgRNA targets a region of the human Cebpa promoter and/or enhancer region.

In some embodiments, the sgRNA targets a region of the Esrrb promoter and/or enhancer region between about 1- and about 5000-bp upstream of the Esrrb transcription start site (TSS), between about 100-bp and about 4000-bp upstream of the Esrrb TSS, between about 200-bp and about 3000-bp upstream of the Esrrb TSS, between about 400-bp and about 4000-bp upstream of the Esrrb TSS, between about 500-bp and about 3000-bp upstream of the Esrrb TSS, between about 500-bp and about 3000-bp upstream of the Esrrb TSS, between about 600-bp and about 2000-bp upstream of the Glis1 TSS, or between about 700-bp and about 1000-bp upstream of the Esrrb TSS. In some embodiments, the sgRNA targets a region of the Esrrb promoter and/or enhancer region about 10-bp, about 20-bp, about 30-bp, about 40-bp, about 50-bp, about 60-bp, about 70-bp, about 80-bp, about 90-bp, about 100-bp, about 110-bp, about 120-bp, about 130-bp, about 140-bp, about 150-bp, about 160-bp, about 170-bp, about 180-bp, about 190-bp, about 200-bp, about 300-bp, about 400-bp, about 500-bp, about 600-bp, about 700-bp, about 800-bp, about 900-bp, about 1000-bp, about 1500-bp, about 2000-bp, 2500-bp, about 3000-bp, 3500-bp, about 4000-bp, 4500-bp, about 5000-bp upstream of the Esrrb transcription start site (TSS) or any region therebetween. In some embodiments, the any of the above sgRNA targets a region of the human Esrrb promoter and/or enhancer region.

In some embodiments, the sgRNA targets a region of the Rex1 promoter and/or enhancer region between about 1- and about 5000-bp upstream of the Rex1 transcription start site (TSS), between about 100-bp and about 4000-bp upstream of the Rex1 TSS, between about 200-bp and about 3000-bp upstream of the Rex1 TSS, between about 400-bp and about 4000-bp upstream of the Rex1 TSS, between about 500-bp and about 3000-bp upstream of the Rex1 TSS, between about 500-bp and about 3000-bp upstream of the Rex1 TSS, between about 600-bp and about 2000-bp upstream of the Rex1 TSS, or between about 700-bp and about 1000-bp upstream of the Rex1 TSS. In some embodiments, the sgRNA targets a region of the Rex1 promoter and/or enhancer region about 10-bp, about 20-bp, about 30-bp, about 40-bp, about 50-bp, about 60-bp, about 70-bp, about 80-bp, about 90-bp, about 100-bp, about 110-bp, about 120-bp, about 130-bp, about 140-bp, about 150-bp, about 160-bp, about 170-bp, about 180-bp, about 190-bp, about 200-bp, about 300-bp, about 400-bp, about 500-bp, about 600-bp, about 700-bp, about 800-bp, about 900-bp, about 1000-bp, about 1500-bp, about 2000-bp, 2500-bp, about 3000-bp, 3500-bp, about 4000-bp, 4500-bp, about 5000-bp upstream of the Rex1 transcription start site (TSS) or any region therebetween.

In some embodiments, the Oct4 promoter targeting sgRNA is selected from SEQ ID NOs: 1-6, 57, and 58. In some embodiments, the Oct4 enhancer targeting sgRNA is selected from SEQ ID NOs: 7-11. In some embodiments, the Sox2 promoter targeting sgRNA is selected from SEQ ID NOs: 12-21, and 59. In some embodiments, the Klf4 gene targeting sgRNA is selected from SEQ ID NOs: 22-31, and 60. In other embodiments, the c-Myc gene targeting sgRNA is selected from SEQ ID NOs: 32-41 and 61. In other embodiments, the Nr5a2 gene targeting sgRNA is selected from SEQ ID NOs: 42-45. In other embodiments, the Glis1 gene targeting sgRNA is selected from SEQ ID NOs: 46-50. In other embodiments, the Cebpa gene targeting sgRNA is selected from SEQ ID NOs: 51-56. In other embodiments, the Lin28 gene targeting sgRNA comprises SEQ ID NO: 62. In other embodiments, the Nanog gene targeting sgRNA comprises SEQ ID NO: 63. In another embodiment, the EEA-motif targeting sgRNA comprises SEQ ID NO: 64, wherein EEA-motif is a regulatory region associated with transcription of pluripotency genes, including, but not limited to PRD-like homeodomain TR binding site.

IV. CRISPR Activation System

The present disclosure is predicated on the CRISPR activation system that originated from the bacterial CRISPR/Cas system. The CRISPR activation system comprises a type II Cas that has been deactivated of its nuclease activity and has been fused with an effector to regulate gene transcription. In some embodiments, dCas is fused with at least one transcription activator. In some embodiments, dCas is fused with a tandem array of peptides that functions as a scaffolding structure to link dCas with multiple transcriptional activators. In some embodiments, the tandem array of peptides is a SunTag array. In other embodiments, the transactivator is a tetramer of herpes simplex VP16 transcriptional activator domain (VP64). In one embodiment, the CRISPR activation system is dCas-SunTag-VP64, also known as the SunTag CRISPR activation system.

In some embodiments, the CRISPR activation system comprises a dCas9 fused with a SunTag array and at least one acetyltransferase activity domain of p300 (p300core) attached to the SunTag array. In other embodiments, the method of generating an iPSC comprises using the CRISPR activation system comprising dCas9, SunTag array, and p300core to modify the histone acetylation of an endogenous gene locus, thus regulating the transcription of the gene. It will be understood that other CRISPR activation systems and/or transactivators known to one of skill in the art can be used to generate iPSCs.

EXAMPLES

The following examples are intended to further illustrate certain embodiments of the disclosure. The examples are put forth so as to provide one of ordinary skill in the art and are not intended to limit its scope.

Example 1. Activation of Endogenous Oct4 and Sox2 with dCas9-SunTag-VP64

To determine whether and how remodeling of endogenous loci initiate reprogramming towards pluripotency, the SunTag CRISPR activation system was used to precisely remodel endogenous pluripotency gene loci in mouse embryonic fibroblasts (MEFs). dCas9-SunTag-VP64 was chosen for its enhanced chromatin-remodeling activity by recruiting multiple VP64 to one targeting site (FIG. 1A) (Tanenbaum et al., 2014). dCas9 expression was controlled by a Tet-On promoter. Oct4 and Sox2 loci were selected as targets because of their central roles in pluripotency induction and maintenance.

The MEFs were prepared from E13.5 mouse embryos. After embryo recovery, the head, limbs, and internal organs, especially the gonads, were removed under dissection microscope. The remaining bodies of the embryos was finely minced with two blades and digested in 0.05% Trypsin-EDTA for 15 minutes. MEF medium was then added to stop the trypsinization. Further dissociation of the tissues was performed by pipetting up and down for a few times. Cells were then collected by centrifugation and plated onto 15 cm dishes for expansion (P0). MEF cells were used before P3 for all tests and were cultured in DMEM supplemented with 10% FBS and non-essential amino acids.

sgRNAs were designed to target Oct4 and Sox2 promoters, as well as Oct4 enhancer. Besides the activation effect of sgRNAs, multiple factors were considered, regarding the genomic sequences targeted, including their proximity to but no overlapping with the binding sites of pluripotent factor and transcription machinery, histone H3K27 acetylation in pluripotent stem cells, and their potential to form promoter-enhancer loops mediated by the Mediator complex (FIGS. 5A-5C).

For the sgRNA constructs, 72-bp oligos, including specific sgRNA sequences, were synthesized for PCR amplification with primers sgRNA-F (SEQ ID NO: 173—GTATCCCTTGGAGAACCACCT) and sgRNA-R (SEQ ID NO: 174—TGCTGTTTCCAGCTTAGCTCT). The amplified fragments were purified and used for recombination reaction according to the Gibson Assembly Cloning Kit protocol (NEB) with the pSLQ1373 construct digested with BstXI and BlpI.

Figure 5:
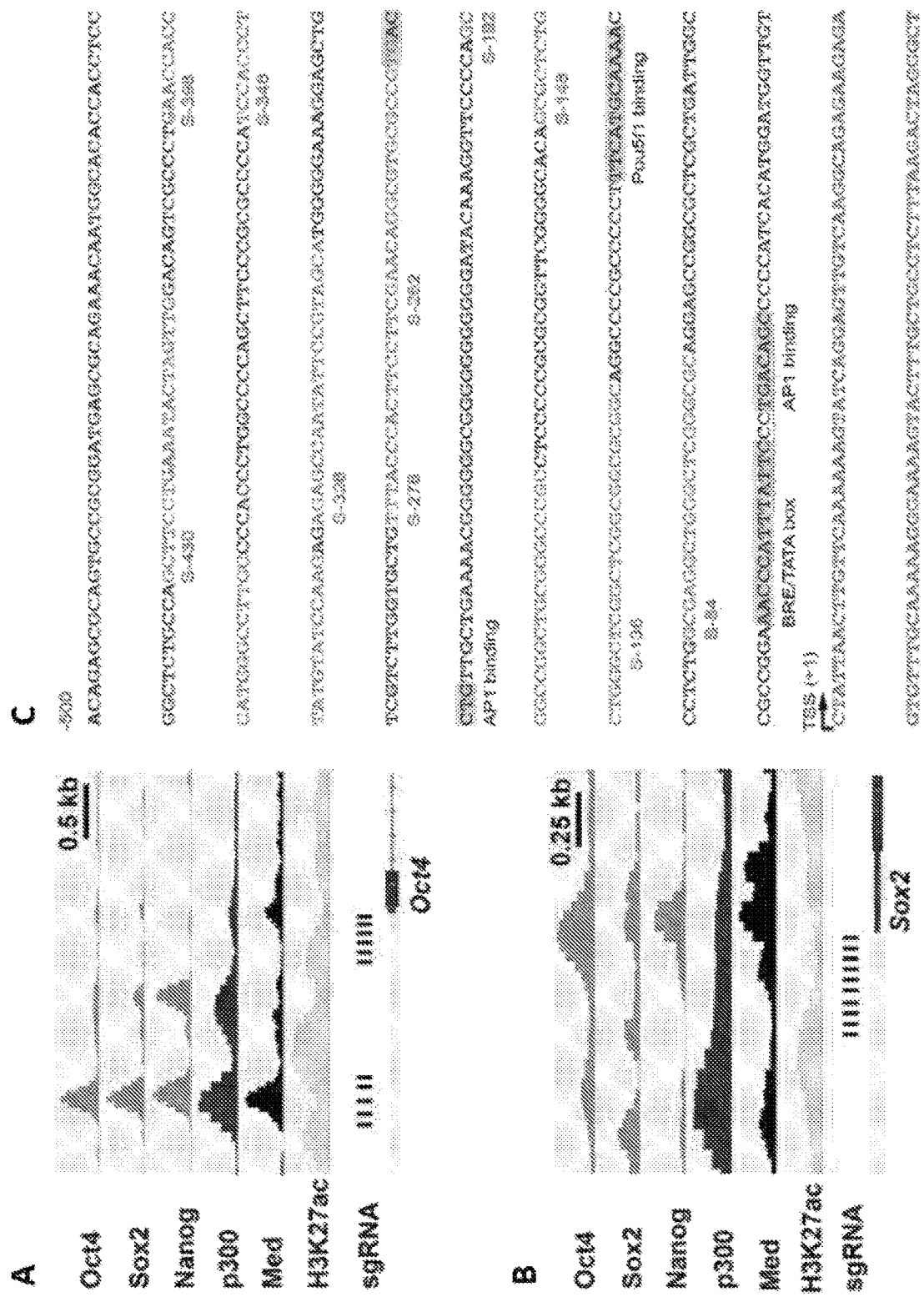
FIG. 5 demonstrates gene activation by the SunTag system in differentiating mouse ES cells and MEFs. (A), (B) Schemes depicting the sgRNA targeting sites for Oct4 promoter and enhancer (A) and Sox2 promoter (B) along with the binding peaks of transcription factors (Oct4, Sox2, Nanog), histone acetyltransferase p300, the Mediator complex, and the distributions of histone H3K27ac (Whyte et al., 2013). (C) Genomic DNA sequence of 500 bp upstream and 100 bp downstream of Sox2 transcription start site (SEQ ID NO: 175). sgRNAs (blue) and transcription factor (in shade) binding sites are highlighted. (D), (E) Transcriptional activation of Oct4, Sox2, Klf4, c-Myc, Nr5a2, Glis1, and Cebpa using sgRNAs in differentiating mouse ES cells. A schematic diagram depicting the experimental procedure (D) and fold transcriptional activation using each sgRNA (E) are shown. Gal4 sgRNA was used as a negative control. (F), (G) Transcriptional activation of Oct4 and Sox2 using sgRNAs in MEFs. The experimental procedure (F) and fold transcriptional activation using selected sgRNAs (G) are shown. Gal4 sgRNA was used as a negative control. sgRNAs targeting Oct4 promoter (Oct4 Pro) include O-71 and O-127, and sgRNAs targeting Oct4 enhancer (Oct4 Enh) include O-1965, O-2066, and O-2135. Sox2 promoter (Sox2 Pro) targeting sgRNAs includes S-84, S-136, and S-148. (H) Oct4 and Sox2 activation with the small molecule combination of Parnate, Chir99021, A83-01, and Forskolin (PCAF). Data in (E), (G), and (H) represent mean±SD (n=4). p values in (E) and (G) were determined by one-way ANOVA with Dunnett test, and p values in (H) were determined by unpaired t test. *p<0.05; **p<0.01; ns, non-significant.
Figure 5:
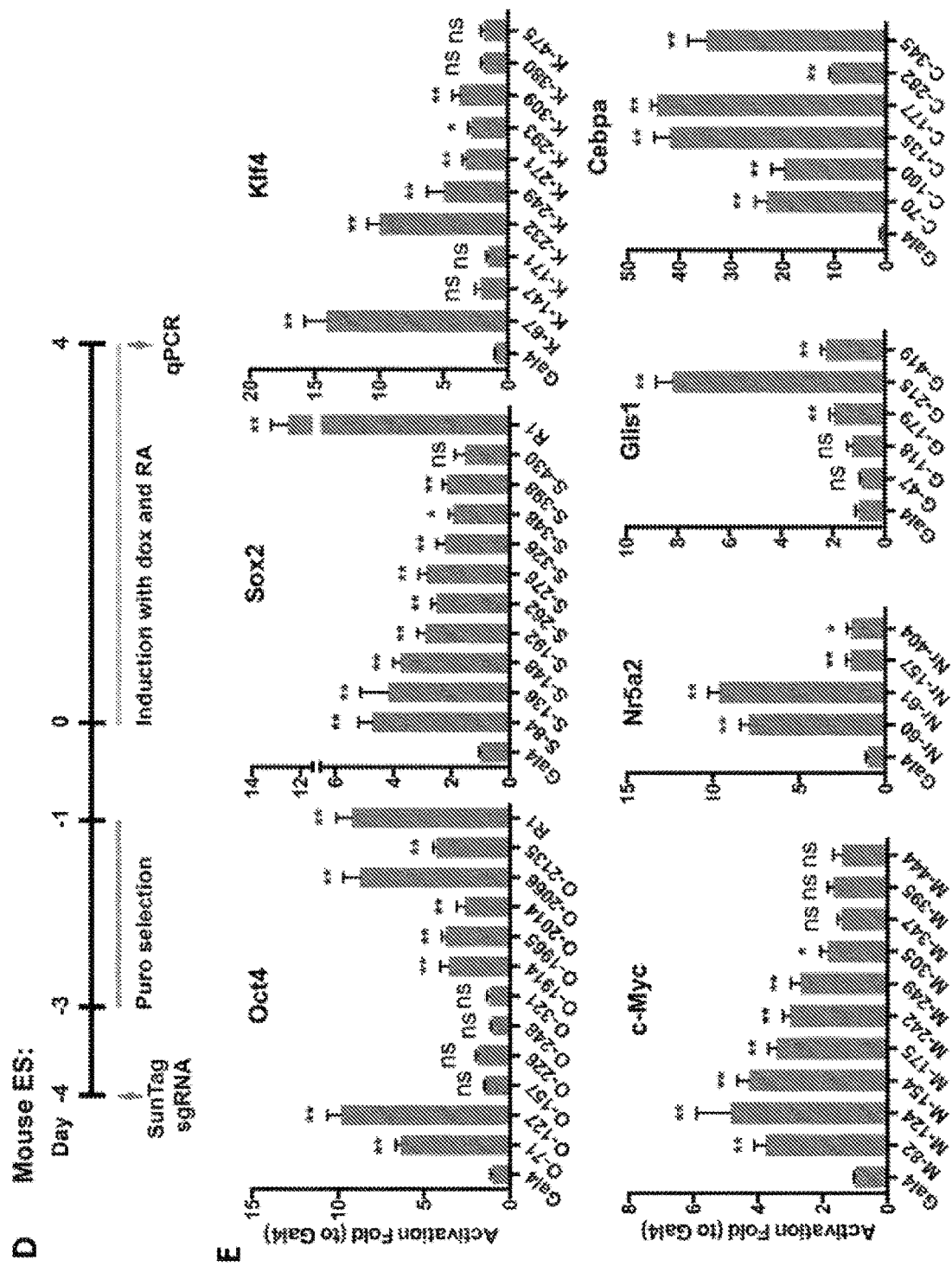
Figure 5:
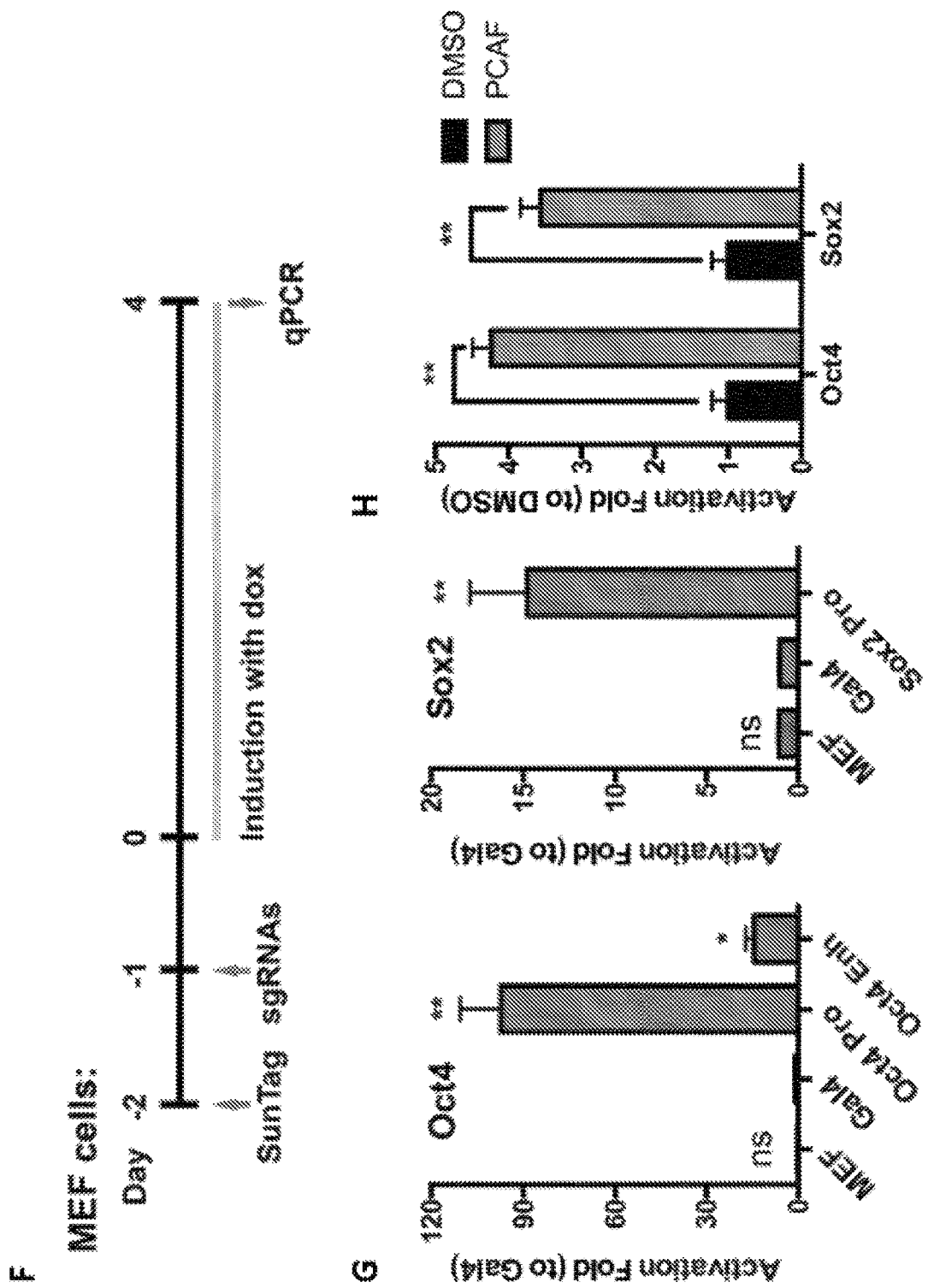

The level of transcriptional activation of target genes was examined with each designed Oct4 and Sox2 sgRNA delivered by lentivirus in differentiating mouse embryonic stem (ES) cells (FIG. 5D). HEK293T/17 cells (ATCC® CRL-11268) were cultured in DMEM supplemented 10% FBS and plated 1 day ahead to reach about 70% confluency for transfection, and VSV-G envelope expressing plasmid pMD2.G (Addgene, 12259) and psPAX2 (Addgene, 12260) were used for lentiviral packaging. Plasmids (1.8 μg) with the gene of interests were mixed with psPAX2 (1.35 μg) and pMD2.G (0.45 μg) for each well of six-well plates, and 10.8 μl FUGENE HD (Promega) was added for transfection. 5 hours later, the medium was refreshed. Supernatant containing the virus was harvested at 48 hours, passed through a 0.45-μM filter to remove the cell debris, and mixed with 1 volume of fresh medium for immediate use. For the SunTag system, lentiviruses for the three components (dCas9, VP64, and Tre3G) were packaged independently and mixed when used. SunTag transduction was performed in two rounds of lentiviral infection, the first round for the Suntag system (dCas9, VP64, and Tre3G) and the second round for sgRNAs. Media were refreshed after each infection.

Mouse ES cells were first transduced with dCas9-SunTag-VP64 system and sgRNAs. Because Oct4 and Sox2 are highly expressed in ES cells, the ES cells were induced to differentiate in MEF medium supplemented with 1 μM retinoic acid for 4 days to lower Oct4 and Sox2 expression. Meanwhile, the dCas9-SunTag-VP64 system was induced with doxycycline. Analysis of Oct4 expression showed that sgRNAs targeting a narrow promoter region close to the transcription start site (TSS) and a 200-bp region of distal enhancer can increase the transcription (FIG. 5E). As for Sox2 promoter, sgRNA activity showed a remarkable tendency for higher gene activation with sgRNAs closer to the TSS (FIG. 5E).

Selected sgRNAs and dCas9-SunTag-VP64 were also transduced into MEFs (FIG. 5F). MEF cells were incubated with the lentiviral supernatant in presence of 5 μg/ml polybrene (Millipore) for 8 hours or overnight. sgRNAs O-127 and O-71 targeting 127- and 71-bp upstream of Oct4 TSS were combined to target the promoter. Similarly, O-1965, O-2066, and O-2135 were combined to target Oct4 enhancer, and separately, S-84, S-136, and S-148 were combined to target Sox2 promoter. After 4 days of dCas9 induction by doxycycline, targeting Oct4 promoter led to about a 100-fold increase in Oct4 transcription, and targeting the enhancer resulted in modest activation (FIG. 5G). For Sox2 promoter, about 15-fold activation was detected (FIG. 5G). This suggests that, guided by specific sgRNAs, dCas9-SunTag-VP64 can activate silenced endogenous Oct4 and Sox2 genes in MEFs.

By detecting the blue fluorescent protein (BFP) from the sgRNA cassette, virus titration was performed in primary MEF cells, and the multiplicity of infection (MOI) can be calculated with the Poisson distribution (Arai et al., 1999):

$$P(k) = e^{-m} m^k / k!$$

wherein m is the MOI, k is the virus particle number, and P(k) is the fraction of cells infected by k virus particles. For the disclosed experiments, around 70% of the MEFs were positive for BFP, and the MOI was 1.20. Similarly, the fraction of cells infected by the indicated numbers of sgRNA virus particles are as follows:

| Number of virus particles | Fraction of Cells |
|---|---|
| 0 | 0.3012 |
| 1 | 0.3614 |
| 2 | 0.2169 |
| 3 | 0.0867 |
| 4 | 0.0260 |
| 5 | 0.0062 |
| ... | ... |

Example 2. Establishment of Pluripotency Network in MEFs by Gene Activation with dCas9-SunTag-VP64

It was next examined whether pluripotency network could be fully reactivated and established in MEFs. The SunTag reprogramming system was optimized in two ways. First, more genes were targeted by adding the corresponding sgRNAs. Klf4, c-Myc (Takahashi and Yamanaka, 2006), Nr5a2 (Heng et al., 2010), Glis1 (Maekawa et al., 2011), and Cebpa (Di Stefano et al., 2014) were selected. For each promoter, 4-10 sgRNAs were designed and tested in differentiating ES cells (FIG. 5E). 1-3 sgRNAs for each promoter were included in the previous Oct4/Sox2 sgRNA pool (see Table 1). Second, a small-molecule cocktail consisting of Parnate, Chir99021, A83-01, and Forskolin (PCAF) was added into the reprogramming medium. This chemical cocktail further increased Oct4 and Sox2 transcription by 3-4 times on day 4 (FIG. 5H).

TABLE 1 sgRNA sequences used in this disclosure*

| Target | Name | Sequence | SEQ ID |
|---|---|---|---|
| Oct4 promoter | O-321 | CAGCCCACTCAGCCATCCTC | 1 |
| | O-248 | ATCCGAGCAACTGGTTTGTG | 2 |
| | O-226 | GTGTCCGGTGACCCAAGGCA | 3 |
| | O-157 | GGACAGGACAACCCTTAGGA | 4 |
| | O-127 | AACCTCCGTCTGGAAGACAC | 5 |
| | O-71 | GGGTGGAGGAGCAGAGCTGT | 6 |
| Oct4 enhancer | O-2135 | AGACAGGACTGCTGGGCTGC | 7 |
| | O-2066 | GCCCTGGGAGGAACTGGGTG | 8 |
| | O-2014 | CCCAGGGAGGTTGAGAGTTC | 9 |
| | O-1965 | GCATGATAGCTCTGCCCTGG | 10 |
| | O-1914 | TAAGGAAGGGCTAGGACGAG | 11 |
| Sox2 promoter | S-430 | CAACTAGTATTTCAGGAAGC | 12 |
| | S-398 | GCAAGGCCCATGGGTGGTTC | 13 |
| | S-348 | CTTGGATACATAAGGGTGGA | 14 |
| | S-326 | AGAGCCAATATTCCGTAGCA | 15 |
| | S-276 | TTTACCCACTTCCTTCGAAC | 16 |
| | S-262 | CACGGCGCACGCCTGTTCGA | 17 |
| | S-192 | GCGGGCCCGCAGCCGGCGC | 18 |
| | S-148 | GCGCTCTGCTGGGCTCGGCT | 19 |
| | S-136 | GCTCGGCTCGGCGGCGCGGC | 20 |
| | S-84 | GCGAGGCTGGGCTCGGGCGC | 21 |
| Klf4 promoter | K-475 | GGACAAGCGCGTACGCGAGC | 22 |
| | K-380 | TGGGCTCGAAAGTCCTGCCA | 23 |
| | K-309 | CCACGCCGTACTCCCAGCGC | 24 |
| | K-293 | GGCGACGGCGGCTCCGGCGC | 25 |
| | K-271 | CACCGCCGCCGGCGTCAGCA | 26 |
| | K-249 | GCTCCAGCCCGCCAGCTGCC | 27 |
| | K-232 | GCCTGGCTGGCGTCAGGCC | 28 |
| | K-171 | TAAACAAACTCCGCGCACGT | 29 |
| | K-147 | GCTACCATGGCAACGCGCAG | 30 |
| | K-67 | CGCGCGCCGCCACAGGGAGG | 31 |
| c-Myc promoter | M-444 | GACGAACGAATGAGTTATCT | 32 |
| | M-395 | CCAGGCGTCTCTCTAAGGCT | 33 |
| | M-347 | ACACAATACGCCATGTACCC | 34 |
| | M-305 | TGCGGTGACTGATATACGCA | 35 |
| | M-249 | ACAACCGTACAGAAAGGGAA | 36 |
| | M-242 | TAGTCCTTTCCCTTTCTGTA | 37 |
| | M-175 | CGCTATTACTGTTTACACCC | 38 |
| | M-154 | CAGCCCAGTACTCCGGCTCC | 39 |
| | M-124 | GGCTCCTCCTCCTCTTTCCC | 40 |
| | M-82 | CGAGTTCCCAAAGCAGAGGG | 41 |
| Nr5a2 promoter | Nr-404 | CCGCCCTCTCACGGAAGCGG | 42 |
| | Nr-157 | GGGCGTGGAGCCCAGGAAGG | 43 |
| | Nr-61 | GATGGAATGTTCAAGTGGGA | 44 |
| | Nr-60 | TCCCACTTGAACATTCCATC | 45 |
| Glis1 promoter | G-419 | GGGAGGAGCAGAATCCCGCC | 46 |
| | G-215 | GGGCTGCCGGACCAAGCCAA | 47 |
| | G-179 | GAGCGGCTGTGGGCAGCAGC | 48 |
| | G-118 | GGCCGTGGCGGTGGCGGCGG | 49 |
| | G-47 | GCCGCGGGCGCAGCGGCTCG | 50 |
| Cebpa | C-345 | GCTCCCGGGCTCCCTAGTGT | 51 |
| | C-282 | CACACACGTGGTCCGTGGTT | 52 |
| | C-177 | GTGCTAGTGGAGAGAGATCG | 53 |
| | C-135 | GGAAAGTCACAGGAGAAGGC | 54 |
| | C-100 | GCCAGTAGGATGGTGCCTGC | 55 |
| | C-70 | CGAGACCCGTTTGGACACCA | 56 |

*sgRNAs in the 18-sgRNA pool are in bold

To monitor the reactivation of pluripotency network, MEF cells from OG2 mice (B6; CBA-Tg(Pou5f1-EGFP) 2Mnn/J, Jackson Laboratory) derived at E13.5 were used. OG2 MEFs harbor a stable Oct4-EGFP reporter and exhibit intense EGFP signal when endogenous Oct4 is actively transcribed (Szabo et al., 2002). MEF cells were seeded onto gelatin-coated plates at the density of 10,000 cells/cm$^2$ 24 hours before transduction. After transduction of dCas9-SunTag-VP64 and the sgRNA pool (18 sgRNAs in total, see Table 1), cells were allowed to recover in MEF medium for 24 hours. To start reprogramming, the MEF medium was changed to the reprogramming medium (ES medium supplemented with 10 µM Parnate, 3 µM Chir99021, 1 µM A83-01, and 10 µM Forskolin) supplemented with 1 µg/ml doxycycline. This was denoted as day 0 (FIG. 1B). On day 3, cells were treated with 1 mg/ml collagenase B (Roche) for 20 minutes and then 0.05% Trypsin for 5 minutes at 37° C., replated onto new wells (30,000 cells/cm$^2$), and further cultured until the end of reprogramming. Starting on day 4, transcription of Oct4 and Sox2 became more and more robust (FIG. 1D). By day 7, reprogramming clusters appeared, and after 2 weeks, EGFP-positive colonies were visible (FIG. 1C). Those colonies were also positive for Nanog, Sox2, and SSEA-1 (FIG. 1F). During the entire process, media were refreshed every other day for the first 12 days. After that, normal ES medium was used and changed every day, and EGFP-positive colonies were usually ready for iPSC derivation between days 16 and 18.

Then, EGFP-positive colonies were expanded on feeder cells to generate CRISPR iPSC lines. For iPSC derivation, the reprogramming cultures were incubated with 1 mg/ml collagenase B (Roche) for 20 minutes at 37° C. Single colonies were picked up under microscope and digested in 0.05% trypsin for 5-10 minutes for single-cell suspensions. Cells were then seeded on feeders in normal ES medium, and these cells are considered as P0 iPSCs. The CRISPR iPSCs formed typical mouse ES-like domed colonies with a strong EGFP signal (FIG. 1E). A panel of pluripotency genes, including Oct4, Sox2, Nanog, Esrrb, Nr5a2, and Utf1, was highly expressed (FIG. 1G). These cells can be passaged for more than 20 passages without any sign of losing EGFP signal or ES morphology (FIG. 1E). These data demonstrate that pluripotency has been established in these CRISPR iPSCs.

All iPSC lines were maintained on feeders in KO-DMEM (Invitrogen) with 5% ES-FBS (Invitrogen) and 15% KO-serum replacement (Invitrogen), 1% GlutaMAX™ (Invitrogen), 1% nonessential amino acids (Invitrogen), 55 µM 2-mercaptoethanol (Sigma), 10 ng/ml leukemia inhibitory factor (Stemgent), 3 µM CHIR99021, and 1 µM PD0325901.

Example 3. Single-Locus Targeting of Sox2 Gene to Establish CRISPR iPSCs

To identify the essential loci required for CRISPR iPSC generation, sgRNA targeting each individual locus was removed one by one from the pool. In this 18-sgRNA pool, removal of sgRNAs targeting Oct4, Sox2, or Glis1 promoter or Oct4 enhancer led to a sharp decrease in the number of EGFP-positive colonies (FIG. 6A), indicating potential roles for these loci in pluripotency induction.

Figure 6:
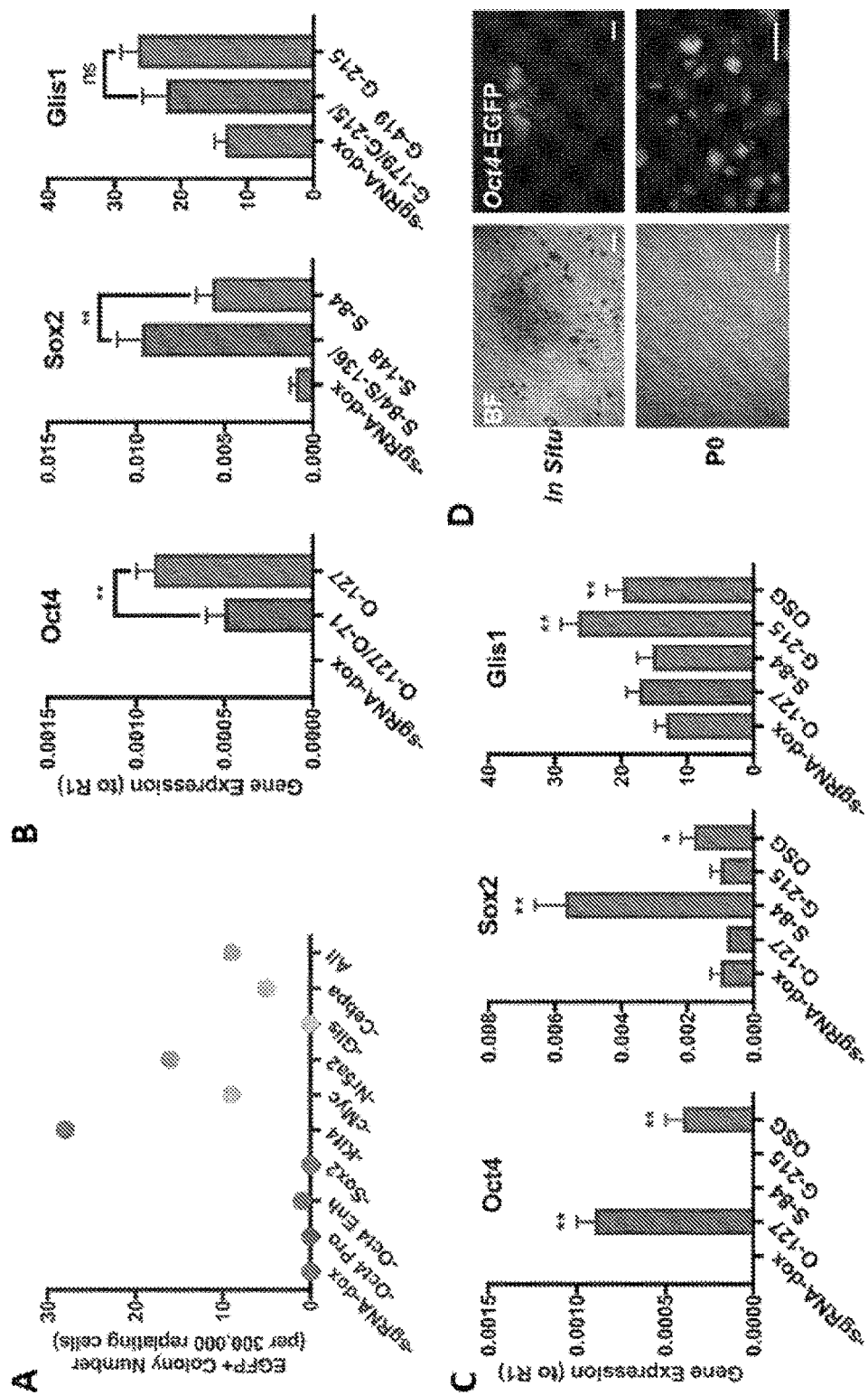
FIG. 6 demonstrates activation of Sox2 gene is sufficient to generate iPSCs in MEFs. (A) Numbers of EGFP-positive colonies when sgRNAs targeting the indicated genes were removed from the sgRNA pool. (B) Comparison of activation using one sgRNA and multiple sgRNAs for Oct4, Sox2, and Glis1 on day 3. (C) Transcriptional activation of Oct4, Sox2, and Glis1 using O-127, S-84, G-215, or all (OSG) on day 3. (D) Morphology of EGFP-positive colonies in situ and P0 iPSCs from targeting Oct4, Sox2, and Glis1 promoters together (scale bar, 200 μm). (E) Nanog, Sox2, and SSEA-1 staining of EGFP-positive colonies from targeting Oct4, Sox2, and Glis1 promoters together (scale bar: 200 μm). (F) Numbers of EGFP-positive colonies generated from targeting Oct4, Sox2, and Glis1 promoters. Three independent experiments are shown. (G) Examination of off-target effects of S-84 sgRNA. Transcription of the top 10 predicted targets were examined. Data in (B) and (C) represent mean±SD (n=4). p values were determined by unpaired t test. **p<0.01; *p<0.05; ns, non-significant.
Figure 6:
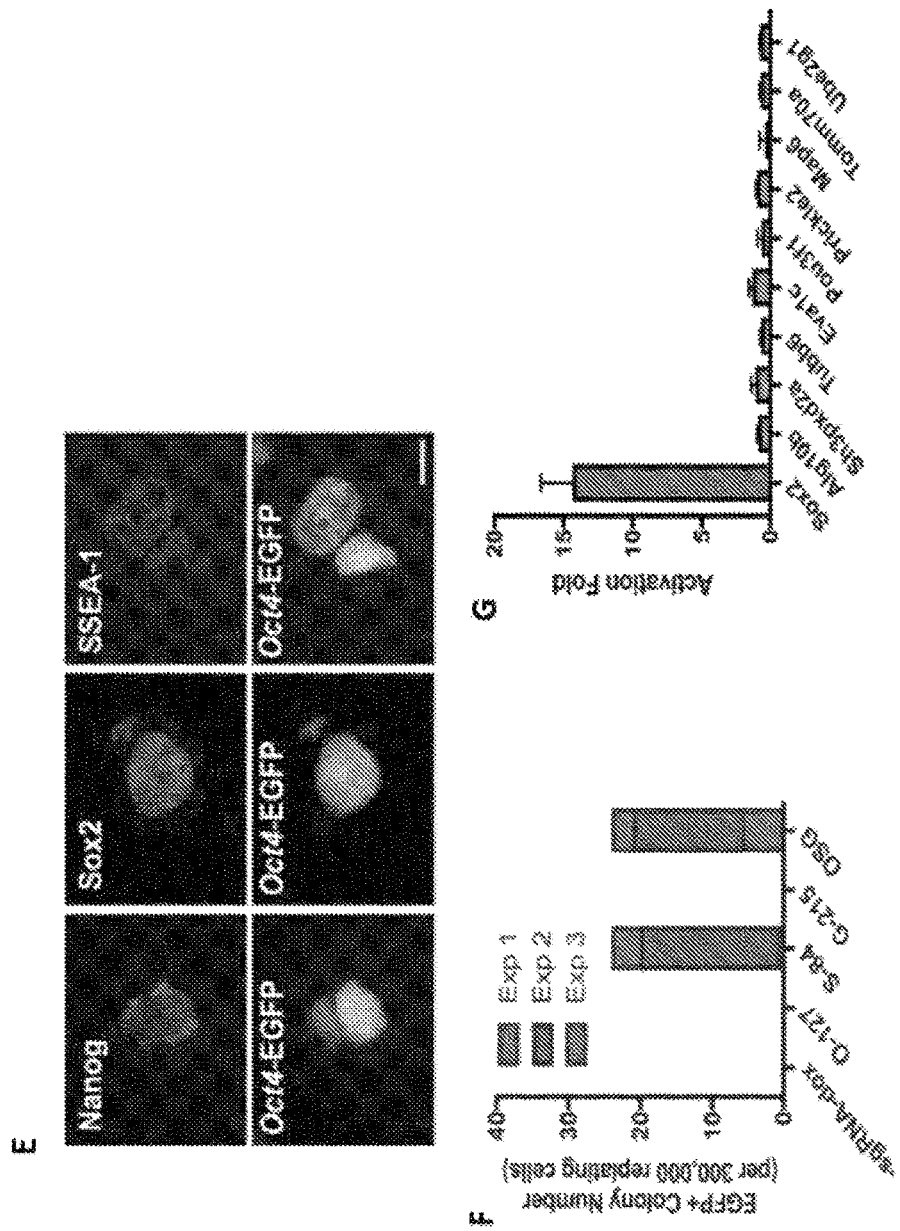

Next, it was determined whether the targeting of Oct4, Sox2, and Glis1 promoters together was sufficient to generate iPSCs. Since single sgRNA targeting each gene could achieve 60% to even 180% of gene activation compared to the combination of two- or three-sgRNAs targeting the same gene (FIG. 6B), one sgRNA was selected to target the promoter of each gene, O-127 for Oct4, S-84 for Sox2, and G-215 for Glis1. This approach simplified the reprogramming system and potentially decreased off-target effect. The combination of OSG (O-127, S-84, and G-215) could activate the three genes properly (FIG. 6C). After 2 weeks, EGFP-positive colonies were observed, and iPSC lines could be established (FIGS. 6D and 6E).

Figure 2:
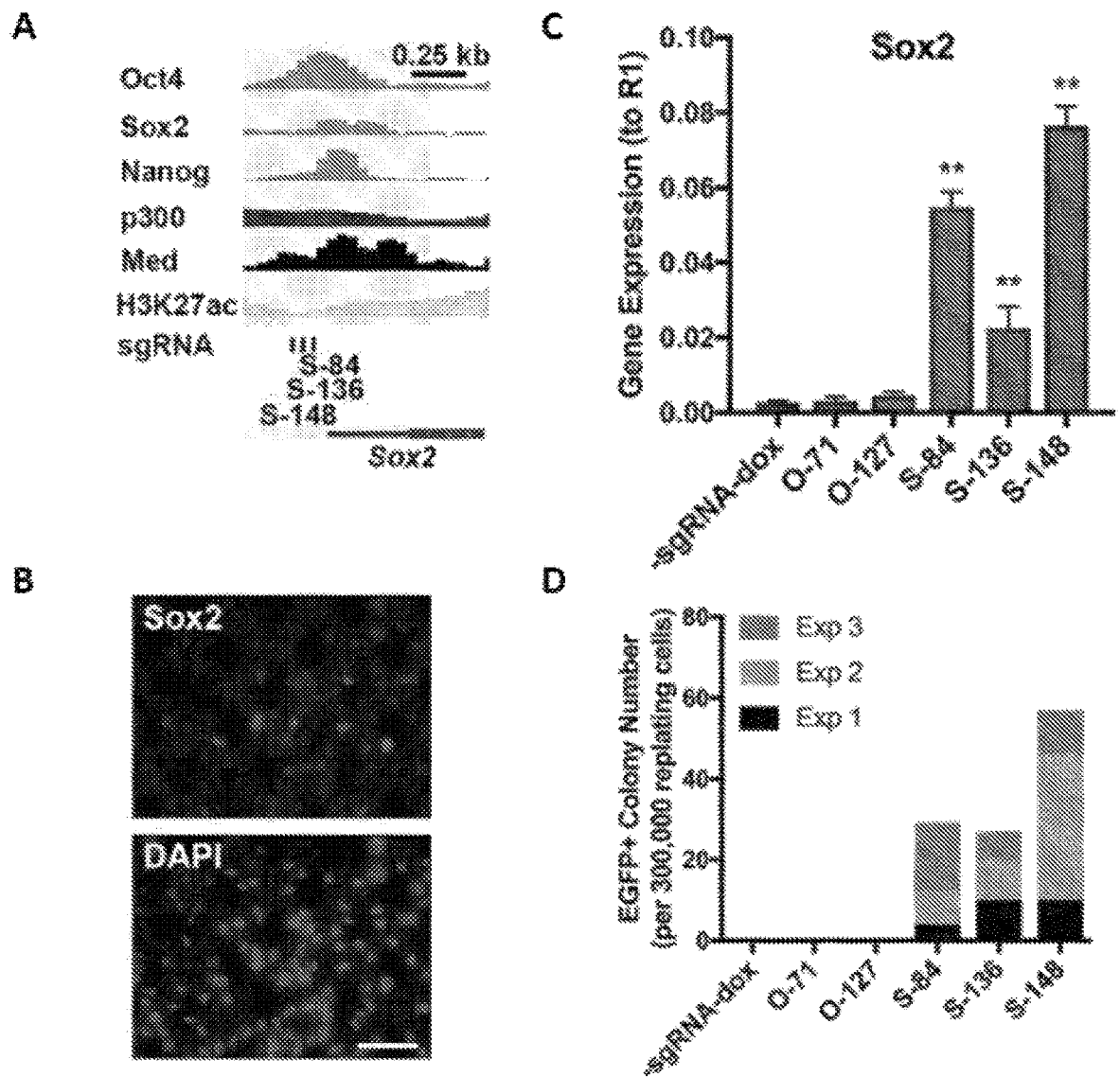
FIG. 2 demonstrates the activation of Sox2 gene is sufficient to generate iPSCs in MEFs. (A) Scheme depicting the sgRNA targeting sites for Sox2 promoter along with the binding peaks of transcription factors (Oct4, Sox2, Nanog), histone acetyltransferase p300, the Mediator complex, and the distributions of histone H3K27ac (Whyte et al., 2013). (B) Detection of Sox2 protein by immunofluorescent staining on day 4 (scale bar: 100 µm). (C) Sox2 activation in the presence of indicated sgRNAs. O-71 and O-127 target Oct4 promoter, while S-84, S-136, and S-148 target Sox2 promoter. Data represent mean±SD (n=4). p values were determined by unpaired t test. **p<0.01. (D) Numbers of colonies generated from targeting Oct4 or Sox2 promoter with sgRNA O-71, O-127, S-84, S-136, or S-148. Three independent experiments are shown. (E) Generation of EGFP-positive colonies in situ and iPSC line by activating Sox2 gene with S-84 (scale bar, 200 µm). (F) Nanog, Sox2, and SSEA-1 staining in EGFP-positive colonies generated with S-84 (scale bar, 200 µm). (G) Comparison of pluripotency gene expression in S-17 cell line and R1 ES cells. (H) Male karyotype of S-17 line. (I)-(K) Characterization of the pluripotent S-17 line in vivo. Chimeric mice were generated with S-17 cells (J), and these cells contributed to the gonadal tissue represented by intense EGFP signal (I) and were competent for germline transmission (K).
Figure 2:
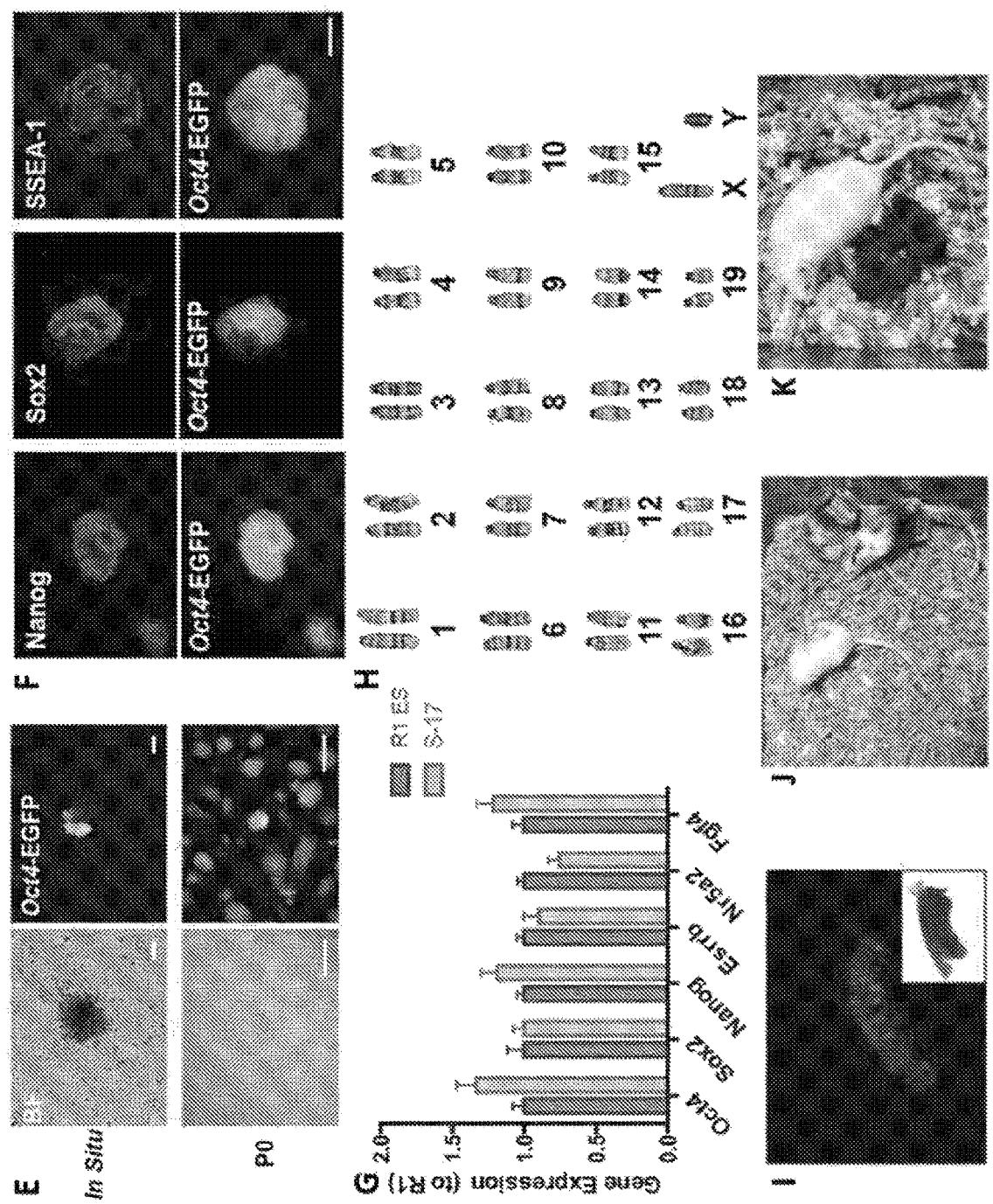

During OSG reprogramming, it was surprisingly noticed that EGFP-positive colonies appeared when S-84 alone was used (FIG. 6F), suggesting that targeting Sox2 promoter alone might be sufficient for pluripotency induction. To rule out the possibility of any off-target effect of S-84, the top 10 predicted targets of S-84 were examined. The off-targets of sgRNAs were predicted by the CCTop-CRISPR/Cas9 target online predictor (Stemmer et al., 2015). For each prediction, the core sequence was set at 12 bp. The maximum mismatches of core sequence were 2 bp, and the maximum mismatch of all mismatches was 4 bp. For S-84, only the Sox2 gene was significantly activated (FIG. 6G). Sox2 protein was also detected on day 4 (FIG. 2B). Additionally, the reprogramming procedure was repeated with another two Sox2-targeting sgRNAs, S-136 and S-148 (FIG. 2A). These two sgRNAs individually activated endogenous Sox2 transcription (FIG. 2C), and EGFP-positive colonies were obtained (FIG. 2D).

The authenticity of the pluripotency in these iPSCs was then examined. Within these EGFP-positive colonies, Nanog and SSEA-1 proteins were also detected, and CRISPR iPSC lines were established (FIGS. 2E and 2F). For line S-17, expression of key pluripotent factors was similar to that in R1 mouse ES (R1 ES) cells (FIG. 2G). Karyotyping of iPSC lines was performed at Cell Line Genetics and Giemsa binding was analyzed. The generated iPSCs were also karyotypically normal (FIG. 2H).

A more stringent assay for pluripotency was performed, where S-17 cells were injected into the blastocysts of B6 Albino (B6(Cg)-Tyr$^{c-2J}$/J, Jackson Labs) background. EGFP-positive cells were found in the gonadal regions of 71.4% (5 out of 7) E13.5 embryos (FIG. 2I). Live-born chimeras were generated (FIG. 2J) at a rate of 46.2% (6 out of 13). More importantly, B6 Albino female mice (6 weeks) were used to mate with the chimeric mice (4-8 weeks) for germline transmission tests, and the S-17 cells were also germline competent (FIG. 2K). These data concluded that single-locus targeting of Sox2 promoter by single sgRNA was sufficient to reprogram MEFs into authentic pluripotent stem cells.

R1 ES cells were maintained on feeders in KO-DMEM (Invitrogen) with 5% ES-FBS (Invitrogen) and 15% KO-serum replacement (Invitrogen), 1% GlutaMAX™ (Invitrogen), 1% nonessential amino acids (Invitrogen), 55 µM 2-mercaptoethanol (Sigma), 10 ng/ml leukemia inhibitory factor (Stemgent), 3 µM CHIR99021, and 1 µM PD0325901. For microinjection, iPSCs were maintained under feeder-free N2B27 condition (50% DMEM/F12, 50% Neurobasal Medium, 0.5% N2 medium, 1% B27 medium, 0.1 mM 2-mercaptoethanol, 10 ng/ml leukemia inhibitory factor, 25 µg/ml BSA, 3 µM CHIR99021, and 1 µM PD0325901). On the day of injection, cells were suspended in Blastocyst Injection Medium (25 mM HEPES-buffered DMEM plus 10% FBS, pH 7.4).

For chimeric mouse generation and germline transmission test, super-ovulated 4 weeks old female B6(Cg)-Tyr$^{c-2J}$/J (B6-albino) mice (Jackson Laboratory) were mated to B6(Cg)-Tyr$^{c-2J}$/J males for blastocyst preparation. Morulae (2.5 d post-coitum) were collected and cultured overnight in KSOM medium (Millipore) at 37° C. in 5% $CO_2$. The next morning, the blastocysts were ready for iPSC injection, and approximately 10-20 cells were injected for each blastocyst. Injected blastocysts were cultured in KSOM medium at 37° C. in 5% $CO_2$ for 1-2 hours and then implanted into uteri of 2.5 days post-coitum pseudopregnant CD1 female mice (Charles River, Stock #022). Chimeric mice can be identified by the mosaic coat color. The male chimeric mice are further mated with female B6(Cg)-Tyr$^{c-2J}$/J mice, and pups with black coat color are considered as successful germline transmission. For gonadal contribution, the injected embryos were recovered 10 days (E13.5) after implantation. The gonadal regions of each embryo were collected and visualized under microscope for EGFP signal. All animal procedures were approved by the Institutional Animal Care and Use Committee at the University of California, San Francisco.

Figure 7:
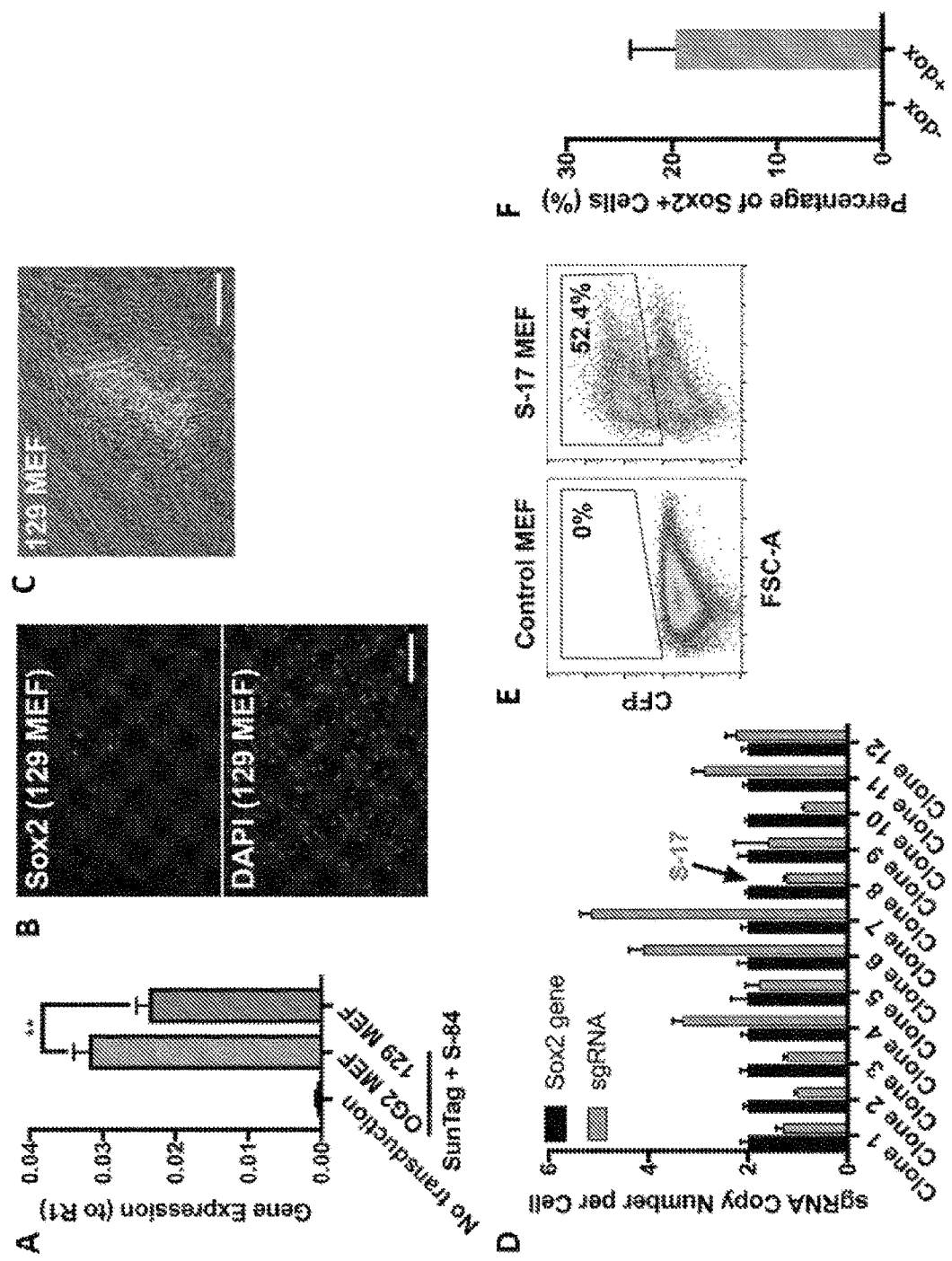
FIG. 7 demonstrates remodeling of Sox2 promoter triggers reprogramming towards pluripotency in MEFs. (A) Comparison of Sox2 activation with S-84 in OG2 and 129 MEFs. Data represent mean±SD (n=4). p value was determined by unpaired t test. **p<0.01. (B) Staining of Sox2 protein in 129 MEFs on day 4 (scale bar: 200 μm). (C) Generation of reprogrammed colonies in 129 MEFs (scale bar: 200 μm). (D) Copy number determination of the sgRNA cassette in 12 established CRISPR iPSC lines. Clone 8 is an S-17 line as indicated. (E) Flow cytometry examination of BFP in S-17 MEFs. (F) Percentage of Sox2-positive cells on day 4 with or without doxycycline for S-17 MEF reprogramming. (G) Examination of off-target effects of S-84 sgRNA in S-17 MEF reprogramming. Transcription of the top 10 predicted targets were examined by qPCR. (H) Coefficient of variation (CV) comparison of reprogramming efficiencies of lentiviral SunTag and S-17 MEFs. (I) Comparison of reprogramming efficiencies with or without PCAF cocktail. (J) Histone H3K27 acetylation levels at Sox2 promoter on day 4 when pluripotent genes were overexpressed (OE). Three conditions were tested: Oct4 alone, Sox2 alone, and OSK (Oct4, Sox2, and Klf4), and mCherry overexpression (mCh OE) was used as a negative control. (K) Coefficient of variation (CV) comparison of reprogramming efficiencies of OSK overexpression and S-17 MEFs. (L) S-17 TTFs were reprogrammable. Morphology of S-17 TTFs on day 0 and reprogrammed colonies on days 7 and 14 are shown with activation of Oct4-EGFP (scale bar: 200 μm).
Figure 7:
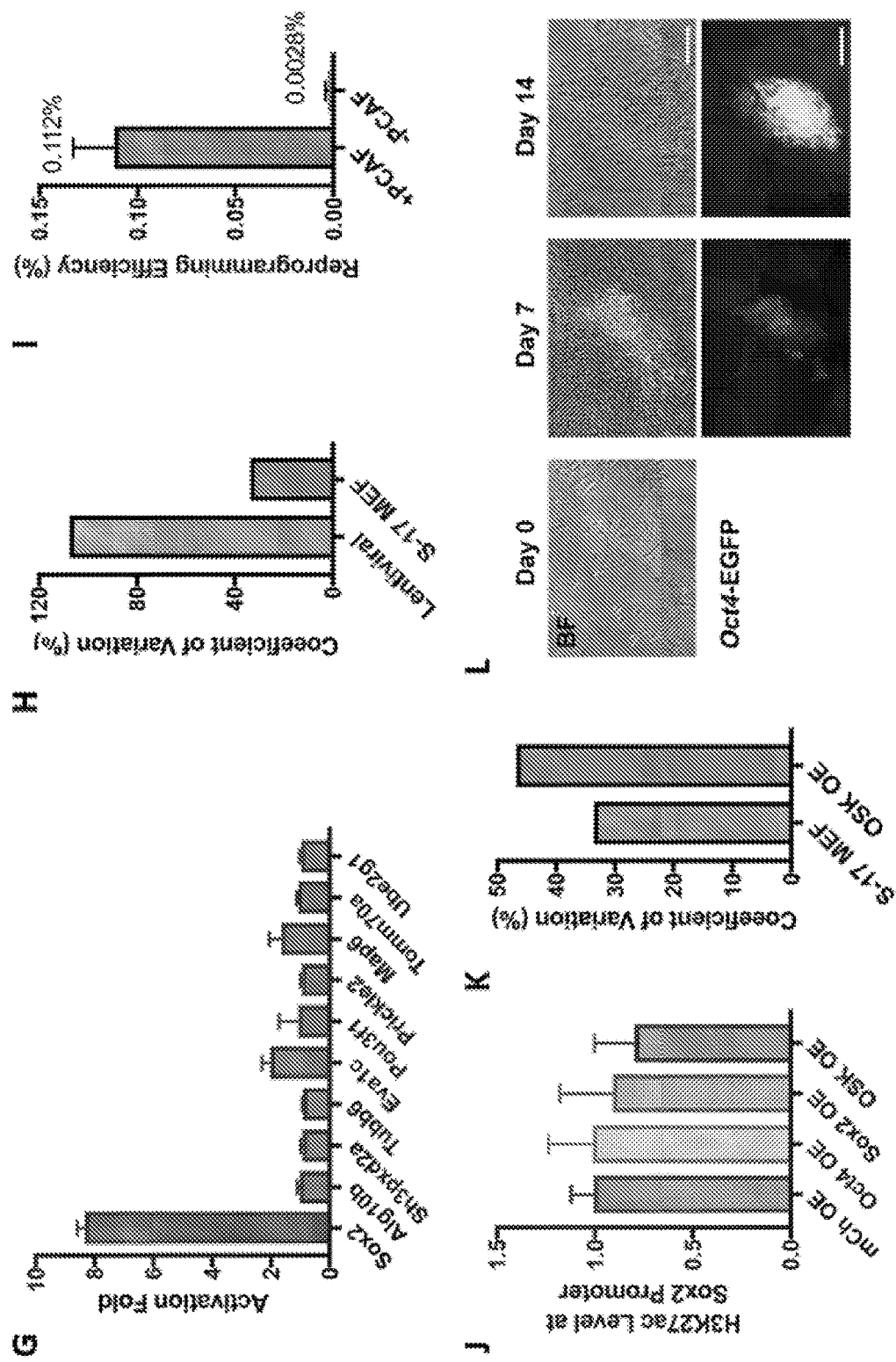

Example 4. S-17 MEFs are Reprogrammable with Higher Efficiency and Less Variation The reprogramming efficiency with lentiviral transduction was relatively low and variable in both OG2 and 129 mice (129S2/SvPasCrl, Charles River) derived MEFs (0-0.013%) (FIGS. 2C, 6A, 6F, 7A-7C). This might be due to inefficient delivery of SunTag components and random copy numbers of the components delivered into the cells. This was reflected by the varied copy numbers of sgRNA cassette in the genome of established iPSC lines, where one to five copies were found per cell among 12 lines (FIG. 7D). For quantification of the sgRNA cassette in the genome, quantitative RT-PCR (qPCR) primers were designed for the amplification of Sox2 gene and the sgRNA cassette in the genome (see Table 2). The amplification of Sox2 was used to normalize the genome for each cell line. Plasmids containing the targets were used for standard curve generation. The standard curves were generated by plotting Ct values against the plasmid copy numbers for a series of plasmid dilutions (10 pg, 1 pg, 0.1 pg, and 0.01 pg), and the copy numbers of Sox2 gene and sgRNA cassettes in around 30 ng of genomic DNA was calculated based on the standard curve. sgRNA copy numbers were then calculated by normalizing to Sox2 gene (2 copies/cell).

TABLE 2

Primer sequences for qPCR (related to all figures)

| Gene Name | | Sequence | Seq ID |
|---|---|---|---|
| Oct4 (total) | Forward | ACATCGCCAATCAGCTTGG | 65 |
| | Reverse | AGAACCATACTCGAACCACATCC | 66 |
| Oct4 (endogenous) | Forward | TAGGTGAGCCGTCTTTCCAC | 67 |
| | Reverse | GCTTAGCCAGGTTCGAGGAT | 68 |
| Sox2 (total) | Forward | ACAGATGCAACCGATGCACC | 69 |
| | Reverse | TGGAGTTGTACTGCAGGGCG | 70 |
| Sox2 (endogenous) | Forward | GAGAAGTTTGGAGCCCGAG | 71 |
| | Reverse | GATCTGGCGGAGAATAGTTGG | 72 |
| Klf4 | Forward | GCACACCTGCGAACTCACAC | 73 |
| | Reverse | CCGTCCCAGTCACAGTGGTAA | 74 |
| c-Myc | Forward | CCACCAGCAGCGACTCTGA | 75 |
| | Reverse | TGCCTCTTCTCCACAGACACC | 76 |
| Nr5a2 | Forward | ATGGGAAGGAAGGGACAATC | 77 |
| | Reverse | ATACAAACTCCCGCTGATCG | 78 |

TABLE 2-continued

Primer sequences for qPCR (related to all figures)

| Gene Name | | Sequence | Seq ID |
|---|---|---|---|
| Glis1 | Forward | CTCCAAGCATCCACACTGTT | 79 |
| | Reverse | GACAGGATGCCTGAAGCAAG | 80 |
| Cebpa | Forward | CAAGAACAGCAACGAGTACCG | 81 |
| | Reverse | GTCACTGGTCAACTCCAGCAC | 82 |
| Nanog | Forward | CCTCCAGCAGATGCAAGAACTC | 83 |
| | Reverse | CTTCAACCACTGGTTTTTCTGCC | 84 |
| Dppa2 | Forward | TCAACGAGAACCAATCTGAGGA | 85 |
| | Reverse | GCGTAGCGTAGTCTGTGTTTG | 86 |
| Esrrb | Forward | CTCGCCAACTCAGATTCGAT | 87 |
| | Reverse | AGAAGTGTTGCACGGCTTTG | 88 |
| Fgf4 | Forward | CGTGGTGAGCATCTTCGGAGTGG | 89 |
| | Reverse | CCTTCTTGGTCCGCCCGTTCTTA | 90 |
| Lin28 | Forward | TGTTCTGTATTGGGAGTGAGC | 91 |
| | Reverse | GCTTGCATTCCTTGGCATG | 92 |
| Tet1 | Forward | TCTCACTCATGTTGCGGGACCC | 93 |
| | Reverse | CGTCGGAGTTGAAATGGGCGAA | 94 |
| Utf1 | Forward | TGTCCCGGTGACTACGTCT | 95 |
| | Reverse | CCCAGAAGTAGCTCCGTCTCT | 96 |
| Actin | Forward | ATGGAGGGGAATACAGCCC | 97 |
| | Reverse | TTCTTTGCAGCTCCTTCGTT | 98 |
| Oct4 (ChIP-2.7k) | Forward | TGGCCTGGAACTCAGAAATC | 99 |
| | Reverse | TCTGCCCCCTTTAAGAGTCA | 100 |
| Oct4 (ChIP-1.4k) | Forward | CCCAGGCTCAGAACTCTGTC | 101 |
| | Reverse | TGCTCCTACACCATGCTCTG | 102 |
| Oct4 (ChIP-0.2k) | Forward | TTGAAAATGAAGGCCTCCTG | 103 |
| | Reverse | AGCGCTATCTGCCTGTGTCT | 104 |
| Sox2 (ChIP-0.4k) | Forward | CTTGGGTCTAACTTCTCGTCTG | 105 |
| | Reverse | GTGTGCCATTGTTTCTGCG | 106 |
| Nanog (ChIP-0.5k) | Forward | CCAACTTACTAAGGTAGCCCG | 107 |
| | Reverse | CTTTCAGCACTCAGCGTTTC | 108 |
| Rex1 (ChIP-0.5k) | Forward | CCCCGCTACAAAGTACACTAG | 109 |
| | Reverse | CTAGACCGTTTGTAGTCAGTGG | 110 |
| Ctnnbl1 | Forward | AGAACGACAGTGAGAAGGTTG | 111 |
| | Reverse | CATTGTCTATGATCTCCCCACG | 112 |
| Tbc1d22b | Forward | TTCTGTTTATCTGGGCCATCC | 113 |
| | Reverse | GTCAAAGTTCTCCACGTCCTC | 114 |
| Phf20 | Forward | AGTGTGAAGAGTGCCAGTG | 115 |
| | Reverse | CTCAGCCACTCCTTGTCATAC | 116 |
| Rgr | Forward | GTACCTATACGCAGCCATCG | 117 |
| | Reverse | TTCCTCTACAGACCATCTCCC | 118 |
| Zp3r | Forward | ACTGTCCTGAAATATACCTGCC | 119 |
| | Reverse | ACTTTCCCATTGACCAACTCG | 120 |
| Lmbr1 | Forward | GCGGTGGGTATGAAAGGAG | 121 |
| | Reverse | AGGAAACGATGTAGAGAATGC | 122 |
| D130040H23Rik | Forward | GACCTACAGCAACCTCACTG | 123 |
| | Reverse | GCAAAGGCTTTACCACACTG | 124 |
| Gli3 | Forward | TTCAGCAAGTGGTTCCTATGG | 125 |
| | Reverse | CTGTCGGCTTAGGATCTGTTG | 126 |
| Vav3 | Forward | TGTCAAACCCTCTCCATGTG | 127 |
| | Reverse | TCTTTGGTCCTGTGCCTTAC | 128 |
| Renbp | Forward | CACAGTGAAGCCATGATTGC | 129 |
| | Reverse | AGCCAAACCATTCCCCATAC | 130 |
| Rab11fip4os1 | Forward | GTCTCTGATGGAAGGATGCTG | 131 |
| | Reverse | GCCTTAATTTGTTTTGCCTCGG | 132 |
| Styk1 | Forward | GAAAATCATGAAGAGACCCAGC | 133 |
| | Reverse | CATCGGCAGATCTAGAAGCAG | 134 |
| Cyb5a | Forward | CAGAAGCACAAAGACAGCAAG | 135 |
| | Reverse | AAATTCTCGGTAGCATCACCC | 136 |
| Zak | Forward | GTAATGGAGAAGTGGATCGTGG | 137 |
| | Reverse | TTCGTTCTGTCCCACTGTATG | 138 |
| Tec | Forward | GAAACAGCAACATCCCCAAAG | 139 |
| | Reverse | CTTCCCCTTTGTACTGACCG | 140 |
| Fbn2 | Forward | ACCTGAATCCCAACATCTGC | 141 |
| | Reverse | CCAATCTCACACTCGTCCAC | 142 |
| Zfp653 | Forward | CCACCTCTATAGCCAGCATTG | 143 |
| | Reverse | CCATCCACTTCTGCCTCTG | 144 |
| Ptgis | Forward | AGGATGAAGGAAAAGCACGG | 145 |
| | Reverse | CATGAGGAAGATGGCATAGGG | 146 |
| Alg10b | Forward | CAACTTCTACTTGCTGTATTTGCTC | 147 |
| | Reverse | GACCCAGCTTCTGTATAGTAAAGG | 148 |
| Sh3pxd2a | Forward | AGGAAATCAGTGTGGTTGTCC | 149 |
| | Reverse | AGCTCCGAGTTCTCTTGTTTC | 150 |
| Tubb6 | Forward | AGAGGCATTTGAAGACGAGG | 151 |
| | Reverse | CCAGTGACATGCTTAGACCAG | 152 |
| Eva1c | Forward | ACCAAATGTGTAGTTCCCAGG | 153 |
| | Reverse | GAAGACTCGGCTATTGACCAG | 154 |
| Pou3f1 | Forward | GCTCTGTGCAGTGACCC | 155 |
| | Reverse | GTAAAATCCAAAGCAAAACCGAATAA | 156 |
| Prickle2 | Forward | AACCAGAGGAAACGTGAGAAC | 157 |
| | Reverse | GTGATGCAAACACAGCGATG | 158 |
| Map6 | Forward | CAGTGCTACCAAACCCGAC | 159 |
| | Reverse | ACAGAGCCTTGATCCTTGTG | 160 |
| Tomm70a | Forward | CAGTGGCGGATTTTGATGC | 161 |
| | Reverse | AACCTTTCATAGCTGCCTGG | 162 |
| Ube2g1 | Forward | AATGGAGGGAAGACAGAAACG | 163 |
| | Reverse | CAGTGCCATGTTTCTCAATTGG | 164 |
| sgRNA cassette (quantification) | Forward | CTATGTGGACTACAGACTGGAAAG | 165 |
| | Reverse | CTAGGGAGGTCGCAGTATCT | 166 |

Figure 3:
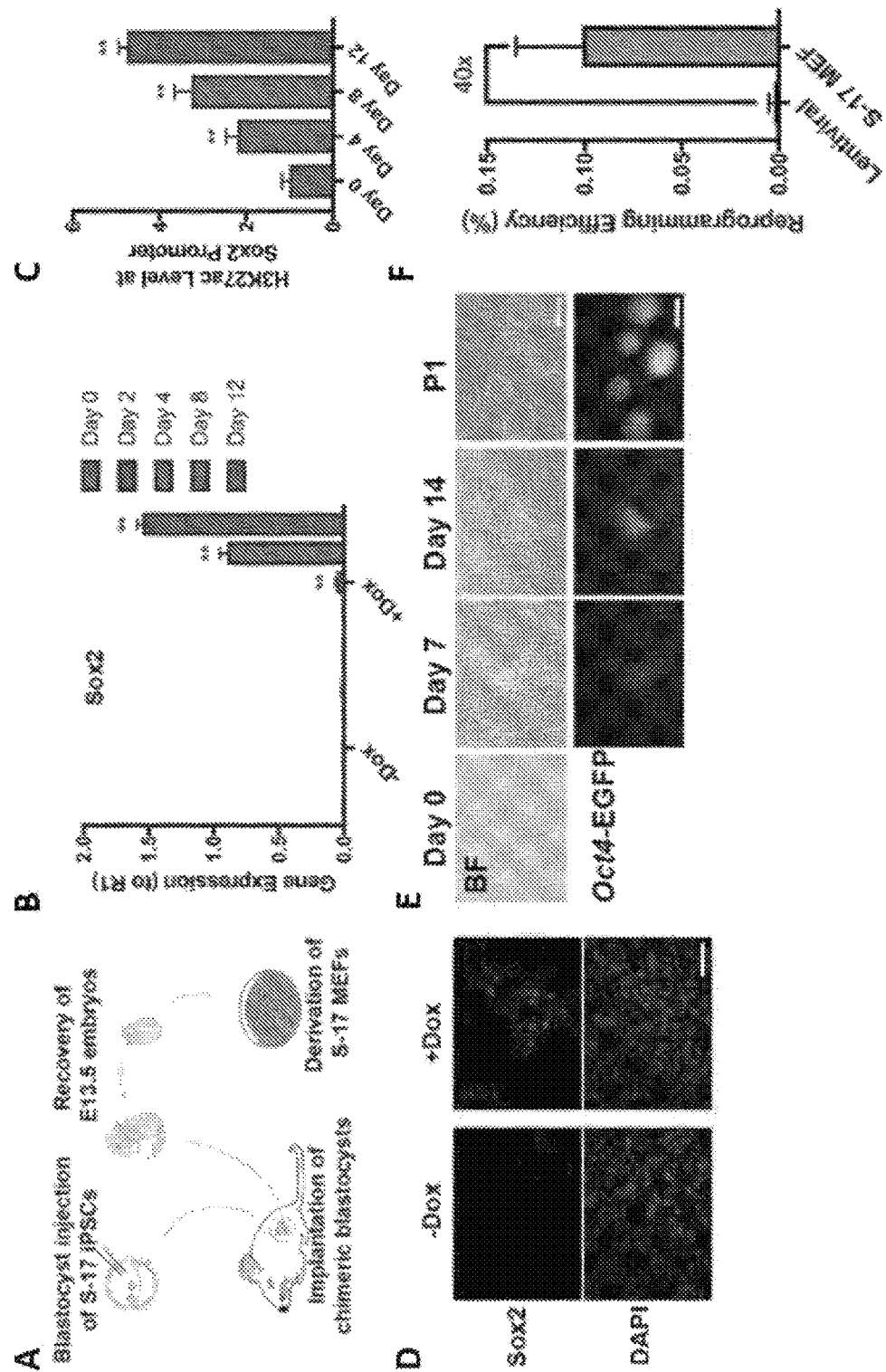
FIG. 3 demonstrates remodeling of Sox2 promoter triggers reprogramming towards pluripotency in S-17 MEFs. (A) Scheme showing the generation of S-17 MEFs. (B) Sox2 activation over 12 days with or without doxycycline in S-17 MEFs. (C) Histone H3K27 acetylation levels at Sox2 promoter on days 0, 4, 8, and 12. (D) Detection of Sox2 expression by immunofluorescent staining in the presence of doxycycline (scale bar: 100 µm). (E) S-17 MEFs were reprogrammed to form EGFP-positive colonies, and iPSC line was established (scale bar: 200 µm). (F) Comparison of efficiencies of lentiviral SunTag reprogramming and S-17 MEF reprogramming. (G) Gene expression of Oct4, Nanog, and Rex1 over 12 days in S-17 MEF reprogramming. (H) Histone H3K27 acetylation levels at Oct4, Nanog, and Rex1 promoters on days 0, 4, 8, and 12. (I) Histone H3K27 acetylation levels at Oct4 enhancer on days 0, 4, 8, and 12. (J) Sox2 dependency in S-17 MEF reprogramming. Four different concentrations (0, 0.01, 0.1, and 1 µg/ml) of doxycycline were used, and Sox2 activation (left) and reprogramming efficiency (right) are shown. (K) Synergy of Oct4 and Sox2 remodeling in S-17 MEF reprogramming. Oct4 gene activation (left) and reprogramming efficiency (right) were examined. (L) Total (left) and endogenous Sox2 (right) expression on days 4 and 12 when pluripotent genes were overexpressed (OE). Three conditions were tested, Oct4 alone, Sox2 alone and OSK (Oct4, Sox2, and Klf4), and the overexpression of mCherry (mCh) was used as a control. (M) Comparison of reprogramming efficiency of S-17 MEFs and pluripotent gene overexpression. Data in (B), (C), (G), (H), (I), and (K) represent mean±SD (n=4). p values in (B) were determined by two-way ANOVA with Bonferroni test, p values in (C), (G), (H), and (I) were determined by one-way ANOVA with Dunnett test, and p values in (K) were determined by unpaired t test. **p<0.01; *p<0.05.
Figure 3:
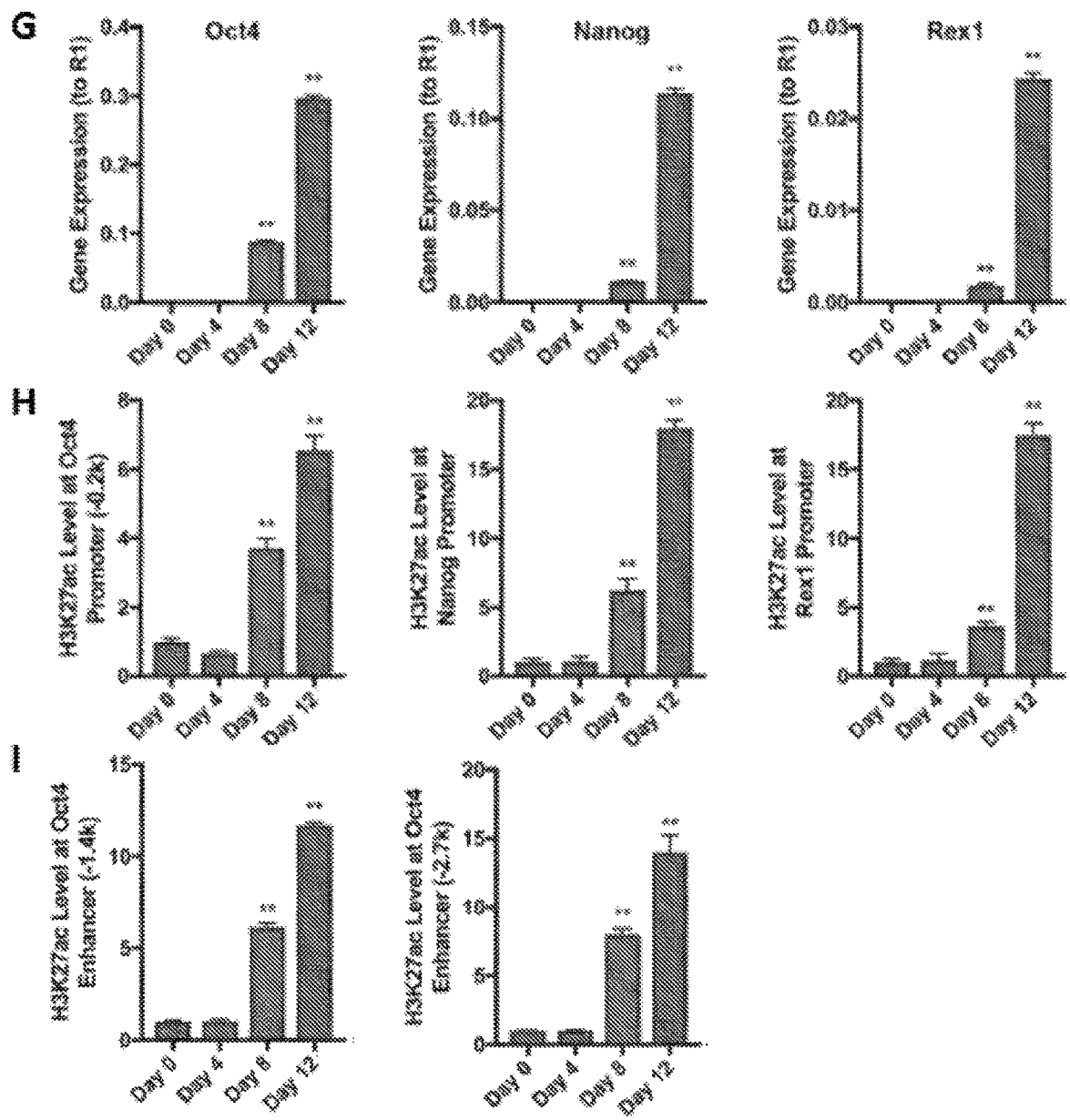
Figure 3:
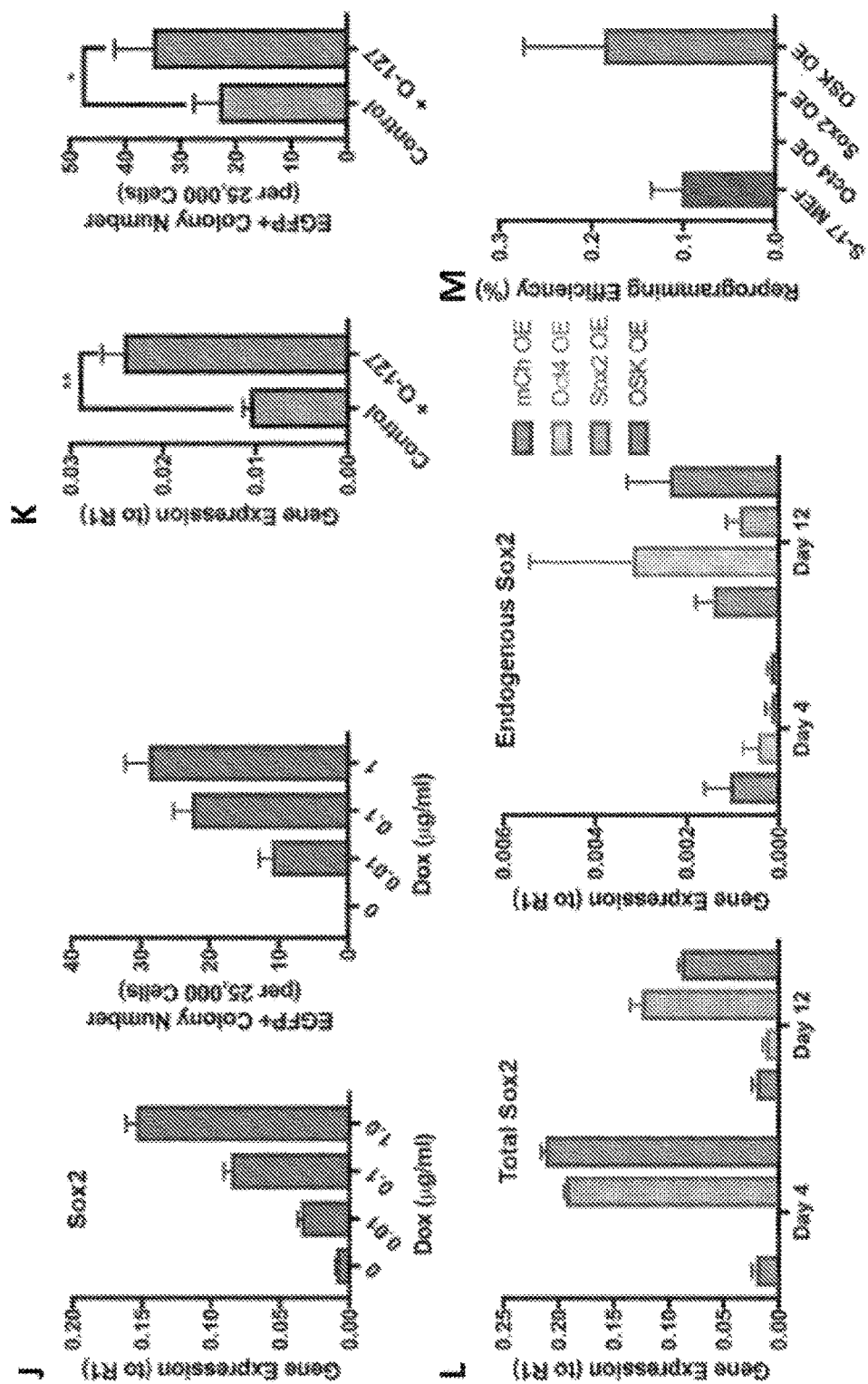

To decrease variability and enhance efficiency, secondary MEFs were generated using a CRISPR iPSC line that was derived from a single colony. S-17 iPSCs were labeled with blue fluorescence protein (BFP) and injected into B6 blastocysts, and secondary MEFs were derived from E13.5 embryos (FIG. 3A). About half of the MEFs (52.4%) were originated from the S-17 iPSCs revealed by flow cytometry (FIG. 7E), during which cells were trypsinized to form single cell suspension in FACS buffer (2% FBS in DPBS) and the suspension filtered through 40 μm cell strainer before it was examined by the MACSQuant VYB flow cytometer. The data was analyzed with FlowJo v10. These derived secondary MEFs were termed S-17 MEFs. With doxycycline induction, endogenous Sox2 was readily detected by both qPCR and immunofluorescent staining, and Sox2 was not detected in the absence of doxycycline (FIGS. 3B and 3D). No off-target genes were significantly elevated (FIG. 7G). These data demonstrate that the SunTag system functioned properly to activate Sox2 in S-17 MEFs.

It was next examined whether the S-17 MEFs were reprogrammable. Sox2 transcription was significantly upregulated on day 4 and increased quickly to levels comparable to R1 ES cells by day 8 (FIG. 3B). Following Sox2 upregulation, other core pluripotent factors, Oct4, Nanog, and Rex1, were also activated. Their transcription was detected on day 8 and elevated dramatically afterwards (FIG. 3G). Meanwhile, morphological changes were observed from day 4, and EGFP-positive colonies were visible on day 7 (FIG. 3E). iPSC lines could also be established (FIG. 3E). With S-17 MEFs, the reprogramming efficiency (0.1%) increased by 40-fold over the lentivirus method (FIG. 3F). As expected, much less variability was observed (FIG. 7H).

For qPCR (see Table 2), total RNA was extracted from samples at the indicated times with the RNeasy Plus mini kit with QiaShredder (Qiagen) and treated with DNA-free Kit (Ambion) to remove genomic DNA. RNA was reverse-transcribed using the iScript cDNA synthesis kit (Bio-Rad). Quantitative PCR was performed with iQTM SYBR Green Supermix (Bio-Rad) on the 7500 Fast Real-Time PCR System (Applied Biosystems). All reactions were done in quadruplicate. All data were statistically analyzed with Prism 7. For immunofluorescent staining, cells were washed three times with DPBS and fixed with 4% PFA for 30 minutes at 4° C. Donkey serum (10% in DPBS) was used for blocking for 1 hour at 4° C. Antibodies were diluted in DPBS with 1% BSA. The following primary antibodies were used for staining: anti-Sox2 (1:1000, Millipore, AB5603), anti-Oct4 (1:1000, Santa Cruz, sc-5279), anti-Nanog (1:500, Abcam, 80892), and anti-SSEA-1 (1:200, Stemgent, 09-0095).

It was also tested whether more differentiated tail tip fibroblasts (TTFs) were reprogrammable. S-17 TTFs were derived from the 14-month-old adult chimeric mouse. The tail was peeled, minced into 1 mm pieces, and cultured in 6 cm dish. Medium was half changed every 3 days until fibroblasts migrated out of the graft pieces. The derived TTFs were maintained in DMEM supplemented with 10% FBS and non-essential amino acids, and were then passaged and ready for use (P1). In the presence of doxycycline, TTFs underwent morphological changes, and EGFP-positive colonies were obtained in two weeks (FIG. 7L). These observations show that S-17 MEFs and TTFs were both reprogrammable.

For reprogramming with S-17 MEFs or mouse TTFs, MEFs or TTFs were seeded onto gelatin-coated plates at the density of 5,000 cells/cm$^2$. After 24 hours, the medium was switched to reprogramming medium with 1 µg/ml doxycycline. This was denoted as day 0. Medium was changed every other day until day 14. EGFP-positive colonies were counted for reprogramming efficiency calculation or used for iPSC line derivation.

Example 5. Remodeling of Sox2 Promoter Triggers Reprogramming Towards Pluripotency in S-17 MEFs Without doxycycline, activation of Sox2 could not be detected and no colonies were obtained (FIGS. 3B and 3J). When the PCAF cocktail was removed from the medium, EGFP-positive colonies were still generated (FIG. 7I), although with lower efficiency. This observation concluded that endogenous Sox2 activation was the trigger for S-17 MEF reprogramming.

It was next examined whether the reprogramming was dose-dependent on Sox2 level. Sox2 was activated with a series of doxycycline concentrations, e.g., 0, 0.01, 0.1, and 1 µg/ml. Sox2 level showed a positive correlation with doxycycline concentration, and the reprogramming efficiency was clearly dependent on Sox2 level (FIG. 3J).

Because VP64 promotes gene transcription and chromatin remodeling by recruiting multiple epigenetic modifiers (Hirai et al., 2010), whether and how the SunTag system could epigenetically remodel Sox2 promoter were examined. Chromatin-immunoprecipitation (ChIP) was performed with H3K27 acetylation (H3K27ac) antibody against Sox2 promoter. All ChIP experiments were performed with EZ-ChIP Chromatin Immunoprecipitation kit (Millipore, 17-371), following the protocol provided with the kit with modifications. Briefly, about 2×10$^6$ cells were crosslinked with 0.275 ml of 37% formaldehyde to 10 ml of growth medium. 1 ml of 1.25 M glycine (10×) were added to quench unreacted formaldehyde. 0.12 ml of SDS lysis buffer was used for each sample. Genomic DNA was then sheared to a length of 100-500 bp on Covaris S2 Sonicator with optimized conditions. 1.5 µg of H3K27 acetylation antibody (Abcam, ab4729) and 15 µL of magnetic protein A/G beads (Millipore 16-663) were used for each sample. Finally, DNA fragments were eluted with 50 µl of elution buffer C, which was used for downstream qPCR.

As early as day 4, H3K27ac level was already elevated twofold, and it further increased on days 8 and 12 (FIG. 3C). This indicates that the Sox2 targeting SunTag system caused gradual and constant epigenetic remodeling at the Sox2 promoter. Epigenetic remodeling of the promoters of Oct4, Nanog, and Rex1 was also tested, and their H3K27ac levels increased significantly with a 4-day latency, similar to the gene transcription (FIGS. 3G and 3H). Interestingly, the enhancers of Oct4 showed simultaneous elevation of H3K27ac level (FIG. 3I). These data suggest that activation of Sox2 facilitated subsequent induction of other key genes for pluripotency establishment.

It was then tested whether additional targeting of Oct4 promoter in S-17 MEFs would promote reprogramming efficiency. Transduction of O-127 led to a significant increase of Oct4 transcription, and reprogramming efficiency was also increased (FIG. 3K). This synergistic effect supported the idea that Oct4 and Sox2 cooperated in pluripotency induction.

S-17 MEF reprogramming and traditional reprogramming using overexpressed factors were also compared. Unlike S-17 MEFs, overexpressed factors failed to epigenetically remodel Sox2 promoter on day 4 (FIG. 7J), and no Sox2 transcription at the endogenous loci was effectively detected on days 4 and 12 (FIG. 3L). After 3 weeks, overexpression of Oct4 or Sox2 failed to generate any colonies, and overexpression of Oct4, Sox2, and Klf4 (OSK) generated EGFP-positive colonies slightly more than S-17 MEFs with more variation between experiments (FIGS. 3M and 7K).

Example 6. Simultaneous Remodeling of Oct4 Promoter and Enhancer Reprograms MEFs to iPSCs Remodeling of both the promoter and the enhancer of Oct4 was important for pluripotency induction, and targeting the promoter alone was not sufficient for the generation of EGFP-positive colonies (FIGS. 6A and 2C). Given that key pluripotency factors as well as p300 and the Mediator complex are enriched at the Oct4 distal enhancer in mouse ES cells (FIG. 4A), it was hypothesized that simultaneous remodeling of Oct4 promoter and enhancer would be required for pluripotency induction.

Figure 8:
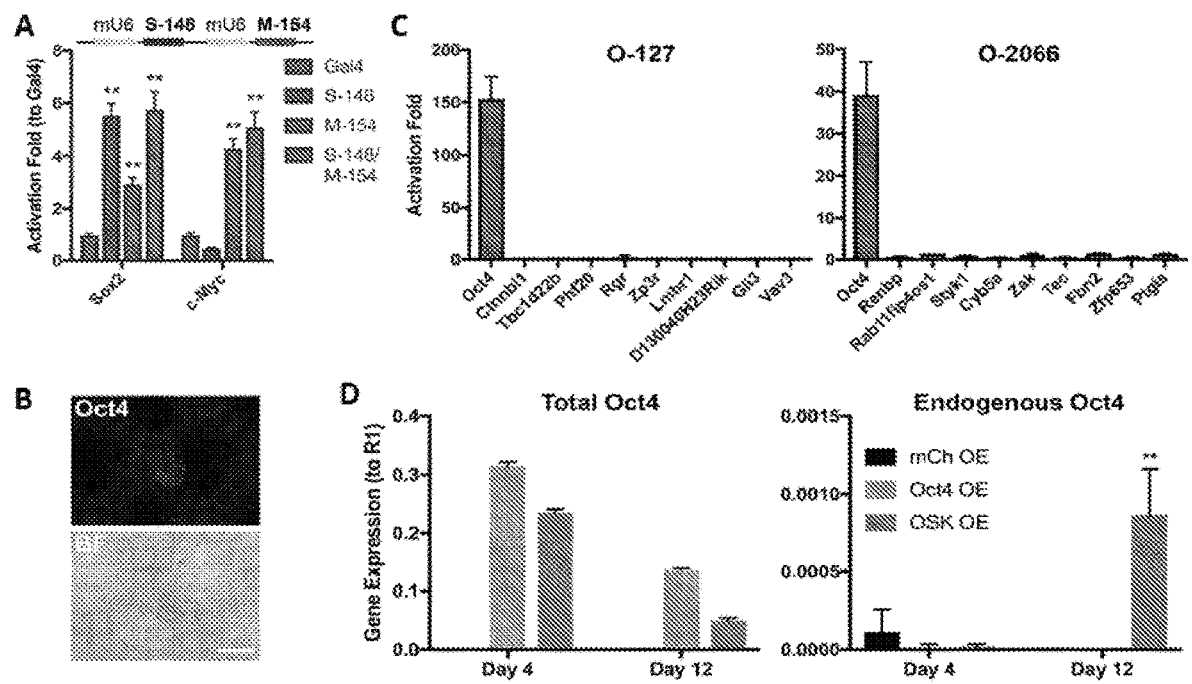
FIG. 8 demonstrates simultaneous remodeling of Oct4 promoter and enhancer reprograms MEFs into iPSCs. (A) Function verification of dual-sgRNA cassette in differentiating ES cells by introducing two sgRNA targeting Sox2 (S-148) and c-Myc (M-154). (B) Oct4 protein staining on day 8 of reprogramming (scale bar: 200 μm). (C) Examination of off-target effects of O-127 (left) and O-2066 (right). Transcription of the top 10 predicted targets for each sgRNA were examined by qPCR. (D) Transcription of total (left) and endogenous (right) Oct4 on days 4 and 12 when pluripotent genes were overexpressed (OE). Two conditions were tested, Oct4 alone and OSK (Oct4, Sox2, and Klf4). mCherry was used as a negative control. (E) Scheme depicting dCas9-SunTag-p300core and its function. (F) Histone H3K27 acetylation levels at Oct4 enhancer and promoter on day 5 for dCas9-SunTag-VP64 and dCas9-SunTag-p300core systems. Three different sites were examined, 2.7 kb, 1.4 kb and 0.2 kb upstream of the transcription start site. (G) Transcriptional activation of Oct4 with dCas9-SunTag-VP64 or dCas9-SunTag-p300core over 15 days. (H) Morphology of EGFP-positive colonies in situ and P1 iPSCs (D-16) generated by manipulating the acetylation of Oct4 promoter and enhancer with dCas9-SunTag-p300core (scale bar, 200 μm). (I) Comparison of pluripotency gene expression in D-16 cell line and R1 ES cells. Data in (A), (D), and (G) represent mean±SD (n=4). p values in (A) and (D) were determined by two-way ANOVA with Bonferroni test, and p values in (G) were determined by unpaired t test. **p<0.01; ns, non-significant.
Figure 8:
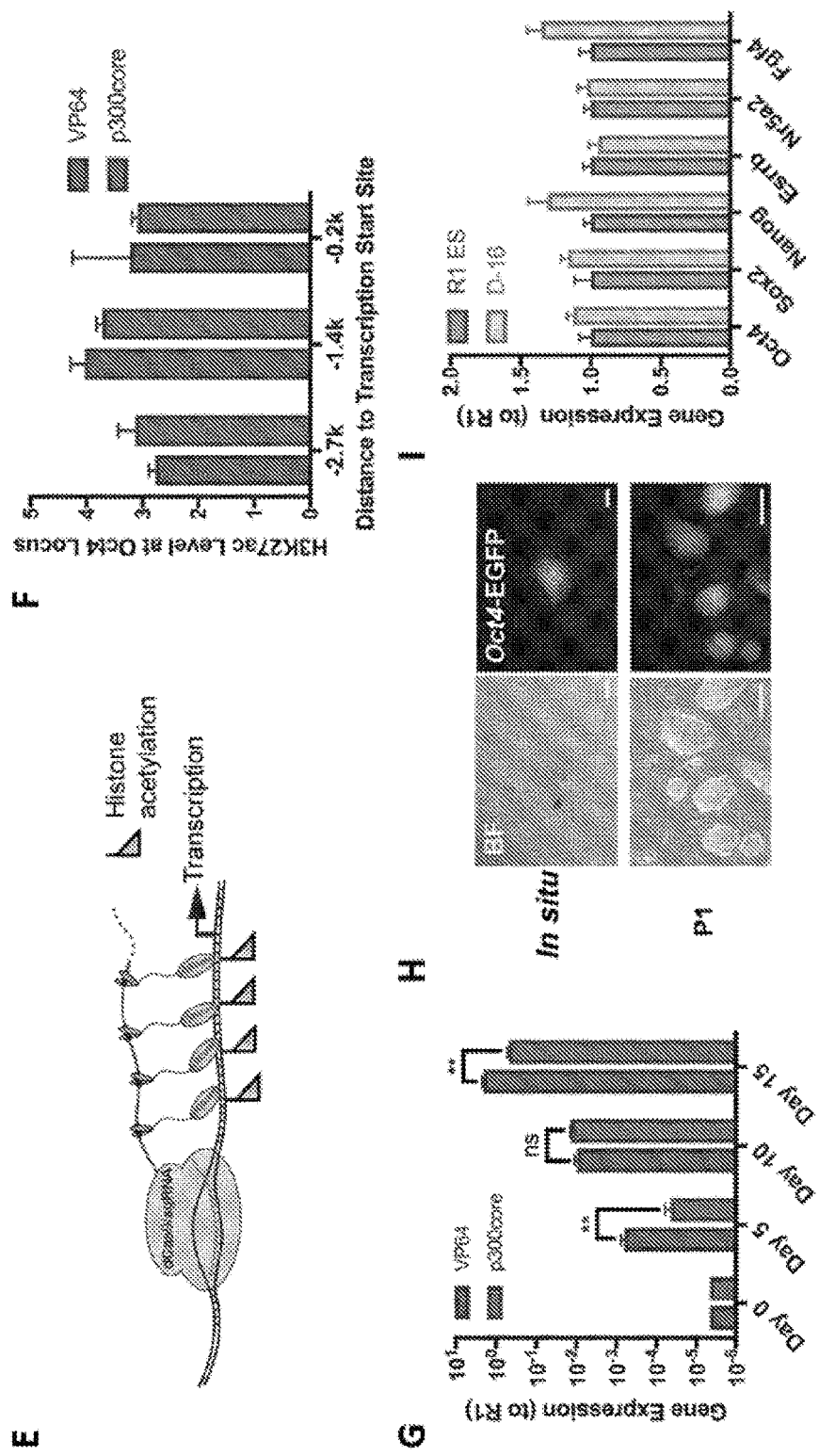

To test the hypothesis, a dual-sgRNA cassette that transcribed two sgRNAs targeting different sites was used (FIG. 8A). The O-127-2066 cassette targeted Oct4 promoter (O-127) and enhancer (O-2066) at a single-cell level. To generate the dual-sgRNA constructs, a fragment containing the second sgRNA was amplified using primers mU6-T2H-F (SEQ ID NO: 167 ctaggatccattaggcGGGTA-CAGTGCAGGGGAA) and mU6-T2H-R2 (SEQ ID NO: 168 atacggttatccacgcGGCCGCCTAATGGATCCT) with the single sgRNA construct as a template. This fragment was purified and used for recombination reaction with the other construct containing the first sgRNA digested by NotI. The second mU6-sgRNA cassette is downstream of the first one in the same transcription direction.

Figure 4:
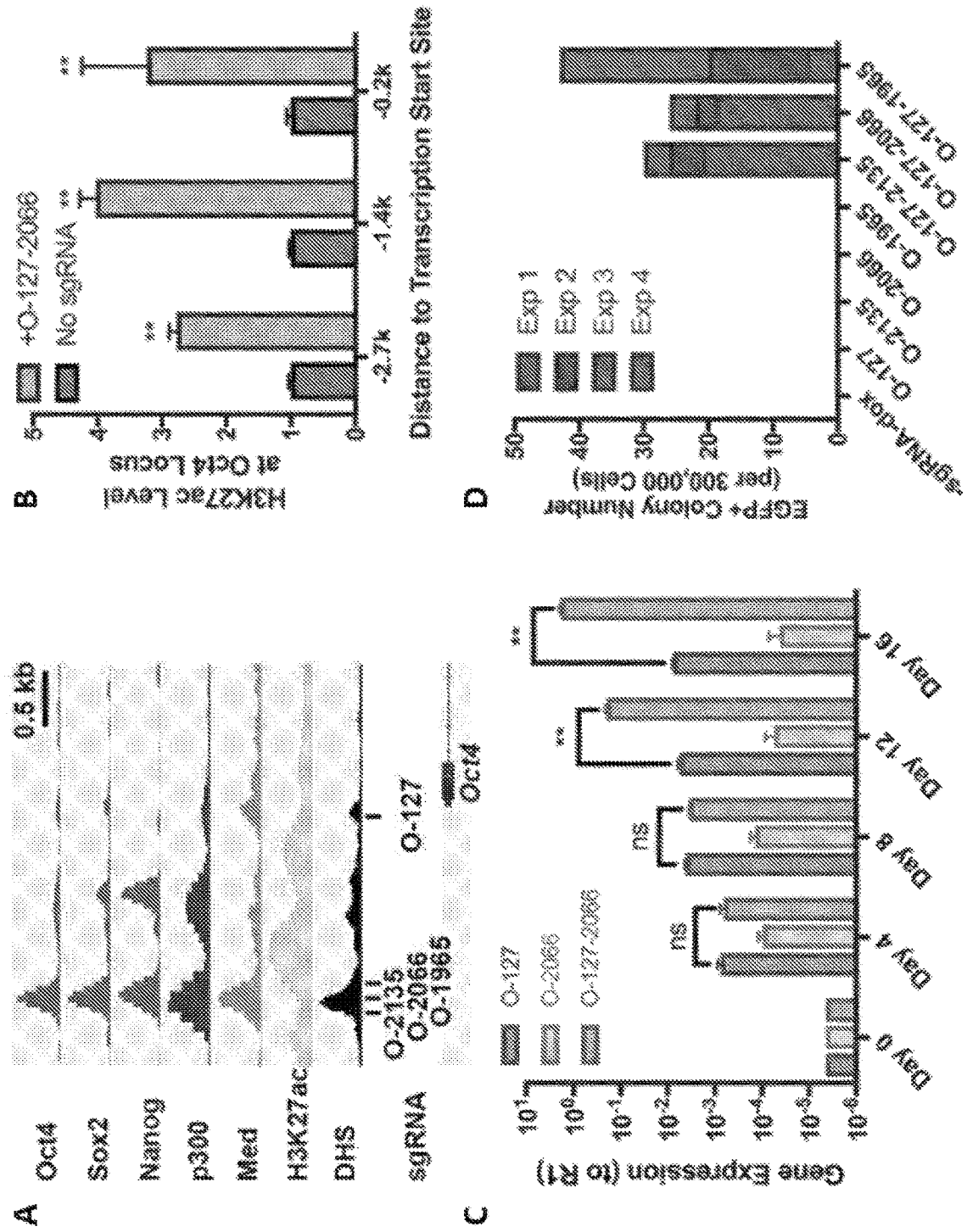
FIG. 4 demonstrates simultaneous remodeling of Oct4 promoter and enhancer reprograms MEFs to iPSCs. (A) Scheme depicting the sgRNA targeting sites for Oct4 promoter and enhancer along with the binding peaks of transcription factors (Oct4, Sox2, Nanog), histone acetyltransferase p300, the Mediator complex, and the distributions of histone H3K27ac and DNase hypersensitive sites (DHS) (Whyte et al., 2013). (B) Histone H3K27 acetylation levels at Oct4 enhancer and promoter on day 4. Three different sites were examined, 2.7 kb, 1.4 kb and 0.2 kb upstream of the transcription start site. (C) Endogenous Oct4 transcription in the presence of O-127, O-2066, or O-127-2066 sgRNA over 16 days. (D) Numbers of colonies generated from remodeling of Oct4 promoter (O-127), enhancer (O-2135, O-2066, O-1965), or promoter and enhancer simultaneously (O-127-2135, O-127-2066, O-127-1965). Four independent experiments are shown. No colony was observed in O-127-2135 culture of experiment 3 and O-127-2066/1965 of experiment 4. (E) Morphology of EGFP-positive colonies in situ and P0 iPSCs from simultaneous remodeling of Oct4 promoter and enhancer (O-127-2066) (scale bar, 200 µm). (F) Nanog, Sox2, and Rex1 expression in Oct4-EGFP-positive colonies (scale bar, 200 µm). (G) Comparison of pluripotency gene expression in D-9 cell line and R1 ES cells. (H) Karyotyping of D-9 line. (I)-(K) Characterization of the pluripotent D-9 line in vivo. Chimeric mice were generated with D-9 cells (J), and these cells contributed to the gonadal tissue represented by intense EGFP signal (I) and were competent for germline transmission (K). Data in (B) and (C) represent mean±SD (n=4). p values were determined by unpaired t test. **p<0.01.
Figure 4:
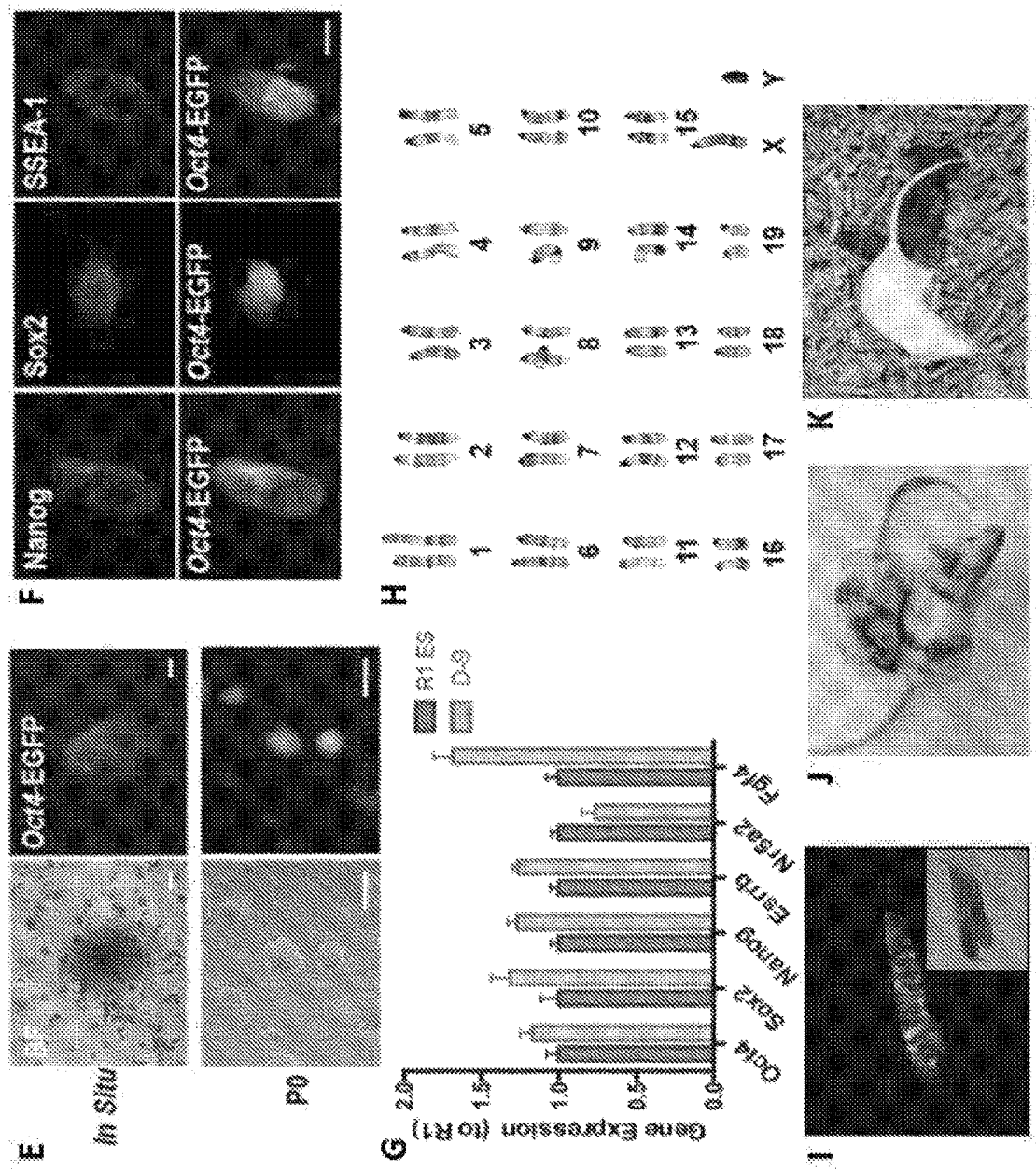

O-127-2066 led to simultaneous remodeling of Oct4 promoter and enhancer with elevated levels of H3K27ac (FIG. 4B). The level of gene transcription by O-127-2066 was similar to O-127 at days 4 and 8 (FIG. 4C). However, after day 8, Oct4 transcription was further elevated in O-127-2066 culture. Particularly, when the cells were replated on days 7 and 11 to allow cell expansion, the overall Oct4 expression in the population dramatically increased (FIG. 4C). For O-127 and O-2066 cultures, weak Oct4 expression largely stayed unchanged after day 8 (FIG. 4C). Accordingly, by day 12, EGFP-positive colonies were observed in the O-127-2066 culture, and those colonies also expressed Nanog, Sox2, and SSEA-1, indicating the acquired core pluripotency network (FIGS. 4E and 4F). iPSC lines could be derived from these colonies (FIG. 4E). Meanwhile, no colonies were found in the O-127 or O-2066 culture (FIG. 4D).

The activation of potential off-targets was examined. The top 10 predicted targets for sgRNAs O-127 and O-2066 were examined, and no significant activation of the off-target genes was detected (FIG. 8C). Another two dual sgRNA cassettes O-127-1965 and O-127-2135 were also tested in parallel, and similar results were observed (FIG. 4D). These data strongly supported that pluripotency was induced by simultaneous remodeling of endogenous Oct4 promoter and enhancer.

An authentic pluripotent stem cell line was also achieved. The D-9 line showed similar expression of pluripotency genes to R1 ES cells and a normal karyotype (FIGS. 4G and 4H). After injection of D-9 cells into B6-albino blastocysts, live-born chimeric mice were generated at the rate of 60% among the offspring pups (6 out 10) (FIG. 4J). This line significantly contributed to the gonadal regions of 75% E13.5 embryos (6 out of 8) (FIG. 4I), and germline transmission was confirmed in 50% of male pups (2 out of 4) (FIG. 4K).

Example 7. Epigenetic Remodeling of Histone Acetylation at Oct4 Promoter and Enhancer Reprograms MEFs to iPS Cells Chromatin remodeling by VP64 is due to its primary function in recruiting the transcription machinery. To more strictly determine if epigenetic remodeling would be sufficient to initiate reprogramming, histone acetylation of Oct4 promoter and enhancer was increased by specific manipulations. Histone acetylation was manipulated because histone H3K27 acetylation synchronously marks the Oct4 promoter and enhancer regions (FIG. 4A). p300core only has the acetyltransferase activity domain of p300 and was proved to enhance the target's histone acetylation (Hilton et al., 2015). Thus, VP64 was replaced with p300core to generate a dCas9-SunTag-p300core system (FIG. 8E).

For cloning of p300core, the backbone was derived from pSLQ1711-pPGK-ScFV(GCN4)-sfGFP-VP64 by digestion with SbfI-HF and RsrII (NEB) and retrieved using gel purification kit (Qiagen). An 83-bp SV40 nuclear localization site (NLS) with a linker was cloned and added between sfGFP and p300core with the forward primer (SEQ ID NO: 169 TACAAAGGTG-GAGGTCGGACCGaaggcagcggctcccccaag) and reverse primer (SEQ ID NO: 170 AAATCGTCTAAAGCATCcgaccctccgccggaaccgccca).

p300core was PCR-amplified from template pcDNA-dCas9-p300 Core (Addgene 61357) using Phusion® High-Fidelity DNA Polymerase (NEB) with the forward primer (SEQ ID NO: 171 AGTGGGCGGTTCCGGCGGAGGGTCGattttcaaaccagaagaactacgac) and reverse primer (SEQ ID NO: 172 TATCAAGCTTGCATGCCTGCAGGT-TAgtcctggctctgcgtgtgcagctc). Then, the backbone containing 83-bp SV4 NLS and the linker, and p300core were assembled using Gibson assembly cloning kit (NEB).

Reprogramming experiments were performed with the dCas9-SunTag-p300core system. p300core culture exhibited similar H3K27ac level to the VP64 counterpart at Oct4 promoter and enhancer, but only 1/30 of Oct4 transcription was detected in p300core culture on day 5 (FIGS. 8F and 8G). This can be explained by p300core's inability to recruit transcription machinery. Cultures were then passaged on days 9 and 14. Interestingly, by day 10, Oct4 levels were comparable in the VP64 and the p300core cultures (FIG. 8G). Accordingly, EGFP-positive colonies were produced in the p300core culture, and iPSC lines were generated (FIGS. 8H and 8I). These observations indicate that the manipulation of histone acetylation with p300core led to chromatin remodeling similar to VP64, although with a noticeable latency in transcriptional activation. Together, these results show that the epigenetic remodeling of Oct4 promoter and enhancer, either through VP64 or p300core, is sufficient to trigger reprogramming towards pluripotency.

With the extensive binding of ectopic proteins, it is quite difficult to identify the remodeling events on endogenous chromatin that trigger reprogramming to pluripotency. To gain insights into this, a CRISPRa system, dCas9-SugTag-VP64 or dCas9-SunTag-p300core, was utilized to precisely remodel specific sites of endogenous chromatin. For the first time, it was discovered that targeted remodeling of single genes, either Oct4 or Sox2, is sufficient to initiate reprogramming towards pluripotency, and authentic pluripotent stem cell lines were established. The CRISPR iPSC-derived S-17 MEFs and TTFs were also reprogrammable, suggesting the activation of endogenous Sox2 to be a critical event for pluripotency induction. Simultaneous remodeling of the promoter and enhancer of Oct4 was also sufficient to induce pluripotency. Finally, epigenetic manipulation of Oct4 promoter and enhancer by increasing histone acetylation was sufficient to trigger iPSC induction.

In the present studies, iPSCs were generated with CRISPRa system by targeting single genes, Oct4 or Sox2. The activation of endogenous pluripotency genes had been examined previously with CRISPRa systems, but no iPSCs were established. Prior studies showed only transient activation of the Oct4 promoter. It is contemplated that iPSCs failed to be generated, at least in part, because enhancers were not targeted. In the present disclosure, sgRNAs were designed de novo and sgRNA target sites were selected based on multiple parameters (FIGS. 5A-5C). The SunTag system used can be very efficient in gene activation and chromatin remodeling because as many as 24 copies of VP64 may be recruited to the targeting sites. As a result, a 100-fold increase in Oct4 activation was observed, which was much higher than previous work (Hu et al., 2014). Additionally, small molecules further enhanced the reprogramming efficiency (FIG. 7H). Recently, two studies reported generation of muscle and neuron cells by activating endogenous MyoD or BAM (Brn2, Ascl 1, and Myt1L) with a $^{VP64}$dCas9$^{VP64}$ system (Black et al., 2016; Chakraborty et al., 2014). The present disclosure established pluripotent stem cells for the first time with the CRISPRa method.

This disclosure mechanistically specified that direct remodeling of endogenous Oct4 or Sox2 is sufficient to trigger reprogramming towards pluripotency. This not only provides an alternative way for iPSC generation, but also provides insights into the molecular mechanism of pluripotency induction. The Sox2 study proved that activation of endogenous Sox2 is a critical event for pluripotency induction. It was clear that Sox2 activation was required for S-17 MEF reprogramming, the remodeling of Sox2 preceded other key pluripotent gene activation, and the reprogramming efficiency was dependent on Sox2 levels (FIGS. 3B, 3C, 3G-3I, and 3J). Meanwhile, although 20% of the S-17 population activated the endogenous Sox2, only 0.1% could be reprogrammed into EGFP-positive colonies (FIGS. 3F and 7F), suggesting that sole activation of endogenous Sox2 is not determinant to pluripotent cell fate in the CRISPRa context. Further activating Oct4 promoter enhanced the efficiency of generating EGFP-positive colonies (FIG. 3K), supporting the cooperativity of multiple pluripotent genes reprogramming in pluripotency induction. In the Oct4 study, notably, remodeling of the enhancer region was required for pluripotency induction. Robust transcriptional activation was observed from the promoter remodeling, and modest gene activation from the enhancer remodeling. However, remodeling of enhancer seems essential for further induction of Oct4 at a later stage (FIG. 4C). This suggests that Oct4 promoter functions as a fast trigger, and the enhancer is a regulator required for latent but higher Oct4 transcription. Whether enhancer remodeling facilitated the establishment of promoter-enhancer loop as seen in naive mouse ES cells needs to be further investigated (Kagey et al., 2010). Another interesting point is that this enhancer is among the 231 superenhancers found specifically in pluripotent stem cells (Whyte et al., 2013). This disclosure provided functional evidence for superenhancer in pluripotency induction.

The generation of iPSCs with dCas9-SunTag-p300core revealed that histone acetylation plays an essential role in iPSC generation. Cellular reprogramming involves dynamic epigenetic changes, but whether reprogramming could be achieved through epigenetic manipulation of defined genomic sites was not previously known. In pluripotent stem cells, histone H3K27 acetylation is highly enriched at both the promoter and the enhancer of Oct4, which provides an entry to tackle this question by manipulating only one type of epigenetic modification. In the present disclosure, iPSCs were generated through dCas9-SunTag-p300core simultaneous targeting of the promoter and the enhancer. This also paved a way to change cell fate by site-specific manipulation of epigenetic modifications. Besides p300, several other epigenetic factors (i.e., Tet1, Dnmt3a, KRAB, and LSD1) have been verified as functional in epigenome editing for both activating or silencing genes (Kearns et al., 2015; Liu et al., 2016; Thakore et al., 2015). These expanding CRISPR tools give rise to more possibilities to manipulate cell fate by targeting different types of DNA and histone modifications in the future.

In summary, these data show that use of a CRISPRa system, here the SunTag system, precise remodeling of endogenous Oct4 or Sox2 gene locus is sufficient to initiate reprogramming towards pluripotency. These studies not only demonstrate the generation of iPSCs with CRISPR activation but also shed light on mechanistic understanding of cellular reprogramming. It is contemplated that the reprogramming strategy will also work in the generation of other cell types and in other model systems, such as human cells, which is further demonstrated in the following example.

Example 8. Generation of Human iPSCs with CRISPR Activation

Fibroblast Culture and Maintenance Human dermal fibroblasts isolated from neonatal foreskin (FTc1007; DFMF030811) were cultured on 0.1% porcine gelatin (Sigma-Aldrich, St. Louis, MO) in human fibroblast (hFib) growth medium: Dulbecco's Modified Eagle's Medium (DMEM) with 10% fetal bovine serum (FBS), with 1% Glutagro, 1% non-essential amino acids (NEAA), and 1% penicillin/streptomycin (Corning, Manassas, VA). Routine enzymatic passaging of fibroblasts was performed using Accutase dissociation reagent (Innovative Cell Technologies, Inc., San Diego, CA). Cells were maintained in 5% $CO_2$ and 5% $O_2$ at 37° C.

Plasmid Construction Lentiviral plasmids for human sgRNA expression were constructed using synthesized gBlocks® (Integrated DNA Technologies, Coralville, IA) containing the human U6 promoter, the specific gRNA, and appropriate homologous sequences for NEBuilder® (New England Biolabs Inc., Ipswich, MA), and were assembled into dCas9-Suntag-VP64 plasmids that were used in previous Examples. Specific gRNA sequences are listed in Table 3.

TABLE 3 gRNA sequences used for human genome targeting

| Gene Target | Human gRNA Sequence | SEQ ID |
|---|---|---|
| Oct4 promoter | GGGGGAGAAACTGAGGCGA | 57 |
| Oct4 promoter | TCTGTGGGGGACCTGCACTG | 58 |
| Sox2 promoter | GTGGCTGGCAGGCTGGCTCT | 59 |
| Klf4 promoter | GCTGCCATAGCAACGATGGA | 60 |
| c-Myc promoter | GGTTCCCAAAGCAGAGGGCG | 61 |
| Lin28 promoter | GTGTCAGAGACCGGAGTTGT | 62 |
| Nanog promoter | GATTAACTGAGAATTCACAA | 63 |
| EEA-motif | CCCAGCACTTTGGG | 64 |

Lentiviral Packaging HEK293T cells (ATCC CRL-3216) were plated 24 hours prior to transfection with lentiviral packaging plasmids to reach 70-80% confluence at the time of transfection. Transfection was performed using Lipofectamine 3000 transfection reagent (Life Technologies, Grand Island, NY). Medium was changed at 16 hours. Supernatant containing virus was collected on day 2 and day 3 post-transfection. Supernatant was then passed through a 0.45 μM filter and centrifuged at 20,000 xg for 1.5 hours at 4° C. Concentrated virus was resuspended in DMEM (Corning, Manassas, VA) and aliquots were stored at −80° C. All viruses were packaged independently and combined when used in two separate rounds of infection. All constructs were packaged for use with the dCas9-Suntag-VP64 system.

Virus Titration Titration of virus was performed using a series of dilutions in 293T cells seeded the previous day. Cells were infected in growth medium: DMEM (Corning, Manassas, VA) with 10% FBS (Life Technologies, Grand Island, NY) which was supplemented with 5 μg/mL polybrene (Millipore, Burlington, MA) and 10 mM HEPES (Corning, Manassas, VA). Cells were centrifuged for 90 minutes at 600 xg and then incubated for an additional 4-6 hours at which time the transduction medium was replaced with fresh growth medium. Titration was measured by detecting blue fluorescent protein (BFP) expressed from the sgRNA cassettes. Samples which exhibited between 1% and 20% positive signal for BFP expression were selected for titer calculation using the following formula:

$$\text{Titer}\left(\frac{\text{unit}}{\text{mL}}\right) = \frac{\text{Number of target cells (count on Day 1)} * \left[\frac{\% \text{ of } BEP \text{ positive cells}}{100}\right]}{\text{Volume of Lentivector (mL)}}$$

Human fibroblasts were reprogrammed using a CRISPR activation approach comprising an exemplary dCas9-Suntag-VP64 system and sgRNAs designed to target regulatory DNA elements associated with pluripotency gene transcription and embryonic genome activation. All lentiviral components for the Suntag system were packaged individually and introduced through two separate rounds of infection combining dCas9, VP64, and Tre3G in the first round, and the sgRNAs together in the second as described in the previous examples. Various concentrations of virus were used for comparison. Prior to the second round, to enrich the first-round infected cell population, transduced cells were treated with 1 μg/mL doxycycline for 24 hours and bulk-sorted for expression of GFP-VP64 and dCas9-10XGCN4-P2A-mCherry. For each round of infection, cells were seeded at a density of 5,000 or 10,000 cells/cm². Transduction was performed 24 hours after seeding in a medium containing: DMEM/F-12 (Corning, Manassas, VA) with 20% Knockout Serum Replacement (KOSR) (Life Technologies, Grand Island, NY), 1% Glutagro, 1% NEAA, 1% penicillin/streptomycin, 10 ng/mL basic human fibroblast growth factor (bFGF) (Life Technologies, Grand Island, NY), and 100 μM β-mercaptoethanol (Life Technologies, Grand Island, NY), supplemented with 4 μg/mL polybrene (Millipore, Burlington, MA) and 10 mM HEPES (Corning, Manassas, VA). Following infection, cells were centrifuged for 90 minutes at 600 xg and then incubated for an additional 4-6 hours at which time the infection medium was replaced to hFib medium containing 1 μg/mL doxycycline to begin induction (day 1). On day 5, cells were passaged using Accutase (Innovative Cell Technologies, Inc., San Diego, CA) onto 0.1% porcine gelatin (Sigma-Aldrich, St. Louis, MO) coated 6-well plates at a density of 7,500 cells/cm², doxycycline treatment was discontinued, and the medium was changed to one that comprises a TGFβ receptor inhibitor, a GSK3 inhibitor, a MEK inhibitor, and a ROCK inhibitor. On days 13 and 21, cells were again passaged using Accutase (Innovative Cell Technologies, Inc., San Diego, CA) and seeded onto Matrigel (Corning, Manassas, VA) coated 6-well plates at a density of 7,500 cells/cm², and the medium was changed to another medium comprising a GSK3 inhibitor, a MEK inhibitor, and a ROCK inhibitor, but not a TGFβ receptor inhibitor. Exemplary TGFβ receptor inhibitor, GSK3 inhibitor, MEK inhibitor, and ROCK inhibitor are known in the art (see, for example, WO2015134652). Specific examples include SB431542 and A-83-01 for TGFβ receptor inhibitor; PD0325901 and PD98059 for MEK inhibitor; CHIR99021 and BIO for GSK3 inhibitor; and thiazovivin and Y27632 for ROCK inhibitor.

Figure 9:
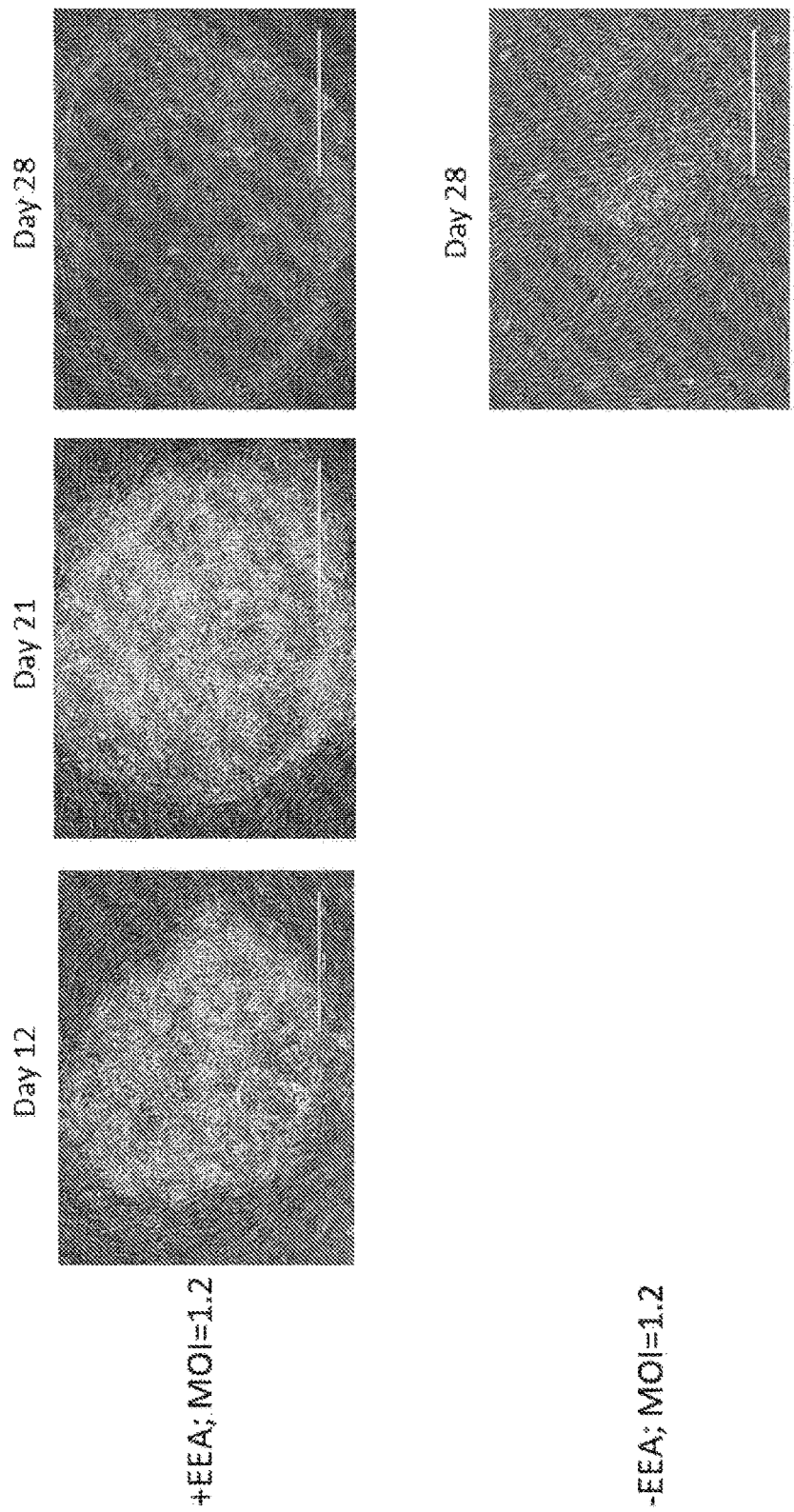
FIG. 9 demonstrates that CRISPRa generated human iPSC colonies that adopt and maintain pluripotent morphology over time. Top panels show that hiPSC morphological traits are more robust when EEA was included in iPSC generation as compared to hiPSCs generated without EEA (bottom panel on day 28).
Figure 10:
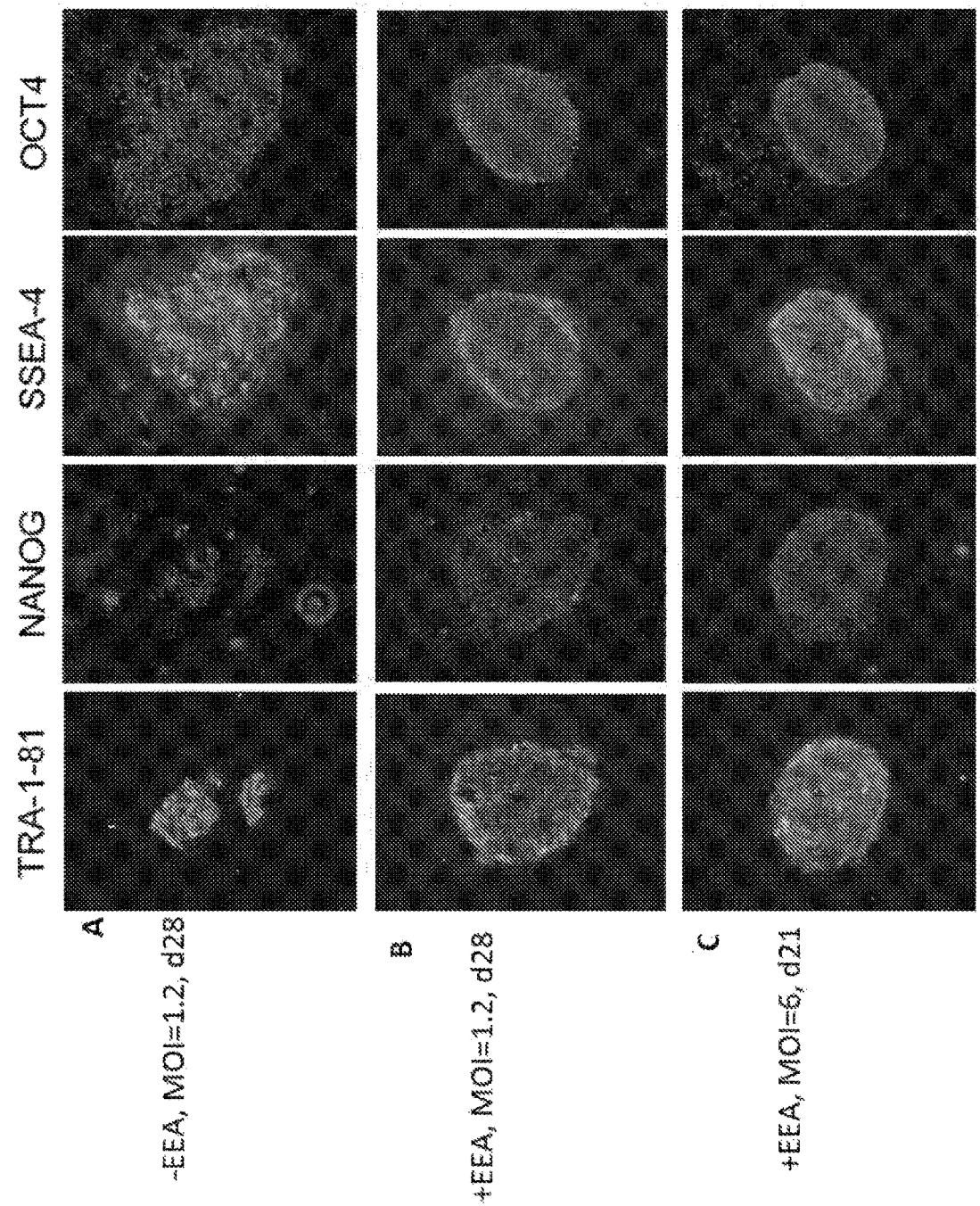
FIG. 10 demonstrates the expression of pluripotency gene in CRISPRa generated human iPSC colonies. A: day 28 hiPSCs generated without EEA, and MOI=1.2; and B: day 28 hiPSCs generated with EEA, and MOI=1.2; C: day 21 hiPSCs generated with EEA, and MOI=6.

As early as day 8, and over time, putative iPSCs were observed exhibiting high nuclear to cytoplasmic ratio and ESC-like colony morphology (FIG. 9). As shown in FIG. 9, the inclusion of EEA sgRNA in the CRISPR activation system seems to generate hiPSC clones with more robust morphological traits in comparison to CRISPRa-hiPSC clones obtained without EEA. The observation of morphology in CRISPRa-hiPSCs generated with or without EEA is consistent with the pluripotency gene expression level seen under the two conditions (see FIGS. 10 A and B). The iPSC colonies generated from CRISPRa system were further characterized based on expression of pluripotency markers and multilineage differentiation potential. Samples were collected for RNA analysis on days 10 and 21 and for flow cytometry on day 21. Cells were fixed for immunofluorescence staining on day 19, and for alkaline phosphatase staining on day 21. Media changes were performed every day or other day. Cells were cultured in 5% $CO_2$ and 5% $O_2$ at 37° C. Phase contrast imaging was done using EVOS FL Core Imaging System (Thermofisher, Waltham, MA). FIG. 10 shows that the expression of endogenous pluripotency genes such as TRA-1-81, NANOG, SSEA-4 and OCT4 are established in the CRISPRA-hiPSC colonies.

Figure 11:
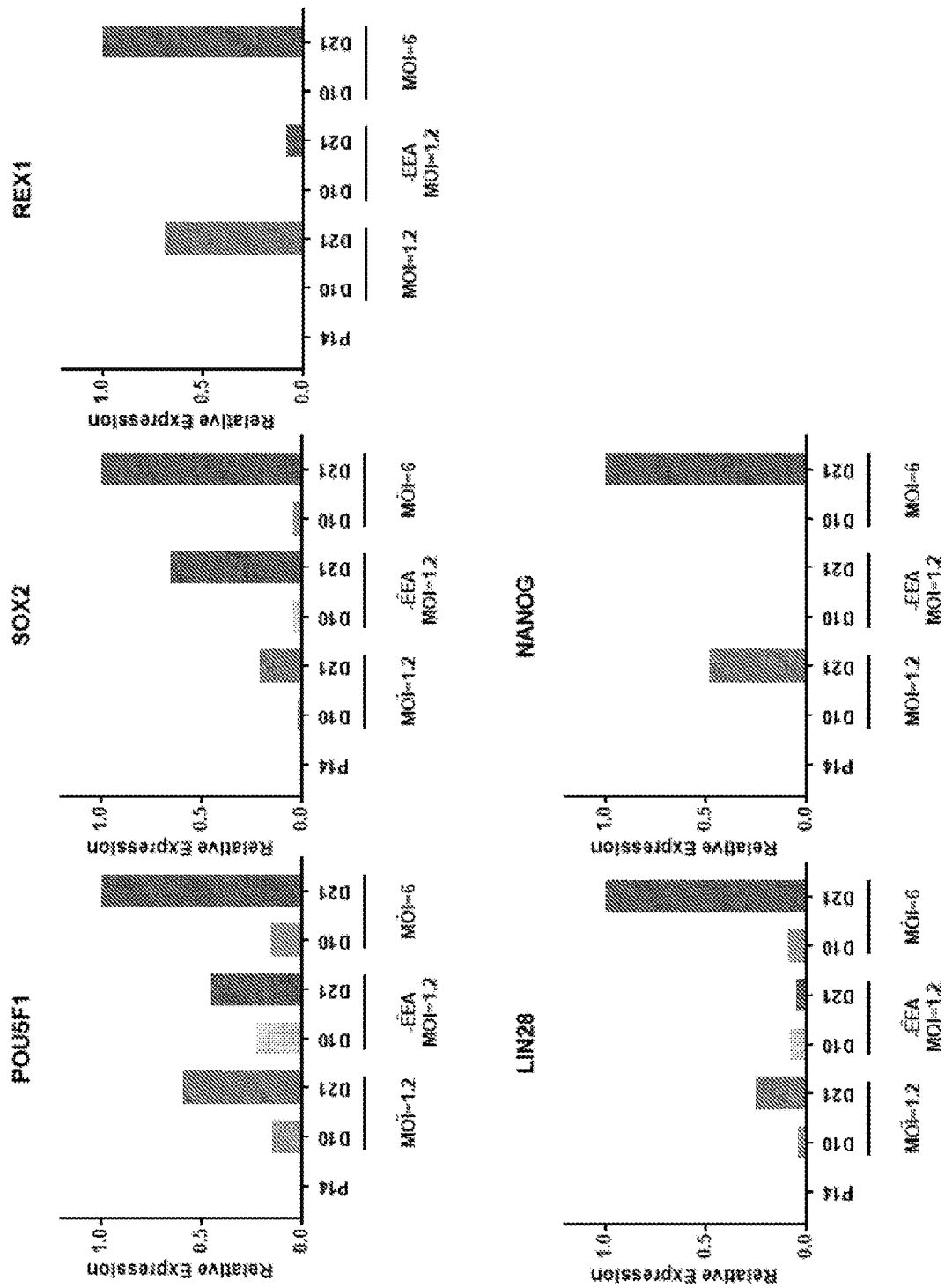
FIG. 11 demonstrates that the endogenous pluripotency program is activated in reprogrammed population over time, shown by increased expression of both targeted or non-targeted endogenous genes including Oct4 (Pou5f1), Sox2, Lin28, Nanog, and Rex1.
Figure 12:
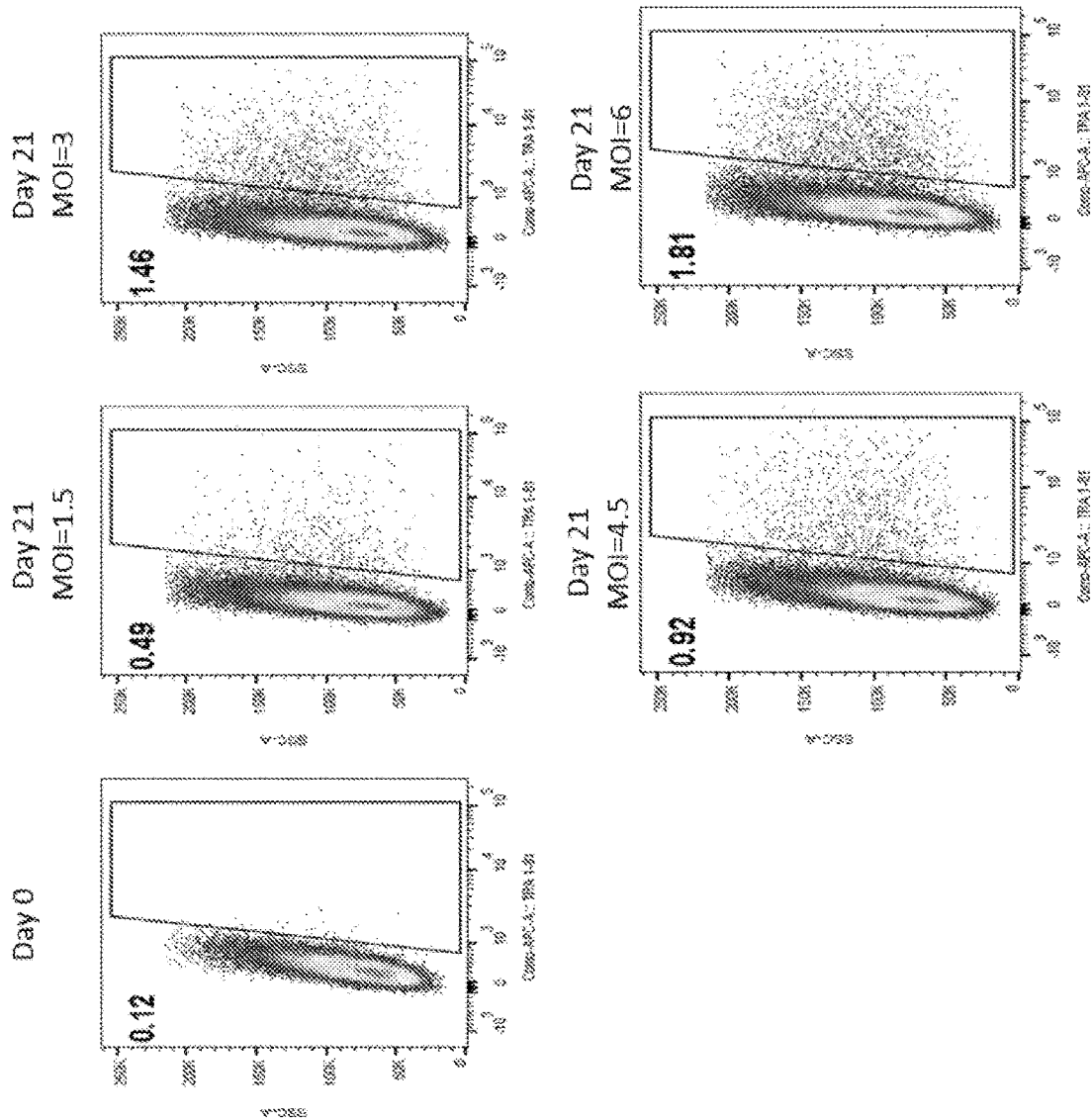
FIG. 12 demonstrates that the expression of pluripotency gene TRA-1-81 increases within reprogrammed population over time as shown by flow cytometry.

Total RNA was isolated using an RNeasy Plus Mini Kit (Qiagen, Valencia, CA). Quantitative PCR reactions were performed using TaqMan RNA-to-CT 1-Step Kit (Applied Biosystems, Foster City, CA) in a reaction volume of 20 μL per well of a 96-well plate, and analyzed on a StepOnePlus qPCR System and QuantStudio 3 qPCR System (Applied Biosystems, Foster City, CA). Reactions were performed in duplicate. Results were normalized against glyceraldehyde 3-phosphate dehydrogenase (GAPDH) as an internal reference gene. Relative gene expression was quantified using a 2ΔΔCt method and data were statistically analyzed using StepOne Software v2.3 and QuantStudio Design and Analysis Software v1.4.1 (Applied Biosystems, Foster City, CA), and GraphPad Prism 7 (GraphPad Software Inc., La Jolla, CA). Primers and probes for Nanog, Oct4, Lin28, Sox2, Rex1, and Gapdh were used for endogenous gene expression assessment. FIG. 11 shows that endogenous pluripotency program is activated in reprogrammed population over time, by activating not only the targeted endogenous genes, such as Oct4, Sox2, Lin28 and Nanog, but also those not targeted, for example, Rex1. The flow cytometry analysis of TRA-1-81 expression in FIG. 12 also demonstrates the established pluripotent state of the hiPSCs obtained through CRISPRa with various MOI conditions.

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

In addition, where the features or aspects of the invention are described in terms of Markush groups, those skilled in the art will recognize that the invention is also thereby described in terms of any individual member or subgroup members of the Markush group.

All publications, patent applications, patents and other references mentioned herein are expressly incorporated by reference in their entirety, to the same extent as if each were incorporated by reference individually. In case of conflict, the present specification, including definitions, will control.

REFERENCES

Arai, T., Takada, M., Ui, M., and Iba, H. (1999). Dose-dependent transduction of vesicular stomatitis virus G protein-pseudotyped retrovirus vector into human solid tumor cell lines and murine fibroblasts. Virology 260, 109-115.

Black, J. B., Adler, A. F., Wang, H. G., D'Ippolito, A. M., Hutchinson, H. A., Reddy, T. E., Pitt, G. S., Leong, K. W., and Gersbach, C. A. (2016). Targeted Epigenetic Remodeling of Endogenous Loci by CRISPR/Cas9-Based Transcriptional Activators Directly Converts Fibroblasts to Neuronal Cells. Cell Stem Cell 19, 406-414.

Buganim, Y., Faddah, D. A., Cheng, A. W., Itskovich, E., Markoulaki, S., Ganz, K., Klemm, S. L., van Oudenaarden, A., and Jaenisch, R. (2012). Single-cell expression analyses during cellular reprogramming reveal an early stochastic and a late hierarchic phase. Cell 150, 1209-1222.

Chakraborty, S., Ji, H., Kabadi, A. M., Gersbach, C. A., Christoforou, N., and Leong, K. W. (2014). A CRISPR/Cas9-based system for reprogramming cell lineage specification. Stem Cell Reports 3, 940-947.

Chavez, A., Scheiman, J., Vora, S., Pruitt, B. W., Tuttle, M., E, P. R. I., Lin, S., Kiani, S., Guzman, C. D., Wiegand, D. J., et al. (2015). Highly efficient Cas9-mediated transcriptional programming. Nat Methods 12, 326-328.

Cheng, A. W., Wang, H., Yang, H., Shi, L., Katz, Y., Theunissen, T. W., Rangarajan, S., Shivalila, C. S., Dadon, D. B., and Jaenisch, R. (2013). Multiplexed activation of endogenous genes by CRISPR-on, an RNA-guided transcriptional activator system. Cell Res 23, 1163-1171.

Cong, L., Ran, F. A., Cox, D., Lin, S., Barretto, R., Habib, N., Hsu, P. D., Wu, X., Jiang, W., Marraffini, L. A., et al. (2013). Multiplex genome engineering using CRISPR/Cas systems. Science 339, 819-823.

Di Stefano, B., Sardina, J. L., van Oevelen, C., Collombet, S., Kallin, E. M., Vicent, G. P., Lu, J., Thieffry, D., Beato, M., and Graf, T. (2014). C/EBPalpha poises B cells for rapid reprogramming into induced pluripotent stem cells. Nature 506, 235-239.

Gilbert, L. A., Larson, M. H., Morsut, L., Liu, Z., Brar, G. A., Torres, S. E., Stern-Ginossar, N., Brandman, O., Whitehead, E. H., Doudna, J. A., et al. (2013). CRISPR-mediated modular RNA-guided regulation of transcription in eukaryotes. Cell 154, 442-451.

Heng, J. C., Feng, B., Han, J., Jiang, J., Kraus, P., Ng, J. H., Orlov, Y. L., Huss, M., Yang, L., Lufkin, T., et al. (2010). The nuclear receptor Nr5a2 can replace Oct4 in the reprogramming of murine somatic cells to pluripotent cells. Cell Stem Cell 6, 167-174.

Hilton, I. B., D'Ippolito, A. M., Vockley, C. M., Thakore, P. I., Crawford, G. E., Reddy, T. E., and Gersbach, C. A. (2015). Epigenome editing by a CRISPR-Cas9-based acetyltransferase activates genes from promoters and enhancers. Nat Biotechnol 33, 510-517.

Hirai, H., Tani, T., and Kikyo, N. (2010). Structure and functions of powerful transactivators: VP16, MyoD and FoxA. Int J Dev Biol 54, 1589-1596.

Hu, J., Lei, Y., Wong, W. K., Liu, S., Lee, K. C., He, X., You, W., Zhou, R., Guo, J. T., Chen, X., et al. (2014). Direct activation of human and mouse Oct4 genes using engineered TALE and Cas9 transcription factors. Nucleic Acids Res 42, 4375-4390.

Jinek, M., Chylinski, K., Fonfara, I., Hauer, M., Doudna, J. A., and Charpentier, E. (2012). A programmable dual-RNA-guided DNA endonuclease in adaptive bacterial immunity. Science 337, 816-821.

Kagey, M. H., Newman, J. J., Bilodeau, S., Zhan, Y., Orlando, D. A., van Berkum, N. L., Ebmeier, C. C., Goossens, J., Rahl, P. B., Levine, S. S., et al. (2010). Mediator and cohesin connect gene expression and chromatin architecture. Nature 467, 430-435.

Kearns, N. A., Pham, H., Tabak, B., Genga, R. M., Silverstein, N. J., Garber, M., and Maehr, R. (2015). Functional annotation of native enhancers with a Cas9-histone demethylase fusion. Nat Methods 12, 401-403.

Konermann, S., Brigham, M. D., Trevino, A. E., Joung, J., Abudayyeh, O. O., Barcena, C., Hsu, P. D., Habib, N., Gootenberg, J. S., Nishimasu, H., et al. (2015). Genome-scale transcriptional activation by an engineered CRISPR-Cas9 complex. Nature 517, 583-588.

Liu, X. S., Wu, H., Ji, X., Stelzer, Y., Wu, X., Czauderna, S., Shu, J., Dadon, D., Young, R. A., and Jaenisch, R. (2016). Editing DNA Methylation in the Mammalian Genome. Cell 167, 233-247 e217.

Maekawa, M., Yamaguchi, K., Nakamura, T., Shibukawa, R., Kodanaka, I., Ichisaka, T., Kawamura, Y., Mochizuki, H., Goshima, N., and Yamanaka, S. (2011). Direct reprogramming of somatic cells is promoted by maternal transcription factor Glis1. Nature 474, 225-229.

Mali, P., Aach, J., Stranges, P. B., Esvelt, K. M., Moosburner, M., Kosuri, S., Yang, L., and Church, G. M. (2013a). CAS9 transcriptional activators for target specificity screening and paired nickases for cooperative genome engineering. Nat Biotechnol 31, 833-838.

Mali, P., Yang, L., Esvelt, K. M., Aach, J., Guell, M., DiCarlo, J. E., Norville, J. E., and Church, G. M. (2013b). RNA-guided human genome engineering via Cas9. Science 339, 823-826.

Polo, J. M., Anderssen, E., Walsh, R. M., Schwarz, B. A., Nefzger, C. M., Lim, S. M., Borkent, M., Apostolou, E., Alaei, S., Cloutier, J., et al. (2012). A molecular roadmap of reprogramming somatic cells into iPS cells. Cell 151, 1617-1632.

Polstein, L. R., Perez-Pinera, P., Kocak, D. D., Vockley, C. M., Bledsoe, P., Song, L., Safi, A., Crawford, G. E., Reddy, T. E., and Gersbach, C. A. (2015). Genome-wide specificity of DNA binding, gene regulation, and chromatin remodeling by TALE- and CRISPR/Cas9-based transcriptional activators. Genome Res 25, 1158-1169.

Smith, Z. D., Sindhu, C., and Meissner, A. (2016). Molecular features of cellular reprogramming and development. Nat Rev Mol Cell Biol 17, 139-154.

Soufi, A., Donahue, G., and Zaret, K. S. (2012). Facilitators and impediments of the pluripotency reprogramming factors' initial engagement with the genome. Cell 151, 994-1004.

Stemmer, M., Thumberger, T., Del Sol Keyer, M., Wittbrodt, J., and Mateo, J. L. (2015). CCTop: An Intuitive, Flexible and Reliable CRISPR/Cas9 Target Prediction Tool. PLoS One 10, e0124633.

Szabo, P. E., Hubner, K., Scholer, H., and Mann, J. R. (2002). Allele-specific expression of imprinted genes in mouse migratory primordial germ cells. Mech Dev 115, 157-160.

Takahashi, K., and Yamanaka, S. (2006). Induction of pluripotent stem cells from mouse embryonic and adult fibroblast cultures by defined factors. Cell 126, 663-676.

Tanenbaum, M. E., Gilbert, L. A., Qi, L. S., Weissman, J. S., and Vale, R. D. (2014). A protein-tagging system for signal amplification in gene expression and fluorescence imaging. Cell 159, 635-646.

Thakore, P. I., D'Ippolito, A. M., Song, L., Safi, A., Shivakumar, N. K., Kabadi, A. M., Reddy, T. E., Crawford, G. E., and Gersbach, C. A. (2015). Highly specific epigenome editing by CRISPR-Cas9 repressors for silencing of distal regulatory elements. Nat Methods 12, 1143-1149.

Wei, Z., Gao, F., Kim, S., Yang, H., Lyu, J., An, W., Wang, K., and Lu, W. (2013). Klf4 organizes long-range chromosomal interactions with the oct4 locus in reprogramming and pluripotency. Cell Stem Cell 13, 36-47.

Whyte, W. A., Orlando, D. A., Hnisz, D., Abraham, B. J., Lin, C. Y., Kagey, M. H., Rahl, P. B., Lee, T. I., and Young, R. A. (2013). Master transcription factors and mediator establish super-enhancers at key cell identity genes. Cell 153, 307-319.

Yeom, Y. I., Fuhrmann, G., Ovitt, C. E., Brehm, A., Ohbo, K., Gross, M., Hubner, K., and Scholer, H. R. (1996). Germline regulatory element of Oct-4 specific for the totipotent cycle of embryonal cells. Development 122, 881-894.

Zalatan, J. G., Lee, M. E., Almeida, R., Gilbert, L. A., Whitehead, E. H., La Russa, M., Tsai, J. C., Weissman, J. S., Dueber, J. E., Qi, L. S., et al. (2015). Engineering complex synthetic transcriptional programs with CRISPR RNA scaffolds. Cell 160, 339-350.

What is claimed is:

1. A method of generating a population of induced pluripotent stem cells (iPSCs) comprising:
   (a) targeting at least one endogenous gene locus using at least two single guide RNA (sgRNAs) in a population of non-iPSCs; and
   (b) remodeling the at least one endogenous gene locus in the non-iPSCs using a CRISPR activation system and the at least two sgRNAs;
   thereby generating the population of iPSCs;
   wherein the at least one endogenous gene locus comprises Oct4, and wherein a first sgRNA of the at least two sgRNAs targets an Oct4 promoter and a second sgRNA of the at least two sgRNAs targets an Oct4 enhancer; and
   wherein the number of iPSCs in the population of iPSCs is increased as compared to remodeling without the second sgRNA.

2. The method of claim 1, wherein
   (a) the at least one endogenous gene locus further comprises Sox2, Klf4, c-Myc, Nr5a2, Glis1, Cebpa, Lin28, Nanog, or any combination thereof;
   (b) the at least one endogenous gene locus further comprises a combination of Sox2, Klf4, c-Myc, Lin28, and Nanog;
   (c) the at least one endogenous gene locus further comprises Sox2; and/or
   (d) the at least two sgRNAs further target Sox2 promoter, Klf4 promoter, c-Myc promoter, Lin28 promoter, Nanog promoter, EEA-motif, or a combination thereof.

3. The method of claim 2, wherein
   (a) the sgRNA targeting the Oct4 promoter comprises an RNA sequence corresponding to any one of SEQ ID NOs: 1-6, 57, and 58;
   (b) the sgRNA targeting the Oct4 enhancer comprises an RNA sequence corresponding to any one of SEQ ID NOs: 7-11;
   (c) the sgRNA targeting the Sox2 promoter comprises an RNA sequence corresponding to any one of SEQ ID NOs: 12-21, and 59;
   (d) the sgRNA targeting the Klf4 promoter comprises an RNA sequence corresponding to any one of SEQ ID NOs: 22-31, and 60;
   (e) the sgRNA targeting the c-Myc promoter comprises an RNA sequence corresponding to any one of SEQ ID NOs: 32-41, and 61;
   (f) the sgRNA targeting the Nr5a2 gene comprises an RNA sequence corresponding to any one of SEQ ID NOs: 42-45;
   (g) the sgRNA targeting the Glis1 gene comprises an RNA sequence corresponding to any one of SEQ ID NOs: 46-50;
   (h) the sgRNA targeting the Cebpa gene comprises an RNA sequence corresponding to any one of SEQ ID NOs: 51-56;
   (i) the sgRNA targeting the Lin28 promoter comprises an RNA sequence corresponding to SEQ ID NO: 62;
   (j) the sgRNA targeting the Nanog promoter comprises an RNA sequence corresponding to SEQ ID NO: 63; and/or
   (k) the sgRNA targeting the EEA-motif comprises an RNA sequence corresponding to SEQ ID NO: 64.

4. The method of claim 1, wherein the CRISPR activation system comprises
   (a) deactivated CRISPR-associated nuclease fused with at least one transcriptional activator; and optionally (b) a tandem array of peptides that links deactivated CRISPR-associated nuclease to the at least one transcriptional activator.

5. The method of claim 4, wherein
(a) the CRISPR activation system comprises deactivated Cas9 (dCas9);
(b) the tandem array of peptide is a SunTag array; and/or
(c) the at least one transcriptional activator comprises herpes simplex VP16, a tetramer of VP16 (VP64), or p65.

6. The method of claim 4, wherein the CRISPR activation system comprises the tandem array of peptides that links deactivated CRISPR-associated nuclease to the at least one transcriptional activator.

7. The method of claim 1, wherein the population of non-iPSCs comprise:
(a) a fibroblast, a skin cell, a cord blood cell, a peripheral blood cell, or a renal epithelial cell;
(b) a mammalian cell; and/or
(c) a human cell.

8. The method of claim 1, further comprising
(c) contacting the population of non-iPSCs with small molecules comprising a TGFβR inhibitor, a GSK3 inhibitor, a MEK inhibitor and a ROCK inhibitor; and optionally
(d) contacting the generated population of iPSCs with small molecules comprising a GSK3 inhibitor, a MEK inhibitor and a ROCK inhibitor, but not a TGFβR inhibitor.

9. The method of claim 1, wherein the remodeling of the endogenous gene locus yields a 100-fold or greater level of gene expression in comparison to without the remodeling.

10. A method of generating a population of iPSCs comprising:
(a) targeting at least two endogenous loci using of a Sox2 promoter targeting sgRNA, an Oct4 promoter targeting sgRNA, and an Oct4 enhancer targeting sgRNA in a population of non-iPSCs, and
(b) remodeling the at least two endogenous gene loci using a CRISPR activation system and the Sox2 promoter targeting sgRNA, the Oct4 promoter targeting sgRNA, and the Oct4 enhancer targeting sgRNA; thereby generating the population of iPSCs;
wherein the number of iPSCs in the population of iPSCs is increased as compared to remodeling without the Oct4 enhancer targeting sgRNA.

11. A method of generating a population of iPSCs comprising:
(a) targeting at least one endogenous gene locus using at least two sgRNAs in a population of non-iPSCs, and
(b) remodeling the at least one endogenous gene locus in the non-iPSCs using a CRISPR activation system and the at least two sgRNAs to generate the population of iPSCs;
wherein the at least one endogenous gene locus comprises Oct4, and wherein a first sgRNA of the at least two sgRNAs targets an Oct4 promoter and a second sgRNA of the at least two sgRNAs targets an Oct4 enhancer, wherein the number of iPSCs in the population of iPSCs is increased as compared to remodeling without the second sgRNA, and
wherein the CRISPR activation system comprises:
(1) a dCas9;
(2) a SunTag array fused to the dCas9; and
(3) at least one acetyltransferase activity domain of p300 (p300core) attached to the SunTag array.

12. The method of claim 11, wherein
(a) the at least one endogenous gene locus further comprises Sox2, Klf4, c-Myc, Nanog, Lin28, Nr5a2, Glis1, Cebpa, or any combination thereof;
(b) the sgRNA targeting the Oct4 promoter comprises an RNA sequence corresponding to any one of SEQ ID NOs: 1-6, 57, and 58;
(c) the sgRNA targeting the Oct4 enhancer comprises an RNA sequence corresponding to any one of SEQ ID NOs: 7-11;
(d) the at least two sgRNAs further target Sox2 promoter, and the sgRNA targeting the Sox2 promoter comprises an RNA sequence corresponding to any one of SEQ ID NOs: 12-21, and 59;
(e) the at least two sgRNAs further target Klf4 promoter, and the sgRNA targeting the Klf4 promoter comprises an RNA sequence corresponding to any one of SEQ ID NOs: 22-31 and 60;
(f) the at least two sgRNAs further target c-Myc promoter, and the sgRNA targeting the c-Myc promoter comprises an RNA sequence corresponding to any one of SEQ ID NOs: 32-41, and 61;
(g) the at least two sgRNAs further target Nr5a2 gene, and the sgRNA targeting the Nr5a2 promoter comprises an RNA sequence corresponding to any one of SEQ ID NOs: 42-45;
(h) the at least two sgRNAs further target Glis1 gene, and the sgRNA targeting the Glis1 promoter comprises an RNA sequence corresponding to any one of SEQ ID NOs: 46-50;
(i) the at least two sgRNAs further target Cebpa gene, and the sgRNA targeting the Cebpa promoter comprises an RNA sequence corresponding to any one of SEQ ID NOs: 51-56;
(j) the at least two sgRNAs further target Lin28 promoter, and the sgRNA targeting the Lin28 promoter comprises an RNA sequence corresponding to SEQ ID NO: 62;
(k) the at least two sgRNAs further target Nanog promoter, and the sgRNA targeting the Nanog promoter comprises an RNA sequence corresponding to SEQ ID NO: 63; and/or
(l) the at least two sgRNAs further target EEA-motif, and the sgRNA targeting the EEA-motif comprises an RNA sequence corresponding to SEQ ID NO: 64.

13. The method of claim 11, wherein
(a) the population of non-iPSCs comprise a fibroblast, a skin cell, a cord blood cell, a peripheral blood cell, or a renal epithelial cell;
(b) the population of non-iPSCs comprise a mammalian cell; and/or
(c) the population of non-iPSCs comprise a human cell.

* * * * *

SEQUENCE LISTING

```
<160> NUMBER OF SEQ ID NOS: 175

<210> SEQ ID NO 1
<211> LENGTH: 20
<212> TYPE: DNA
<213> ORGANISM: Artificial Sequence
<220> FEATURE:
<223> OTHER INFORMATION: sgRNA O-321 for targeting Oct4 promoter

<400> SEQUENCE: 1
cagcccactc agccatcctc                                               20

<210> SEQ ID NO 2
<211> LENGTH: 20
<212> TYPE: DNA
<213> ORGANISM: Artificial Sequence
<220> FEATURE:
<223> OTHER INFORMATION: sgRNA O-248 for targeting Oct4 promoter

<400> SEQUENCE: 2
atccgagcaa ctggtttgtg                                               20

<210> SEQ ID NO 3
<211> LENGTH: 20
<212> TYPE: DNA
<213> ORGANISM: Artificial Sequence
<220> FEATURE:
<223> OTHER INFORMATION: sgRNA O-226 for targeting Oct4 promoter

<400> SEQUENCE: 3
gtgtccggtg acccaaggca                                               20

<210> SEQ ID NO 4
<211> LENGTH: 20
<212> TYPE: DNA
<213> ORGANISM: Artificial Sequence
<220> FEATURE:
<223> OTHER INFORMATION: sgRNA O-157 for targeting Oct4 promoter

<400> SEQUENCE: 4
ggacaggaca acccttagga                                               20

<210> SEQ ID NO 5
<211> LENGTH: 20
<212> TYPE: DNA
<213> ORGANISM: Artificial Sequence
<220> FEATURE:
```

```
<223> OTHER INFORMATION: sgRNA O-127 for targeting Oct4 promoter

<400> SEQUENCE: 5
aacctccgtc tggaagacac                                              20

<210> SEQ ID NO 6
<211> LENGTH: 20
<212> TYPE: DNA
<213> ORGANISM: Artificial Sequence
<220> FEATURE:
<223> OTHER INFORMATION: sgRNA O-71 for targeting Oct4 promoter

<400> SEQUENCE: 6
gggtggagga gcagagctgt                                              20

<210> SEQ ID NO 7
<211> LENGTH: 20
<212> TYPE: DNA
<213> ORGANISM: Artificial Sequence
<220> FEATURE:
<223> OTHER INFORMATION: sgRNA O-2135 for targeting Oct4 enhancer

<400> SEQUENCE: 7
agacaggact gctgggctgc                                              20

<210> SEQ ID NO 8
<211> LENGTH: 20
<212> TYPE: DNA
<213> ORGANISM: Artificial Sequence
<220> FEATURE:
<223> OTHER INFORMATION: sgRNA O-2066 for targeting Oct4 enhancer

<400> SEQUENCE: 8
gccctgggag gaactgggtg                                              20

<210> SEQ ID NO 9
<211> LENGTH: 20
<212> TYPE: DNA
<213> ORGANISM: Artificial Sequence
<220> FEATURE:
<223> OTHER INFORMATION: sgRNA O-2014 for targeting Oct4 enhancer

<400> SEQUENCE: 9
cccagggagg ttgagagttc                                              20

<210> SEQ ID NO 10
<211> LENGTH: 20
<212> TYPE: DNA
<213> ORGANISM: Artificial Sequence
<220> FEATURE:
<223> OTHER INFORMATION: sgRNA O-1965 for targeting Oct4 enhancer

<400> SEQUENCE: 10
gcatgatagc tctgccctgg                                              20

<210> SEQ ID NO 11
<211> LENGTH: 20
<212> TYPE: DNA
<213> ORGANISM: Artificial Sequence
<220> FEATURE:
<223> OTHER INFORMATION: sgRNA O-1914 for targeting Oct4 enhancer

<400> SEQUENCE: 11
taaggaaggg ctaggacgag                                              20
```

```
<210> SEQ ID NO 12
<211> LENGTH: 20
<212> TYPE: DNA
<213> ORGANISM: Artificial Sequence
<220> FEATURE:
<223> OTHER INFORMATION: sgRNA S-430 for targeting Sox2 promoter

<400> SEQUENCE: 12
caactagtat ttcaggaagc                                              20

<210> SEQ ID NO 13
<211> LENGTH: 20
<212> TYPE: DNA
<213> ORGANISM: Artificial Sequence
<220> FEATURE:
<223> OTHER INFORMATION: sgRNA S-398 for targeting Sox2 promoter

<400> SEQUENCE: 13
gcaaggccca tgggtggttc                                              20

<210> SEQ ID NO 14
<211> LENGTH: 20
<212> TYPE: DNA
<213> ORGANISM: Artificial Sequence
<220> FEATURE:
<223> OTHER INFORMATION: sgRNA S-348 for targeting Sox2 promoter

<400> SEQUENCE: 14
cttggataca taagggtgga                                              20

<210> SEQ ID NO 15
<211> LENGTH: 20
<212> TYPE: DNA
<213> ORGANISM: Artificial Sequence
<220> FEATURE:
<223> OTHER INFORMATION: sgRNA S-326 for targeting Sox2 promoter

<400> SEQUENCE: 15
agagccaata ttccgtagca                                              20

<210> SEQ ID NO 16
<211> LENGTH: 20
<212> TYPE: DNA
<213> ORGANISM: Artificial Sequence
<220> FEATURE:
<223> OTHER INFORMATION: sgRNA S-276 for targeting Sox2 promoter

<400> SEQUENCE: 16
tttacccact tccttcgaac                                              20

<210> SEQ ID NO 17
<211> LENGTH: 20
<212> TYPE: DNA
<213> ORGANISM: Artificial Sequence
<220> FEATURE:
<223> OTHER INFORMATION: sgRNA S-262 for targeting Sox2 promoter

<400> SEQUENCE: 17
cacggcgcac gcctgttcga                                              20

<210> SEQ ID NO 18
<211> LENGTH: 20
<212> TYPE: DNA
<213> ORGANISM: Artificial Sequence
<220> FEATURE:
<223> OTHER INFORMATION: sgRNA S-192 for targeting Sox2 promoter
```

<400> SEQUENCE: 18
gcgggcccgc agccggccgc                                              20

<210> SEQ ID NO 19
<211> LENGTH: 20
<212> TYPE: DNA
<213> ORGANISM: Artificial Sequence
<220> FEATURE:
<223> OTHER INFORMATION: sgRNA S-148 for targeting Sox2 promoter

<400> SEQUENCE: 19
gcgctctgct gggctcggct                                              20

<210> SEQ ID NO 20
<211> LENGTH: 20
<212> TYPE: DNA
<213> ORGANISM: Artificial Sequence
<220> FEATURE:
<223> OTHER INFORMATION: sgRNA S-136 for targeting Sox2 promoter

<400> SEQUENCE: 20
gctcggctcg gcggcgcggc                                              20

<210> SEQ ID NO 21
<211> LENGTH: 20
<212> TYPE: DNA
<213> ORGANISM: Artificial Sequence
<220> FEATURE:
<223> OTHER INFORMATION: sgRNA S-84 for targeting Sox2 promoter

<400> SEQUENCE: 21
gcgaggctgg gctcgggcgc                                              20

<210> SEQ ID NO 22
<211> LENGTH: 20
<212> TYPE: DNA
<213> ORGANISM: Artificial Sequence
<220> FEATURE:
<223> OTHER INFORMATION: sgRNA K-475 for targeting Klf4 promoter

<400> SEQUENCE: 22
ggacaagcgc gtacgcgagc                                              20

<210> SEQ ID NO 23
<211> LENGTH: 20
<212> TYPE: DNA
<213> ORGANISM: Artificial Sequence
<220> FEATURE:
<223> OTHER INFORMATION: sgRNA K-380 for targeting Klf4 promoter

<400> SEQUENCE: 23
tgggctcgaa agtcctgcca                                              20

<210> SEQ ID NO 24
<211> LENGTH: 20
<212> TYPE: DNA
<213> ORGANISM: Artificial Sequence
<220> FEATURE:
<223> OTHER INFORMATION: sgRNA K-309 for targeting Klf4 promoter

<400> SEQUENCE: 24
ccacgccgta ctcccagcgc                                              20

<210> SEQ ID NO 25
<211> LENGTH: 20

```
<212> TYPE: DNA
<213> ORGANISM: Artificial Sequence
<220> FEATURE:
<223> OTHER INFORMATION: sgRNA K-293 for targeting Klf4 promoter

<400> SEQUENCE: 25
ggcgacggcg gctccggcgc                                                    20

<210> SEQ ID NO 26
<211> LENGTH: 20
<212> TYPE: DNA
<213> ORGANISM: Artificial Sequence
<220> FEATURE:
<223> OTHER INFORMATION: sgRNA K-271 for targeting Klf4 promoter

<400> SEQUENCE: 26
caccgccgcc ggcgtcagca                                                    20

<210> SEQ ID NO 27
<211> LENGTH: 20
<212> TYPE: DNA
<213> ORGANISM: Artificial Sequence
<220> FEATURE:
<223> OTHER INFORMATION: sgRNA K-249 for targeting Klf4 promoter

<400> SEQUENCE: 27
gctccagccc gccagctgcc                                                    20

<210> SEQ ID NO 28
<211> LENGTH: 20
<212> TYPE: DNA
<213> ORGANISM: Artificial Sequence
<220> FEATURE:
<223> OTHER INFORMATION: sgRNA K-232 for targeting Klf4 promoter

<400> SEQUENCE: 28
gcctggctgg cgtcacggcc                                                    20

<210> SEQ ID NO 29
<211> LENGTH: 20
<212> TYPE: DNA
<213> ORGANISM: Artificial Sequence
<220> FEATURE:
<223> OTHER INFORMATION: sgRNA K-171 for targeting Klf4 promoter

<400> SEQUENCE: 29
taaacaaact ccgcgcacgt                                                    20

<210> SEQ ID NO 30
<211> LENGTH: 20
<212> TYPE: DNA
<213> ORGANISM: Artificial Sequence
<220> FEATURE:
<223> OTHER INFORMATION: sgRNA K-147 for targeting Klf4 promoter

<400> SEQUENCE: 30
gctaccatgg caacgcgcag                                                    20

<210> SEQ ID NO 31
<211> LENGTH: 20
<212> TYPE: DNA
<213> ORGANISM: Artificial Sequence
<220> FEATURE:
<223> OTHER INFORMATION: sgRNA K-67 for targeting Klf4 promoter

<400> SEQUENCE: 31
```
cgcgcgccgc cacagggagg                                                      20

<210> SEQ ID NO 32
<211> LENGTH: 20
<212> TYPE: DNA
<213> ORGANISM: Artificial Sequence
<220> FEATURE:
<223> OTHER INFORMATION: sgRNA M-444 for targeting cMyc promoter

<400> SEQUENCE: 32
gacgaacgaa tgagttatct                                                      20

<210> SEQ ID NO 33
<211> LENGTH: 20
<212> TYPE: DNA
<213> ORGANISM: Artificial Sequence
<220> FEATURE:
<223> OTHER INFORMATION: sgRNA M-395 for targeting cMyc promoter

<400> SEQUENCE: 33
ccaggcgtct ctctaaggct                                                      20

<210> SEQ ID NO 34
<211> LENGTH: 20
<212> TYPE: DNA
<213> ORGANISM: Artificial Sequence
<220> FEATURE:
<223> OTHER INFORMATION: sgRNA M-347 for targeting cMyc promoter

<400> SEQUENCE: 34
acacaatacg ccatgtaccc                                                      20

<210> SEQ ID NO 35
<211> LENGTH: 20
<212> TYPE: DNA
<213> ORGANISM: Artificial Sequence
<220> FEATURE:
<223> OTHER INFORMATION: sgRNA M-305 for targeting cMyc promoter

<400> SEQUENCE: 35
tgcggtgact gatatacgca                                                      20

<210> SEQ ID NO 36
<211> LENGTH: 20
<212> TYPE: DNA
<213> ORGANISM: Artificial Sequence
<220> FEATURE:
<223> OTHER INFORMATION: sgRNA M-249 for targeting cMyc promoter

<400> SEQUENCE: 36
acaaccgtac agaaagggaa                                                      20

<210> SEQ ID NO 37
<211> LENGTH: 20
<212> TYPE: DNA
<213> ORGANISM: Artificial Sequence
<220> FEATURE:
<223> OTHER INFORMATION: sgRNA M-242 for targeting cMyc promoter

<400> SEQUENCE: 37
tagtcctttc cctttctgta                                                      20

<210> SEQ ID NO 38
<211> LENGTH: 20
<212> TYPE: DNA
<213> ORGANISM: Artificial Sequence

```
<220> FEATURE:
<223> OTHER INFORMATION: sgRNA M-175 for targeting cMyc promoter

<400> SEQUENCE: 38
cgctattact gtttacaccc                                              20

<210> SEQ ID NO 39
<211> LENGTH: 20
<212> TYPE: DNA
<213> ORGANISM: Artificial Sequence
<220> FEATURE:
<223> OTHER INFORMATION: sgRNA M-154 for targeting cMyc promoter

<400> SEQUENCE: 39
cagcccagta ctccggctcc                                              20

<210> SEQ ID NO 40
<211> LENGTH: 20
<212> TYPE: DNA
<213> ORGANISM: Artificial Sequence
<220> FEATURE:
<223> OTHER INFORMATION: sgRNA M-124 for targeting cMyc promoter

<400> SEQUENCE: 40
ggctcctcct cctctttccc                                              20

<210> SEQ ID NO 41
<211> LENGTH: 20
<212> TYPE: DNA
<213> ORGANISM: Artificial Sequence
<220> FEATURE:
<223> OTHER INFORMATION: sgRNA M-82 for targeting cMyc promoter

<400> SEQUENCE: 41
cgagttccca aagcagaggg                                              20

<210> SEQ ID NO 42
<211> LENGTH: 20
<212> TYPE: DNA
<213> ORGANISM: Artificial Sequence
<220> FEATURE:
<223> OTHER INFORMATION: sgRNA Nr-404 for targeting Nr5a2 promoter

<400> SEQUENCE: 42
ccgccctctc acggaagcgg                                              20

<210> SEQ ID NO 43
<211> LENGTH: 20
<212> TYPE: DNA
<213> ORGANISM: Artificial Sequence
<220> FEATURE:
<223> OTHER INFORMATION: sgRNA Nr-157 for targeting Nr5a2 promoter

<400> SEQUENCE: 43
gggcgtggag cccaggaagg                                              20

<210> SEQ ID NO 44
<211> LENGTH: 20
<212> TYPE: DNA
<213> ORGANISM: Artificial Sequence
<220> FEATURE:
<223> OTHER INFORMATION: sgRNA Nr-61 for targeting Nr5a2 promoter

<400> SEQUENCE: 44
gatggaatgt tcaagtggga                                              20
```

-continued

<210> SEQ ID NO 45
<211> LENGTH: 20
<212> TYPE: DNA
<213> ORGANISM: Artificial Sequence
<220> FEATURE:
<223> OTHER INFORMATION: sgRNA Nr-60 for targeting Nr5a2 promoter

<400> SEQUENCE: 45
tcccacttga acattccatc                                                  20

<210> SEQ ID NO 46
<211> LENGTH: 20
<212> TYPE: DNA
<213> ORGANISM: Artificial Sequence
<220> FEATURE:
<223> OTHER INFORMATION: sgRNA G-419 for targeting Glis1 promoter

<400> SEQUENCE: 46
gggaggagca gaatcccgcc                                                  20

<210> SEQ ID NO 47
<211> LENGTH: 20
<212> TYPE: DNA
<213> ORGANISM: Artificial Sequence
<220> FEATURE:
<223> OTHER INFORMATION: sgRNA G-215 for targeting Glis1 promoter

<400> SEQUENCE: 47
gggctgccgg accaagccaa                                                  20

<210> SEQ ID NO 48
<211> LENGTH: 20
<212> TYPE: DNA
<213> ORGANISM: Artificial Sequence
<220> FEATURE:
<223> OTHER INFORMATION: sgRNA G-179 for targeting Glis1 promoter

<400> SEQUENCE: 48
gagcggctgt gggcagcagc                                                  20

<210> SEQ ID NO 49
<211> LENGTH: 20
<212> TYPE: DNA
<213> ORGANISM: Artificial Sequence
<220> FEATURE:
<223> OTHER INFORMATION: sgRNA G-118 for targeting Glis1 promoter

<400> SEQUENCE: 49
ggccgtggcg gtggcggcgg                                                  20

<210> SEQ ID NO 50
<211> LENGTH: 20
<212> TYPE: DNA
<213> ORGANISM: Artificial Sequence
<220> FEATURE:
<223> OTHER INFORMATION: sgRNA G-47 for targeting Glis1 promoter

<400> SEQUENCE: 50
gccgcgggcg cagcggctcg                                                  20

<210> SEQ ID NO 51
<211> LENGTH: 20
<212> TYPE: DNA
<213> ORGANISM: Artificial Sequence
<220> FEATURE:
<223> OTHER INFORMATION: sgRNA C-345 for targeting Cebpa

```
<400> SEQUENCE: 51
gctcccgggc tccctagtgt                                               20

<210> SEQ ID NO 52
<211> LENGTH: 20
<212> TYPE: DNA
<213> ORGANISM: Artificial Sequence
<220> FEATURE:
<223> OTHER INFORMATION: sgRNA C-282 for targeting Cebpa

<400> SEQUENCE: 52
cacacacgtg gtccgtggtt                                               20

<210> SEQ ID NO 53
<211> LENGTH: 20
<212> TYPE: DNA
<213> ORGANISM: Artificial Sequence
<220> FEATURE:
<223> OTHER INFORMATION: sgRNA C-177 for targeting Cebpa

<400> SEQUENCE: 53
gtgctagtgg agagagatcg                                               20

<210> SEQ ID NO 54
<211> LENGTH: 20
<212> TYPE: DNA
<213> ORGANISM: Artificial Sequence
<220> FEATURE:
<223> OTHER INFORMATION: sgRNA C-135 for targeting Cebpa

<400> SEQUENCE: 54
ggaaagtcac aggagaaggc                                               20

<210> SEQ ID NO 55
<211> LENGTH: 20
<212> TYPE: DNA
<213> ORGANISM: Artificial Sequence
<220> FEATURE:
<223> OTHER INFORMATION: sgRNA C-100 for targeting Cebpa

<400> SEQUENCE: 55
gccagtagga tggtgcctgc                                               20

<210> SEQ ID NO 56
<211> LENGTH: 20
<212> TYPE: DNA
<213> ORGANISM: Artificial Sequence
<220> FEATURE:
<223> OTHER INFORMATION: sgRNA C-70 for targeting Cebpa

<400> SEQUENCE: 56
cgagacccgt ttggacacca                                               20

<210> SEQ ID NO 57
<211> LENGTH: 18
<212> TYPE: DNA
<213> ORGANISM: Artificial Sequence
<220> FEATURE:
<223> OTHER INFORMATION: human gRNA sequence for targeting OCT4 promoter

<400> SEQUENCE: 57
ggggagaaac tgaggcga                                                 18

<210> SEQ ID NO 58
```

```
<211> LENGTH: 20
<212> TYPE: DNA
<213> ORGANISM: Artificial Sequence
<220> FEATURE:
<223> OTHER INFORMATION: human gRNA sequence for targeting OCT4 promoter

<400> SEQUENCE: 58
tctgtggggg acctgcactg                                          20

<210> SEQ ID NO 59
<211> LENGTH: 20
<212> TYPE: DNA
<213> ORGANISM: Artificial Sequence
<220> FEATURE:
<223> OTHER INFORMATION: human gRNA sequence for targeting Sox2 promoter

<400> SEQUENCE: 59
gtggctggca ggctggctct                                          20

<210> SEQ ID NO 60
<211> LENGTH: 20
<212> TYPE: DNA
<213> ORGANISM: Artificial Sequence
<220> FEATURE:
<223> OTHER INFORMATION: human gRNA sequence for targeting Klf4 promoter

<400> SEQUENCE: 60
gctgccatag caacgatgga                                          20

<210> SEQ ID NO 61
<211> LENGTH: 20
<212> TYPE: DNA
<213> ORGANISM: Artificial Sequence
<220> FEATURE:
<223> OTHER INFORMATION: human gRNA sequence for targeting c-Myc
      promoter

<400> SEQUENCE: 61
ggttcccaaa gcagagggcg                                          20

<210> SEQ ID NO 62
<211> LENGTH: 20
<212> TYPE: DNA
<213> ORGANISM: Artificial Sequence
<220> FEATURE:
<223> OTHER INFORMATION: human gRNA sequence for targeting Lin28A
      promoter

<400> SEQUENCE: 62
gtgtcagaga ccggagttgt                                          20

<210> SEQ ID NO 63
<211> LENGTH: 20
<212> TYPE: DNA
<213> ORGANISM: Artificial Sequence
<220> FEATURE:
<223> OTHER INFORMATION: human gRNA sequence for targeting NANOG
      promoter

<400> SEQUENCE: 63
gattaactga gaattcacaa                                          20

<210> SEQ ID NO 64
<211> LENGTH: 14
<212> TYPE: DNA
<213> ORGANISM: Artificial Sequence
<220> FEATURE:
```

<223> OTHER INFORMATION: human gRNA sequence for targeting EEA-motif

<400> SEQUENCE: 64
cccagcactt tggg                                                    14

<210> SEQ ID NO 65
<211> LENGTH: 17
<212> TYPE: DNA
<213> ORGANISM: Artificial Sequence
<220> FEATURE:
<223> OTHER INFORMATION: Forward primer for qPCR of Gene Oct4 (total)

<400> SEQUENCE: 65
atcgccaatc agcttgg                                                 17

<210> SEQ ID NO 66
<211> LENGTH: 23
<212> TYPE: DNA
<213> ORGANISM: Artificial Sequence
<220> FEATURE:
<223> OTHER INFORMATION: Reverse primer for qPCR of Gene Oct4 (total)

<400> SEQUENCE: 66
agaaccatac tcgaaccaca tcc                                          23

<210> SEQ ID NO 67
<211> LENGTH: 20
<212> TYPE: DNA
<213> ORGANISM: Artificial Sequence
<220> FEATURE:
<223> OTHER INFORMATION: Forward primer for qPCR of Gene Oct4
      (endogenous)

<400> SEQUENCE: 67
taggtgagcc gtctttccac                                              20

<210> SEQ ID NO 68
<211> LENGTH: 20
<212> TYPE: DNA
<213> ORGANISM: Artificial Sequence
<220> FEATURE:
<223> OTHER INFORMATION: Reverse primer for qPCR of Gene Oct4
      (endogenous)

<400> SEQUENCE: 68
gcttagccag gttcgaggat                                              20

<210> SEQ ID NO 69
<211> LENGTH: 20
<212> TYPE: DNA
<213> ORGANISM: Artificial Sequence
<220> FEATURE:
<223> OTHER INFORMATION: Forward primer for qPCR of Gene Sox2 (total)

<400> SEQUENCE: 69
acagatgcaa ccgatgcacc                                              20

<210> SEQ ID NO 70
<211> LENGTH: 20
<212> TYPE: DNA
<213> ORGANISM: Artificial Sequence
<220> FEATURE:
<223> OTHER INFORMATION: Reverse primer for qPCR of Gene Sox2 (total)

<400> SEQUENCE: 70
tggagttgta ctgcagggcg                                              20

<210> SEQ ID NO 71
<211> LENGTH: 19
<212> TYPE: DNA
<213> ORGANISM: Artificial Sequence
<220> FEATURE:
<223> OTHER INFORMATION: Forward primer for qPCR of Gene Sox2
      (endogenous)

<400> SEQUENCE: 71
gagaagtttg gagcccgag                                              19

<210> SEQ ID NO 72
<211> LENGTH: 21
<212> TYPE: DNA
<213> ORGANISM: Artificial Sequence
<220> FEATURE:
<223> OTHER INFORMATION: Reverse primer for qPCR of Gene Sox2
      (endogenous)

<400> SEQUENCE: 72
gatctggcgg agaatagttg g                                           21

<210> SEQ ID NO 73
<211> LENGTH: 20
<212> TYPE: DNA
<213> ORGANISM: Artificial Sequence
<220> FEATURE:
<223> OTHER INFORMATION: Forward primer for qPCR of Gene Klf4

<400> SEQUENCE: 73
gcacacctgc gaactcacac                                             20

<210> SEQ ID NO 74
<211> LENGTH: 21
<212> TYPE: DNA
<213> ORGANISM: Artificial Sequence
<220> FEATURE:
<223> OTHER INFORMATION: Reverse primer for qPCR of Gene Klf4

<400> SEQUENCE: 74
ccgtcccagt cacagtggta a                                           21

<210> SEQ ID NO 75
<211> LENGTH: 19
<212> TYPE: DNA
<213> ORGANISM: Artificial Sequence
<220> FEATURE:
<223> OTHER INFORMATION: Forward primer for qPCR of Gene c-Myc

<400> SEQUENCE: 75
ccaccagcag cgactctga                                              19

<210> SEQ ID NO 76
<211> LENGTH: 21
<212> TYPE: DNA
<213> ORGANISM: Artificial Sequence
<220> FEATURE:
<223> OTHER INFORMATION: Reverse primer for qPCR of Gene c-Myc

<400> SEQUENCE: 76
tgcctcttct ccacagacac c                                           21

<210> SEQ ID NO 77
<211> LENGTH: 20
<212> TYPE: DNA

```
<213> ORGANISM: Artificial Sequence
<220> FEATURE:
<223> OTHER INFORMATION: Forward primer for qPCR of Gene Nr5a2

<400> SEQUENCE: 77
atgggaagga agggacaatc                                                20

<210> SEQ ID NO 78
<211> LENGTH: 20
<212> TYPE: DNA
<213> ORGANISM: Artificial Sequence
<220> FEATURE:
<223> OTHER INFORMATION: Reverse primer for qPCR of Gene Nr5a2

<400> SEQUENCE: 78
atacaaactc ccgctgatcg                                                20

<210> SEQ ID NO 79
<211> LENGTH: 20
<212> TYPE: DNA
<213> ORGANISM: Artificial Sequence
<220> FEATURE:
<223> OTHER INFORMATION: Forward primer for qPCR of Gene Glis1

<400> SEQUENCE: 79
ctccaagcat ccacactgtt                                                20

<210> SEQ ID NO 80
<211> LENGTH: 20
<212> TYPE: DNA
<213> ORGANISM: Artificial Sequence
<220> FEATURE:
<223> OTHER INFORMATION: Reverse primer for qPCR of Gene Glis1

<400> SEQUENCE: 80
gacaggatgc ctgaagcaag                                                20

<210> SEQ ID NO 81
<211> LENGTH: 21
<212> TYPE: DNA
<213> ORGANISM: Artificial Sequence
<220> FEATURE:
<223> OTHER INFORMATION: Forward primer for qPCR of Gene Cebpa

<400> SEQUENCE: 81
caagaacagc aacgagtacc g                                              21

<210> SEQ ID NO 82
<211> LENGTH: 21
<212> TYPE: DNA
<213> ORGANISM: Artificial Sequence
<220> FEATURE:
<223> OTHER INFORMATION: Reverse primer for qPCR of Gene Cebpa

<400> SEQUENCE: 82
gtcactggtc aactccagca c                                              21

<210> SEQ ID NO 83
<211> LENGTH: 22
<212> TYPE: DNA
<213> ORGANISM: Artificial Sequence
<220> FEATURE:
<223> OTHER INFORMATION: Forward primer for qPCR of Gene Nanog

<400> SEQUENCE: 83
cctccagcag atgcaagaac tc                                             22
```

<210> SEQ ID NO 84
<211> LENGTH: 23
<212> TYPE: DNA
<213> ORGANISM: Artificial Sequence
<220> FEATURE:
<223> OTHER INFORMATION: Reverse primer for qPCR of Gene Nanog

<400> SEQUENCE: 84
cttcaaccac tggttttct gcc                                             23

<210> SEQ ID NO 85
<211> LENGTH: 22
<212> TYPE: DNA
<213> ORGANISM: Artificial Sequence
<220> FEATURE:
<223> OTHER INFORMATION: Forward primer for qPCR of Gene Dppa2

<400> SEQUENCE: 85
tcaacgagaa ccaatctgag ga                                             22

<210> SEQ ID NO 86
<211> LENGTH: 21
<212> TYPE: DNA
<213> ORGANISM: Artificial Sequence
<220> FEATURE:
<223> OTHER INFORMATION: Reverse primer for qPCR of Gene Dppa2

<400> SEQUENCE: 86
gcgtagcgta gtctgtgttt g                                              21

<210> SEQ ID NO 87
<211> LENGTH: 20
<212> TYPE: DNA
<213> ORGANISM: Artificial Sequence
<220> FEATURE:
<223> OTHER INFORMATION: Forward primer for qPCR of Gene Esrrb

<400> SEQUENCE: 87
ctcgccaact cagattcgat                                                20

<210> SEQ ID NO 88
<211> LENGTH: 20
<212> TYPE: DNA
<213> ORGANISM: Artificial Sequence
<220> FEATURE:
<223> OTHER INFORMATION: Reverse primer for qPCR of Gene Esrrb

<400> SEQUENCE: 88
agaagtgttg cacggctttg                                                20

<210> SEQ ID NO 89
<211> LENGTH: 23
<212> TYPE: DNA
<213> ORGANISM: Artificial Sequence
<220> FEATURE:
<223> OTHER INFORMATION: Forward primer for qPCR of Gene Fgf4

<400> SEQUENCE: 89
cgtggtgagc atcttcggag tgg                                            23

<210> SEQ ID NO 90
<211> LENGTH: 23
<212> TYPE: DNA
<213> ORGANISM: Artificial Sequence
<220> FEATURE:

```
<223> OTHER INFORMATION: Reverse primer for qPCR of Gene Fgf4

<400> SEQUENCE: 90
ccttcttggt ccgcccgttc tta                                              23

<210> SEQ ID NO 91
<211> LENGTH: 21
<212> TYPE: DNA
<213> ORGANISM: Artificial Sequence
<220> FEATURE:
<223> OTHER INFORMATION: Forward primer for qPCR of Gene Lin28

<400> SEQUENCE: 91
tgttctgtat tgggagtgag c                                                21

<210> SEQ ID NO 92
<211> LENGTH: 19
<212> TYPE: DNA
<213> ORGANISM: Artificial Sequence
<220> FEATURE:
<223> OTHER INFORMATION: Reverse primer for qPCR of Gene Lin28

<400> SEQUENCE: 92
gcttgcattc cttggcatg                                                   19

<210> SEQ ID NO 93
<211> LENGTH: 22
<212> TYPE: DNA
<213> ORGANISM: Artificial Sequence
<220> FEATURE:
<223> OTHER INFORMATION: Forward primer for qPCR of Gene Tet1

<400> SEQUENCE: 93
tctcactcat gttgcgggac cc                                               22

<210> SEQ ID NO 94
<211> LENGTH: 22
<212> TYPE: DNA
<213> ORGANISM: Artificial Sequence
<220> FEATURE:
<223> OTHER INFORMATION: Reverse primer for qPCR of Gene Tet1

<400> SEQUENCE: 94
cgtcggagtt gaaatgggcg aa                                               22

<210> SEQ ID NO 95
<211> LENGTH: 19
<212> TYPE: DNA
<213> ORGANISM: Artificial Sequence
<220> FEATURE:
<223> OTHER INFORMATION: Forward primer for qPCR of Gene Utf1

<400> SEQUENCE: 95
tgtcccggtg actacgtct                                                   19

<210> SEQ ID NO 96
<211> LENGTH: 21
<212> TYPE: DNA
<213> ORGANISM: Artificial Sequence
<220> FEATURE:
<223> OTHER INFORMATION: Reverse primer for qPCR of Gene Utf1

<400> SEQUENCE: 96
cccagaagta gctccgtctc t                                                21
```

```
<210> SEQ ID NO 97
<211> LENGTH: 19
<212> TYPE: DNA
<213> ORGANISM: Artificial Sequence
<220> FEATURE:
<223> OTHER INFORMATION: Forward primer for qPCR of Gene Actin

<400> SEQUENCE: 97 atggaggga atacagccc                                              19

<210> SEQ ID NO 98
<211> LENGTH: 20
<212> TYPE: DNA
<213> ORGANISM: Artificial Sequence
<220> FEATURE:
<223> OTHER INFORMATION: Reverse primer for qPCR of Gene Actin

<400> SEQUENCE: 98
ttctttgcag ctccttcgtt                                            20

<210> SEQ ID NO 99
<211> LENGTH: 20
<212> TYPE: DNA
<213> ORGANISM: Artificial Sequence
<220> FEATURE:
<223> OTHER INFORMATION: Forward primer for qPCR of Gene Oct4
      (ChIP-2.7k)

<400> SEQUENCE: 99
tggcctggaa ctcagaaatc                                            20

<210> SEQ ID NO 100
<211> LENGTH: 20
<212> TYPE: DNA
<213> ORGANISM: Artificial Sequence
<220> FEATURE:
<223> OTHER INFORMATION: Reverse primer for qPCR of Gene Oct4
      (ChIP-2.7k)

<400> SEQUENCE: 100
tctgccccct ttaagagtca                                            20

<210> SEQ ID NO 101
<211> LENGTH: 20
<212> TYPE: DNA
<213> ORGANISM: Artificial Sequence
<220> FEATURE:
<223> OTHER INFORMATION: Forward primer for qPCR of Gene Oct4
      (ChIP-1.4k)

<400> SEQUENCE: 101
cccaggctca gaactctgtc                                            20

<210> SEQ ID NO 102
<211> LENGTH: 20
<212> TYPE: DNA
<213> ORGANISM: Artificial Sequence
<220> FEATURE:
<223> OTHER INFORMATION: Reverse primer for qPCR of Gene Oct4
      (ChIP-1.4k)

<400> SEQUENCE: 102
tgctcctaca ccatgctctg                                            20

<210> SEQ ID NO 103
<211> LENGTH: 20
<212> TYPE: DNA
```

```
<213> ORGANISM: Artificial Sequence
<220> FEATURE:
<223> OTHER INFORMATION: Forward primer for qPCR of Gene Oct4
      (ChIP-0.2k)

<400> SEQUENCE: 103
ttgaaaatga aggcctcctg                                              20

<210> SEQ ID NO 104
<211> LENGTH: 20
<212> TYPE: DNA
<213> ORGANISM: Artificial Sequence
<220> FEATURE:
<223> OTHER INFORMATION: Reverse primer for qPCR of Gene Oct4
      (ChIP-0.2k)

<400> SEQUENCE: 104
agcgctatct gcctgtgtct                                              20

<210> SEQ ID NO 105
<211> LENGTH: 22
<212> TYPE: DNA
<213> ORGANISM: Artificial Sequence
<220> FEATURE:
<223> OTHER INFORMATION: Forward primer for qPCR of Gene Sox2
      (ChIP-0.4k)

<400> SEQUENCE: 105
cttgggtcta acttctcgtc tg                                           22

<210> SEQ ID NO 106
<211> LENGTH: 19
<212> TYPE: DNA
<213> ORGANISM: Artificial Sequence
<220> FEATURE:
<223> OTHER INFORMATION: Reverse primer for qPCR of Gene Sox2
      (ChIP-0.4k)

<400> SEQUENCE: 106
gtgtgccatt gtttctgcg                                               19

<210> SEQ ID NO 107
<211> LENGTH: 21
<212> TYPE: DNA
<213> ORGANISM: Artificial Sequence
<220> FEATURE:
<223> OTHER INFORMATION: Forward primer for qPCR of Gene Nanog
      (ChIP-0.5k)

<400> SEQUENCE: 107
ccaacttact aaggtagccc g                                            21

<210> SEQ ID NO 108
<211> LENGTH: 20
<212> TYPE: DNA
<213> ORGANISM: Artificial Sequence
<220> FEATURE:
<223> OTHER INFORMATION: Reverse primer for qPCR of Gene Nanog
      (ChIP-0.5k)

<400> SEQUENCE: 108
ctttcagcac tcagcgtttc                                              20

<210> SEQ ID NO 109
<211> LENGTH: 21
<212> TYPE: DNA
<213> ORGANISM: Artificial Sequence
```

```
<220> FEATURE:
<223> OTHER INFORMATION: Forward primer for qPCR of Gene Rex1
      (ChIP-0.5k)

<400> SEQUENCE: 109
ccccgctaca aagtacacta g                                              21

<210> SEQ ID NO 110
<211> LENGTH: 22
<212> TYPE: DNA
<213> ORGANISM: Artificial Sequence
<220> FEATURE:
<223> OTHER INFORMATION: Reverse primer for qPCR of Gene Rex1
      (ChIP-0.5k)

<400> SEQUENCE: 110
ctagaccgtt tgtagtcagt gg                                             22

<210> SEQ ID NO 111
<211> LENGTH: 21
<212> TYPE: DNA
<213> ORGANISM: Artificial Sequence
<220> FEATURE:
<223> OTHER INFORMATION: Forward primer for qPCR of Gene Ctnnbl1

<400> SEQUENCE: 111
agaacgacag tgagaaggtt g                                              21

<210> SEQ ID NO 112
<211> LENGTH: 22
<212> TYPE: DNA
<213> ORGANISM: Artificial Sequence
<220> FEATURE:
<223> OTHER INFORMATION: Reverse primer for qPCR of Gene Ctnnbl1

<400> SEQUENCE: 112
cattgtctat gatctcccca cg                                             22

<210> SEQ ID NO 113
<211> LENGTH: 21
<212> TYPE: DNA
<213> ORGANISM: Artificial Sequence
<220> FEATURE:
<223> OTHER INFORMATION: Forward primer for qPCR of Gene Tbc1d22b

<400> SEQUENCE: 113
ttctgtttat ctgggccatc c                                              21

<210> SEQ ID NO 114
<211> LENGTH: 21
<212> TYPE: DNA
<213> ORGANISM: Artificial Sequence
<220> FEATURE:
<223> OTHER INFORMATION: Reverse primer for qPCR of Gene Tbc1d22b

<400> SEQUENCE: 114
gtcaaagttc tccacgtcct c                                              21

<210> SEQ ID NO 115
<211> LENGTH: 19
<212> TYPE: DNA
<213> ORGANISM: Artificial Sequence
<220> FEATURE:
<223> OTHER INFORMATION: Forward primer for qPCR of Gene Phf20

<400> SEQUENCE: 115
```
agtgtgaaga gtgccagtg                                                  19

<210> SEQ ID NO 116
<211> LENGTH: 21
<212> TYPE: DNA
<213> ORGANISM: Artificial Sequence
<220> FEATURE:
<223> OTHER INFORMATION: Reverse primer for qPCR of Gene Phf20

<400> SEQUENCE: 116
ctcagccact ccttgtcata c                                               21

<210> SEQ ID NO 117
<211> LENGTH: 20
<212> TYPE: DNA
<213> ORGANISM: Artificial Sequence
<220> FEATURE:
<223> OTHER INFORMATION: Forward primer for qPCR of Gene Rgr

<400> SEQUENCE: 117
gtacctatac gcagccatcg                                                 20

<210> SEQ ID NO 118
<211> LENGTH: 21
<212> TYPE: DNA
<213> ORGANISM: Artificial Sequence
<220> FEATURE:
<223> OTHER INFORMATION: Reverse primer for qPCR of Gene Rgr

<400> SEQUENCE: 118
ttcctctaca gaccatctcc c                                               21

<210> SEQ ID NO 119
<211> LENGTH: 22
<212> TYPE: DNA
<213> ORGANISM: Artificial Sequence
<220> FEATURE:
<223> OTHER INFORMATION: Forward primer for qPCR of Gene Zp3r

<400> SEQUENCE: 119
actgtcctga aatatacctg cc                                              22

<210> SEQ ID NO 120
<211> LENGTH: 21
<212> TYPE: DNA
<213> ORGANISM: Artificial Sequence
<220> FEATURE:
<223> OTHER INFORMATION: Reverse primer for qPCR of Gene Zp3r

<400> SEQUENCE: 120
actttcccat tgaccaactc g                                               21

<210> SEQ ID NO 121
<211> LENGTH: 19
<212> TYPE: DNA
<213> ORGANISM: Artificial Sequence
<220> FEATURE:
<223> OTHER INFORMATION: Forward primer for qPCR of Gene Lmbr1

<400> SEQUENCE: 121
gcggtgggta tgaaaggag                                                  19

<210> SEQ ID NO 122
<211> LENGTH: 22
<212> TYPE: DNA
<213> ORGANISM: Artificial Sequence

```
<220> FEATURE:
<223> OTHER INFORMATION: Reverse primer for qPCR of Gene Lmbr1

<400> SEQUENCE: 122
aggaaacgat gtagagaatg gc                                        22

<210> SEQ ID NO 123
<211> LENGTH: 20
<212> TYPE: DNA
<213> ORGANISM: Artificial Sequence
<220> FEATURE:
<223> OTHER INFORMATION: Forward primer for qPCR of Gene D130040H23Rik

<400> SEQUENCE: 123
gacctacagc aacctcactg                                           20

<210> SEQ ID NO 124
<211> LENGTH: 20
<212> TYPE: DNA
<213> ORGANISM: Artificial Sequence
<220> FEATURE:
<223> OTHER INFORMATION: Reverse primer for qPCR of Gene D130040H23Rik

<400> SEQUENCE: 124
gcaaaggctt taccacactg                                           20

<210> SEQ ID NO 125
<211> LENGTH: 21
<212> TYPE: DNA
<213> ORGANISM: Artificial Sequence
<220> FEATURE:
<223> OTHER INFORMATION: Forward primer for qPCR of Gene Gli3

<400> SEQUENCE: 125
ttcagcaagt ggttcctatg g                                         21

<210> SEQ ID NO 126
<211> LENGTH: 21
<212> TYPE: DNA
<213> ORGANISM: Artificial Sequence
<220> FEATURE:
<223> OTHER INFORMATION: Reverse primer for qPCR of Gene Gli3

<400> SEQUENCE: 126
ctgtcggctt aggatctgtt g                                         21

<210> SEQ ID NO 127
<211> LENGTH: 20
<212> TYPE: DNA
<213> ORGANISM: Artificial Sequence
<220> FEATURE:
<223> OTHER INFORMATION: Forward primer for qPCR of Gene Vav3

<400> SEQUENCE: 127
tgtcaaaccc tctccatgtg                                           20

<210> SEQ ID NO 128
<211> LENGTH: 20
<212> TYPE: DNA
<213> ORGANISM: Artificial Sequence
<220> FEATURE:
<223> OTHER INFORMATION: Reverse primer for qPCR of Gene Vav3

<400> SEQUENCE: 128
tctttggtcc tgtgccttac                                           20
```

```
<210> SEQ ID NO 129
<211> LENGTH: 20
<212> TYPE: DNA
<213> ORGANISM: Artificial Sequence
<220> FEATURE:
<223> OTHER INFORMATION: Forward primer for qPCR of Gene Renbp

<400> SEQUENCE: 129
cacagtgaag ccatgattgc                                               20

<210> SEQ ID NO 130
<211> LENGTH: 20
<212> TYPE: DNA
<213> ORGANISM: Artificial Sequence
<220> FEATURE:
<223> OTHER INFORMATION: Reverse primer for qPCR of Gene Renbp

<400> SEQUENCE: 130
agccaaacca ttccccatac                                               20

<210> SEQ ID NO 131
<211> LENGTH: 21
<212> TYPE: DNA
<213> ORGANISM: Artificial Sequence
<220> FEATURE:
<223> OTHER INFORMATION: Forward primer for qPCR of Gene Rab11fip4os1

<400> SEQUENCE: 131
gtctctgatg gaaggatgct g                                             21

<210> SEQ ID NO 132
<211> LENGTH: 22
<212> TYPE: DNA
<213> ORGANISM: Artificial Sequence
<220> FEATURE:
<223> OTHER INFORMATION: Reverse primer for qPCR of Gene Rab11fip4os1

<400> SEQUENCE: 132
gccttaattt gttttgcctc gg                                            22

<210> SEQ ID NO 133
<211> LENGTH: 22
<212> TYPE: DNA
<213> ORGANISM: Artificial Sequence
<220> FEATURE:
<223> OTHER INFORMATION: Forward primer for qPCR of Gene Styk1

<400> SEQUENCE: 133
gaaaatcatg aagagaccca gc                                            22

<210> SEQ ID NO 134
<211> LENGTH: 21
<212> TYPE: DNA
<213> ORGANISM: Artificial Sequence
<220> FEATURE:
<223> OTHER INFORMATION: Reverse primer for qPCR of Gene Styk1

<400> SEQUENCE: 134
catcggcaga tctagaagca g                                             21

<210> SEQ ID NO 135
<211> LENGTH: 21
<212> TYPE: DNA
<213> ORGANISM: Artificial Sequence
<220> FEATURE:
<223> OTHER INFORMATION: Forward primer for qPCR of Gene Cyb5a
```

<400> SEQUENCE: 135
cagaagcaca aagacagcaa g                                              21

<210> SEQ ID NO 136
<211> LENGTH: 21
<212> TYPE: DNA
<213> ORGANISM: Artificial Sequence
<220> FEATURE:
<223> OTHER INFORMATION: Reverse primer for qPCR of Gene Cyb5a

<400> SEQUENCE: 136
aaattctcgg tagcatcacc c                                              21

<210> SEQ ID NO 137
<211> LENGTH: 22
<212> TYPE: DNA
<213> ORGANISM: Artificial Sequence
<220> FEATURE:
<223> OTHER INFORMATION: Forward primer for qPCR of Gene Zak

<400> SEQUENCE: 137
gtaatggaga agtggatcgt gg                                             22

<210> SEQ ID NO 138
<211> LENGTH: 21
<212> TYPE: DNA
<213> ORGANISM: Artificial Sequence
<220> FEATURE:
<223> OTHER INFORMATION: Reverse primer for qPCR of Gene Zak

<400> SEQUENCE: 138
ttcgttctgt cccactgtat g                                              21

<210> SEQ ID NO 139
<211> LENGTH: 21
<212> TYPE: DNA
<213> ORGANISM: Artificial Sequence
<220> FEATURE:
<223> OTHER INFORMATION: Forward primer for qPCR of Gene Tec

<400> SEQUENCE: 139
gaaacagcaa catccccaaa g                                              21

<210> SEQ ID NO 140
<211> LENGTH: 20
<212> TYPE: DNA
<213> ORGANISM: Artificial Sequence
<220> FEATURE:
<223> OTHER INFORMATION: Reverse primer for qPCR of Gene Tec

<400> SEQUENCE: 140
cttccccttt gtactgaccg                                                20

<210> SEQ ID NO 141
<211> LENGTH: 20
<212> TYPE: DNA
<213> ORGANISM: Artificial Sequence
<220> FEATURE:
<223> OTHER INFORMATION: Forward primer for qPCR of Gene Fbn2

<400> SEQUENCE: 141
acctgaatcc caacatctgc                                                20

<210> SEQ ID NO 142

```
<211> LENGTH: 20
<212> TYPE: DNA
<213> ORGANISM: Artificial Sequence
<220> FEATURE:
<223> OTHER INFORMATION: Reverse primer for qPCR of Gene Fbn2

<400> SEQUENCE: 142
ccaatctcac actcgtccac                                           20

<210> SEQ ID NO 143
<211> LENGTH: 21
<212> TYPE: DNA
<213> ORGANISM: Artificial Sequence
<220> FEATURE:
<223> OTHER INFORMATION: Forward primer for qPCR of Gene Zfp653

<400> SEQUENCE: 143
ccacctctat agccagcatt g                                         21

<210> SEQ ID NO 144
<211> LENGTH: 19
<212> TYPE: DNA
<213> ORGANISM: Artificial Sequence
<220> FEATURE:
<223> OTHER INFORMATION: Reverse primer for qPCR of Gene Zfp653

<400> SEQUENCE: 144
ccatccactt ctgcctctg                                            19

<210> SEQ ID NO 145
<211> LENGTH: 20
<212> TYPE: DNA
<213> ORGANISM: Artificial Sequence
<220> FEATURE:
<223> OTHER INFORMATION: Forward primer for qPCR of Gene Ptgis

<400> SEQUENCE: 145
aggatgaagg aaaagcacgg                                           20

<210> SEQ ID NO 146
<211> LENGTH: 21
<212> TYPE: DNA
<213> ORGANISM: Artificial Sequence
<220> FEATURE:
<223> OTHER INFORMATION: Reverse primer for qPCR of Gene Ptgis

<400> SEQUENCE: 146
catgaggaag atggcatagg g                                         21

<210> SEQ ID NO 147
<211> LENGTH: 25
<212> TYPE: DNA
<213> ORGANISM: Artificial Sequence
<220> FEATURE:
<223> OTHER INFORMATION: Forward primer for qPCR of Gene Alg10b

<400> SEQUENCE: 147
caacttctac ttgctgtatt tgctc                                     25

<210> SEQ ID NO 148
<211> LENGTH: 24
<212> TYPE: DNA
<213> ORGANISM: Artificial Sequence
<220> FEATURE:
<223> OTHER INFORMATION: Reverse primer for qPCR of Gene Alg10b

<400> SEQUENCE: 148
```

```
gacccagctt ctgtatagta aagg                                            24

<210> SEQ ID NO 149
<211> LENGTH: 21
<212> TYPE: DNA
<213> ORGANISM: Artificial Sequence
<220> FEATURE:
<223> OTHER INFORMATION: Forward primer for qPCR of Gene Sh3pxd2a

<400> SEQUENCE: 149
aggaaatcag tgtggttgtc c                                               21

<210> SEQ ID NO 150
<211> LENGTH: 21
<212> TYPE: DNA
<213> ORGANISM: Artificial Sequence
<220> FEATURE:
<223> OTHER INFORMATION: Reverse primer for qPCR of Gene Sh3pxd2a

<400> SEQUENCE: 150
agctccgagt tctcttgttt c                                               21

<210> SEQ ID NO 151
<211> LENGTH: 20
<212> TYPE: DNA
<213> ORGANISM: Artificial Sequence
<220> FEATURE:
<223> OTHER INFORMATION: Forward primer for qPCR of Gene Tubb6

<400> SEQUENCE: 151
agaggcattt gaagacgagg                                                 20

<210> SEQ ID NO 152
<211> LENGTH: 21
<212> TYPE: DNA
<213> ORGANISM: Artificial Sequence
<220> FEATURE:
<223> OTHER INFORMATION: Reverse primer for qPCR of Gene Tubb6

<400> SEQUENCE: 152
ccagtgacat gcttagacca g                                               21

<210> SEQ ID NO 153
<211> LENGTH: 21
<212> TYPE: DNA
<213> ORGANISM: Artificial Sequence
<220> FEATURE:
<223> OTHER INFORMATION: Forward primer for qPCR of Gene Eva1c

<400> SEQUENCE: 153
accaaatgtg tagttcccag g                                               21

<210> SEQ ID NO 154
<211> LENGTH: 21
<212> TYPE: DNA
<213> ORGANISM: Artificial Sequence
<220> FEATURE:
<223> OTHER INFORMATION: Reverse primer for qPCR of Gene Eva1c

<400> SEQUENCE: 154
gaagactcgg ctattgacca g                                               21

<210> SEQ ID NO 155
<211> LENGTH: 17
<212> TYPE: DNA
```

<213> ORGANISM: Artificial Sequence
<220> FEATURE:
<223> OTHER INFORMATION: Forward primer for qPCR of Gene Pou3f1

<400> SEQUENCE: 155
gctctgtgca gtgaccc            17

<210> SEQ ID NO 156
<211> LENGTH: 26
<212> TYPE: DNA
<213> ORGANISM: Artificial Sequence
<220> FEATURE:
<223> OTHER INFORMATION: Reverse primer for qPCR of Gene Pou3f1

<400> SEQUENCE: 156
gtaaaatcca aagcaaaacc gaataa            26

<210> SEQ ID NO 157
<211> LENGTH: 21
<212> TYPE: DNA
<213> ORGANISM: Artificial Sequence
<220> FEATURE:
<223> OTHER INFORMATION: Forward primer for qPCR of Gene Prickle2

<400> SEQUENCE: 157
aaccagagga aacgtgagaa c            21

<210> SEQ ID NO 158
<211> LENGTH: 20
<212> TYPE: DNA
<213> ORGANISM: Artificial Sequence
<220> FEATURE:
<223> OTHER INFORMATION: Reverse primer for qPCR of Gene Prickle2

<400> SEQUENCE: 158
gtgatgcaaa cacagcgatg            20

<210> SEQ ID NO 159
<211> LENGTH: 19
<212> TYPE: DNA
<213> ORGANISM: Artificial Sequence
<220> FEATURE:
<223> OTHER INFORMATION: Forward primer for qPCR of Gene Map6

<400> SEQUENCE: 159
cagtgctacc aaacccgac            19

<210> SEQ ID NO 160
<211> LENGTH: 20
<212> TYPE: DNA
<213> ORGANISM: Artificial Sequence
<220> FEATURE:
<223> OTHER INFORMATION: Reverse primer for qPCR of Gene Map6

<400> SEQUENCE: 160
acagagcctt gatccttgtg            20

<210> SEQ ID NO 161
<211> LENGTH: 19
<212> TYPE: DNA
<213> ORGANISM: Artificial Sequence
<220> FEATURE:
<223> OTHER INFORMATION: Forward primer for qPCR of Gene Tomm70a

<400> SEQUENCE: 161
cagtggcgga ttttgatgc            19

<210> SEQ ID NO 162
<211> LENGTH: 20
<212> TYPE: DNA
<213> ORGANISM: Artificial Sequence
<220> FEATURE:
<223> OTHER INFORMATION: Reverse primer for qPCR of Gene Tomm70a

<400> SEQUENCE: 162
aacctttcat agctgcctgg                                           20

<210> SEQ ID NO 163
<211> LENGTH: 21
<212> TYPE: DNA
<213> ORGANISM: Artificial Sequence
<220> FEATURE:
<223> OTHER INFORMATION: Forward primer for qPCR of Gene Ube2g1

<400> SEQUENCE: 163
aatggaggga agacagaaac g                                         21

<210> SEQ ID NO 164
<211> LENGTH: 22
<212> TYPE: DNA
<213> ORGANISM: Artificial Sequence
<220> FEATURE:
<223> OTHER INFORMATION: Reverse primer for qPCR of Gene Ube2g1

<400> SEQUENCE: 164
cagtgccatg tttctcaatt gg                                        22

<210> SEQ ID NO 165
<211> LENGTH: 24
<212> TYPE: DNA
<213> ORGANISM: Artificial Sequence
<220> FEATURE:
<223> OTHER INFORMATION: Forward primer for qPCR of sgRNA cassette
      (quantification)

<400> SEQUENCE: 165
ctatgtggac tacagactgg aaag                                      24

<210> SEQ ID NO 166
<211> LENGTH: 20
<212> TYPE: DNA
<213> ORGANISM: Artificial Sequence
<220> FEATURE:
<223> OTHER INFORMATION: Reverse primer for qPCR of sgRNA cassette
      (quantification)

<400> SEQUENCE: 166
ctagggaggt cgcagtatct                                           20

<210> SEQ ID NO 167
<211> LENGTH: 34
<212> TYPE: DNA
<213> ORGANISM: Artificial Sequence
<220> FEATURE:
<223> OTHER INFORMATION: primers mU6-T2H-F to generate the dual-sgRNA
      constructs

<400> SEQUENCE: 167
ctaggatcca ttaggcgggt acagtgcagg ggaa                           34

<210> SEQ ID NO 168
<211> LENGTH: 34

```
<212> TYPE: DNA
<213> ORGANISM: Artificial Sequence
<220> FEATURE:
<223> OTHER INFORMATION: primers mU6-T2H-R2 to generate the dual-sgRNA
      constructs

<400> SEQUENCE: 168
atacggttat ccacgcggcc gcctaatgga tcct                                    34

<210> SEQ ID NO 169
<211> LENGTH: 42
<212> TYPE: DNA
<213> ORGANISM: Artificial Sequence
<220> FEATURE:
<223> OTHER INFORMATION: forward primer to clone an 83-bp SV40 nuclear
      localization site (NLS) with a linker

<400> SEQUENCE: 169
tacaaaggtg gaggtcggac cgaaggcagc ggctccccca ag                           42

<210> SEQ ID NO 170
<211> LENGTH: 40
<212> TYPE: DNA
<213> ORGANISM: Artificial Sequence
<220> FEATURE:
<223> OTHER INFORMATION: reverse primer to clone an 83-bp SV40 nuclear
      localization site (NLS) with a linker

<400> SEQUENCE: 170
aaatcgtcta aagcatccga ccctccgccg gaaccgccca                              40

<210> SEQ ID NO 171
<211> LENGTH: 50
<212> TYPE: DNA
<213> ORGANISM: Artificial Sequence
<220> FEATURE:
<223> OTHER INFORMATION: forward primer to amplify p300core

<400> SEQUENCE: 171
agtgggcggt tccggcggag ggtcgatttt caaaccagaa gaactacgac                   50

<210> SEQ ID NO 172
<211> LENGTH: 50
<212> TYPE: DNA
<213> ORGANISM: Artificial Sequence
<220> FEATURE:
<223> OTHER INFORMATION: reverse primer to amplify p300core

<400> SEQUENCE: 172
tatcaagctt gcatgcctgc aggttagtcc tggctctgcg tgtgcagctc                   50

<210> SEQ ID NO 173
<211> LENGTH: 21
<212> TYPE: DNA
<213> ORGANISM: Artificial Sequence
<220> FEATURE:
<223> OTHER INFORMATION: primer sgRNA-F for synthesize 72-bp sgRNA
      construct

<400> SEQUENCE: 173
gtatcccttg gagaaccacc t                                                  21

<210> SEQ ID NO 174
<211> LENGTH: 21
<212> TYPE: DNA
<213> ORGANISM: Artificial Sequence
<220> FEATURE:
```

```
<223> OTHER INFORMATION: primer sgRNA-R for synthesize 72-bp sgRNA
      construct

<400> SEQUENCE: 174
tgctgtttcc agcttagctc t                                            21

<210> SEQ ID NO 175
<211> LENGTH: 600
<212> TYPE: DNA
<213> ORGANISM: Artificial Sequence
<220> FEATURE:
<223> OTHER INFORMATION: Genomic DNA sequence of 500 bp upstream and 100
      bp downstream of Sox2 transcription start site

<400> SEQUENCE: 175
acagagcgca gtgccgcgga tgagcgcaga aacaatggca caccacctcc ggctctgcca     60
gcttcctgaa atactagttg gacagtcgcc ctgaaccacc catgggcctt gccccaccct    120
ggccccagct tcccgcgccc catccaccct tatgtatcca agagagagcc aatattccgt    180
agcatggggg aaaggagctg tcgtcttggt gctgtttacc cacttccttc gaacaggcgt    240
gcgccgtgac ctgttgctga aaacgggggg cggggggggg ggatacaaag gttccccagc    300
ggccggctgc gggcccgcct cccccgcgcg gttcggggca cagcgctctg ctgggctcgg    360
ctcggcggcg cggcaggccc cgccccctttt catgcaaaac cctctggcga ggctgggctc    420
gggcgcagga gccggcgctc gctgattggc cgccggaaac ccatttattc cctgacagcc    480
cccatcacat ggatggttgt ctattaactt gttcaaaaaa gtatcaggag ttgtcaaggc    540
agagaagaga gtgtttgcaa aaagggaaaa gtactttgct gcctctttaa gactagggct    600
```